(12) United States Patent
Webler et al.

(10) Patent No.: US 8,579,967 B2
(45) Date of Patent: *Nov. 12, 2013

(54) VALVE APTATION ASSIST DEVICE

(75) Inventors: William E. Webler, Escondido, CA (US); James D. Breeding, Houston, TX (US); Brad D. Bisson, Dighton, MA (US); Firas Mourtada, Pearland, TX (US); Gregory M. Hyde, Menlo Park, CA (US); Stephanie A. Szobota, Albany, CA (US); Gabriel Asongwe, San Jose, CA (US); Jeffrey T. Ellis, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 38 days.

This patent is subject to a terminal disclaimer.

(21) Appl. No.: 13/084,411

(22) Filed: Apr. 11, 2011

(65) Prior Publication Data

US 2011/0184512 A1 Jul. 28, 2011

Related U.S. Application Data

(62) Division of application No. 12/026,407, filed on Feb. 5, 2008, now Pat. No. 7,942,928, which is a division of application No. 10/712,553, filed on Nov. 12, 2003, now Pat. No. 7,404,824.

(60) Provisional application No. 60/426,663, filed on Nov. 15, 2002.

(51) Int. Cl.
 *A61F 2/24* (2006.01)
(52) U.S. Cl.
 USPC .......................................... 623/2.36
(58) Field of Classification Search
 USPC ................................. 623/2.36–2.38
 See application file for complete search history.

(56) References Cited

U.S. PATENT DOCUMENTS

| 3,177,543 A | 4/1965 | Fountain |
| 3,716,058 A | 2/1973 | Tanner et al. |

(Continued)

FOREIGN PATENT DOCUMENTS

| DE | 10161543 | 6/2003 |
| EP | 0377269 | 7/1990 |

(Continued)

OTHER PUBLICATIONS

Abbott Cardiovascular Systems, Non final office action dated Aug. 19, 2008 for U.S. Appl. No. 10/740,360, 8 pages.

(Continued)

*Primary Examiner* — Suzette J Gherbi
(74) *Attorney, Agent, or Firm* — Jonathan Feuchtwang; Blakely Sokoloff Taylor & Zafman LLP

(57) ABSTRACT

An apparatus including a tether, and an aptation device coupled to the tether at a position corresponding to a location to contact cusps of an atrioventricular valve during systole, wherein the tether and aptation device are suitable for percutaneous delivery to a patient. An apparatus including a support annulus comprising a length corresponding to a circumference of one of an interior portion of an atrium and an atrioventricular valve annulus; and an aptation device coupled to the support annulus corresponding to a location to contact cusps of an atrioventricular valve during at least one of systole when the support annulus is seated in one of an atrium and an atrioventricular valve annulus, wherein the support annulus and aptation device are suitable for percutaneous delivery to a patient. Also, a method of introducing an aptation device to contact cusps or leaflets of an atrioventricular valve.

19 Claims, 42 Drawing Sheets

(56) References Cited

U.S. PATENT DOCUMENTS

| | | |
|---|---|---|
| 4,128,100 A | 12/1978 | Wendorff |
| 4,719,924 A | 1/1988 | Crittenden et al. |
| 4,781,186 A | 11/1988 | Simpson et al. |
| 4,817,250 A | 4/1989 | Kurosaki |
| 4,830,023 A | 5/1989 | de Toledo et al. |
| 4,920,980 A | 5/1990 | Jackowski |
| 4,927,421 A | 5/1990 | Goble et al. |
| 4,932,962 A | 6/1990 | Yoon et al. |
| 4,994,067 A | 2/1991 | Summers |
| 5,040,548 A | 8/1991 | Yock |
| 5,061,273 A | 10/1991 | Yock |
| 5,100,418 A | 3/1992 | Yoon et al. |
| 5,100,421 A | 3/1992 | Christoudias |
| 5,102,421 A | 4/1992 | Anspach, Jr. |
| 5,116,337 A | 5/1992 | Johnson |
| 5,129,902 A | 7/1992 | Goble et al. |
| 5,141,520 A | 8/1992 | Goble et al. |
| 5,156,616 A | 10/1992 | Meadows et al. |
| 5,163,903 A | 11/1992 | Crittenden et al. |
| 5,171,233 A | 12/1992 | Amplatz et al. |
| 5,201,598 A | 4/1993 | Tehan |
| 5,234,443 A | 8/1993 | Phan et al. |
| 5,242,456 A | 9/1993 | Nash et al. |
| 5,246,441 A | 9/1993 | Ross et al. |
| 5,350,395 A | 9/1994 | Yock |
| 5,358,479 A | 10/1994 | Wilson |
| 5,370,662 A | 12/1994 | Stone et al. |
| 5,374,275 A | 12/1994 | Bradley et al. |
| 5,383,260 A | 1/1995 | Deschenes et al. |
| 5,431,673 A | 7/1995 | Summers et al. |
| 5,441,483 A | 8/1995 | Avitall |
| 5,451,233 A | 9/1995 | Yock |
| 5,456,667 A | 10/1995 | Ham et al. |
| 5,469,868 A | 11/1995 | Reger |
| 5,487,757 A | 1/1996 | Truckai et al. |
| 5,495,974 A | 3/1996 | Deschenes et al. |
| 5,518,162 A | 5/1996 | Deschenes et al. |
| 5,520,700 A | 5/1996 | Beyar et al. |
| 5,522,873 A | 6/1996 | Jackman et al. |
| 5,531,686 A | 7/1996 | Lundquist et al. |
| 5,554,184 A | 9/1996 | Machiraju |
| 5,569,277 A | 10/1996 | Evans et al. |
| 5,571,215 A | 11/1996 | Sterman et al. |
| 5,588,188 A | 12/1996 | Jermyn, Jr. |
| 5,609,598 A | 3/1997 | Laufer et al. |
| 5,613,937 A | 3/1997 | Garrison et al. |
| 5,617,854 A | 4/1997 | Munsif |
| 5,626,613 A | 5/1997 | Schmieding |
| 5,632,754 A | 5/1997 | Farley et al. |
| 5,640,955 A | 6/1997 | Ockuly et al. |
| 5,642,736 A | 7/1997 | Avitall |
| 5,643,319 A | 7/1997 | Green et al. |
| 5,681,280 A | 10/1997 | Rusk et al. |
| 5,681,346 A | 10/1997 | Orth et al. |
| 5,682,906 A | 11/1997 | Sterman et al. |
| 5,687,723 A | 11/1997 | Avitall |
| 5,709,224 A | 1/1998 | Behl et al. |
| 5,728,129 A | 3/1998 | Summers |
| 5,782,828 A | 7/1998 | Chen et al. |
| 5,810,869 A | 9/1998 | Kaplan et al. |
| 5,810,882 A | 9/1998 | Bolduc et al. |
| 5,823,955 A | 10/1998 | Kuck et al. |
| 5,824,008 A | 10/1998 | Bolduc et al. |
| 5,865,800 A | 2/1999 | Mirarchi et al. |
| 5,868,733 A | 2/1999 | Ockuly et al. |
| 5,868,767 A | 2/1999 | Farley et al. |
| 5,916,213 A | 6/1999 | Haissaguerre et al. |
| 5,954,731 A | 9/1999 | Yoon |
| 5,961,440 A | 10/1999 | Schweich, Jr. et al. |
| 5,964,772 A | 10/1999 | Bolduc et al. |
| 5,972,022 A | 10/1999 | Huxel |
| 5,989,284 A | 11/1999 | Laufer |
| 6,001,095 A | 12/1999 | de la Rama et al. |
| 6,001,104 A | 12/1999 | Benderev et al. |
| 6,001,127 A | 12/1999 | Schoon et al. |
| 6,004,332 A | 12/1999 | Yoon et al. |
| 6,017,358 A | 1/2000 | Yoon et al. |
| 6,021,340 A | 2/2000 | Randolph et al. |
| 6,027,514 A | 2/2000 | Stine |
| 6,036,715 A | 3/2000 | Yock |
| 6,045,497 A | 4/2000 | Schweich, Jr. et al. |
| 6,050,936 A | 4/2000 | Schweich, Jr. et al. |
| 6,051,008 A | 4/2000 | Saadat et al. |
| 6,059,715 A | 5/2000 | Schweich, Jr. et al. |
| 6,077,214 A | 6/2000 | Mortier et al. |
| 6,090,096 A | 7/2000 | St. Goar et al. |
| 6,093,199 A | 7/2000 | Brown et al. |
| 6,110,100 A | 8/2000 | Talpade |
| 6,113,609 A | 9/2000 | Adams |
| 6,117,176 A | 9/2000 | Chen |
| 6,120,520 A | 9/2000 | Saadat et al. |
| 6,123,699 A | 9/2000 | Webster, Jr. |
| 6,149,669 A | 11/2000 | Li |
| 6,161,543 A | 12/2000 | Cox et al. |
| 6,162,168 A | 12/2000 | Schweich, Jr. et al. |
| 6,164,283 A | 12/2000 | Lesh |
| 6,165,119 A | 12/2000 | Schweich, Jr. et al. |
| 6,165,120 A | 12/2000 | Schweich, Jr. et al. |
| 6,165,164 A | 12/2000 | Hill et al. |
| 6,165,183 A | 12/2000 | Kuehn et al. |
| 6,165,197 A | 12/2000 | Yock |
| 6,174,323 B1 | 1/2001 | Biggs et al. |
| 6,176,240 B1 | 1/2001 | Nikolchev et al. |
| 6,178,346 B1 | 1/2001 | Amundson et al. |
| 6,179,840 B1 | 1/2001 | Bowman |
| 6,182,664 B1 | 2/2001 | Cosgrove |
| 6,183,411 B1 | 2/2001 | Mortier et al. |
| 6,183,512 B1 * | 2/2001 | Howanec et al. ............ 623/2.36 |
| 6,187,040 B1 | 2/2001 | Wright |
| 6,190,401 B1 | 2/2001 | Green et al. |
| 6,190,408 B1 | 2/2001 | Melvin |
| 6,203,531 B1 | 3/2001 | Ockuly et al. |
| 6,210,407 B1 | 4/2001 | Webster, Jr. |
| 6,210,432 B1 | 4/2001 | Solem et al. |
| 6,231,561 B1 | 5/2001 | Frazier et al. |
| 6,231,587 B1 | 5/2001 | Makower |
| 6,241,728 B1 | 6/2001 | Gaiser et al. |
| 6,254,568 B1 | 7/2001 | Ponzi |
| 6,254,598 B1 | 7/2001 | Edwards et al. |
| 6,260,552 B1 | 7/2001 | Mortier et al. |
| 6,261,222 B1 | 7/2001 | Schweich, Jr. et al. |
| 6,261,228 B1 | 7/2001 | Mortier et al. |
| 6,264,602 B1 | 7/2001 | Mortier et al. |
| 6,267,781 B1 | 7/2001 | Tu |
| 6,269,819 B1 | 8/2001 | Oz et al. |
| 6,270,526 B1 | 8/2001 | Cox |
| 6,283,127 B1 | 9/2001 | Sterman et al. |
| 6,283,962 B1 | 9/2001 | Tu et al. |
| 6,287,339 B1 * | 9/2001 | Vazquez et al. ................ 623/2.4 |
| 6,290,674 B1 | 9/2001 | Roue et al. |
| 6,299,622 B1 | 10/2001 | Snow et al. |
| 6,306,133 B1 | 10/2001 | Tu et al. |
| 6,312,447 B1 | 11/2001 | Grimes |
| 6,325,823 B1 | 12/2001 | Horzewski et al. |
| 6,332,893 B1 | 12/2001 | Mortier et al. |
| 6,355,030 B1 | 3/2002 | Aldrich et al. |
| 6,358,277 B1 | 3/2002 | Duran |
| 6,371,978 B1 | 4/2002 | Wilson |
| 6,374,476 B1 | 4/2002 | Ponzi et al. |
| 6,402,780 B2 | 6/2002 | Williamson, IV et al. |
| 6,402,781 B1 | 6/2002 | Langberg et al. |
| 6,408,214 B1 | 6/2002 | Williams et al. |
| 6,416,549 B1 * | 7/2002 | Chinn et al. ................ 623/2.36 |
| 6,419,696 B1 | 7/2002 | Ortiz et al. |
| 6,436,110 B2 | 8/2002 | Bowman et al. |
| 6,447,517 B1 | 9/2002 | Bowman |
| 6,461,366 B1 | 10/2002 | Seguin |
| 6,482,224 B1 | 11/2002 | Michler et al. |
| 6,488,689 B1 | 12/2002 | Kaplan et al. |
| 6,493,575 B1 | 12/2002 | Kesten et al. |
| 6,497,707 B1 | 12/2002 | Bowman et al. |
| 6,500,167 B1 | 12/2002 | Webster, Jr. |
| 6,517,553 B2 | 2/2003 | Klein et al. |
| 6,537,198 B1 | 3/2003 | Vidlund et al. |
| 6,537,314 B2 | 3/2003 | Langberg et al. |

(56) References Cited

U.S. PATENT DOCUMENTS

| | | | |
|---|---|---|---|
| 6,551,271 B2 | 4/2003 | Nguyen | |
| 6,554,794 B1 | 4/2003 | Mueller et al. | |
| 6,554,852 B1 | 4/2003 | Oberlander | |
| 6,575,998 B2 | 6/2003 | Beyar | |
| 6,585,718 B2 | 7/2003 | Hayzelden et al. | |
| 6,599,311 B1 | 7/2003 | Biggs et al. | |
| 6,605,086 B2 | 8/2003 | Hayzelden et al. | |
| 6,610,058 B2 | 8/2003 | Flores | |
| 6,619,291 B2 | 9/2003 | Hlavka et al. | |
| 6,626,899 B2 | 9/2003 | Houser et al. | |
| 6,626,930 B1 | 9/2003 | Allen et al. | |
| 6,629,534 B1 | 10/2003 | St. Goar et al. | |
| 6,638,286 B1 | 10/2003 | Burbank et al. | |
| 6,648,903 B1 | 11/2003 | Pierson, III | |
| 6,656,221 B2 | 12/2003 | Taylor et al. | |
| 6,676,702 B2 | 1/2004 | Mathis | |
| 6,706,065 B2 | 3/2004 | Langberg et al. | |
| 6,709,442 B2 | 3/2004 | Miller et al. | |
| 6,709,456 B2 | 3/2004 | Langberg et al. | |
| 6,712,804 B2 | 3/2004 | Roue et al. | |
| 6,718,985 B2 | 4/2004 | Hlavka et al. | |
| 6,719,767 B1 | 4/2004 | Kimblad | |
| 6,723,038 B1 | 4/2004 | Schroeder | |
| 6,733,500 B2 | 5/2004 | Kelley et al. | |
| 6,746,472 B2 | 6/2004 | Frazier et al. | |
| 6,755,812 B2 | 6/2004 | Peterson et al. | |
| 6,761,734 B2 | 7/2004 | Suhr | |
| 6,764,510 B2 * | 7/2004 | Vidlund et al. | 623/2.34 |
| 6,770,070 B1 | 8/2004 | Balbierz | |
| 6,790,231 B2 | 9/2004 | Liddicoat et al. | |
| 6,800,090 B2 | 10/2004 | Alferness et al. | |
| 6,810,882 B2 | 11/2004 | Langberg et al. | |
| 6,824,562 B2 | 11/2004 | Mathis et al. | |
| 6,852,124 B2 | 2/2005 | Cox et al. | |
| 6,890,353 B2 | 5/2005 | Cohn et al. | |
| 6,905,476 B2 | 6/2005 | Ponzi | |
| 6,908,478 B2 | 6/2005 | Alferness et al. | |
| 6,911,035 B1 | 6/2005 | Blomme | |
| 6,951,549 B1 | 10/2005 | Beyerlein | |
| 6,960,229 B2 | 11/2005 | Mathis et al. | |
| 6,964,683 B2 | 11/2005 | Kowalsky et al. | |
| 6,964,684 B2 * | 11/2005 | Ortiz et al. | 623/2.37 |
| 6,966,926 B2 | 11/2005 | Mathis | |
| 6,989,028 B2 | 1/2006 | Lashinski et al. | |
| 6,997,950 B2 | 2/2006 | Chawla | |
| 6,997,951 B2 | 2/2006 | Solem et al. | |
| 7,073,504 B2 | 7/2006 | Callister et al. | |
| 7,087,064 B1 | 8/2006 | Hyde | |
| 7,104,999 B2 | 9/2006 | Overaker | |
| 7,160,318 B2 | 1/2007 | Greenberg et al. | |
| 7,166,126 B2 | 1/2007 | Spence et al. | |
| 7,186,264 B2 | 3/2007 | Liddicoat et al. | |
| 7,247,149 B2 | 7/2007 | Beyerlein | |
| 7,311,731 B2 | 12/2007 | Lesniak et al. | |
| 7,364,567 B2 | 4/2008 | Beyerlein | |
| 7,591,847 B2 | 9/2009 | Navia et al. | |
| 7,678,145 B2 * | 3/2010 | Vidlund et al. | 623/2.36 |
| 7,927,370 B2 * | 4/2011 | Webler et al. | 623/2.36 |
| 7,942,928 B2 * | 5/2011 | Webler et al. | 623/2.36 |
| 7,963,973 B2 * | 6/2011 | Nguyen et al. | 606/153 |
| 8,118,822 B2 * | 2/2012 | Schaller et al. | 606/157 |
| 2001/0003986 A1 | 6/2001 | Cosgrove | |
| 2001/0005787 A1 | 6/2001 | Oz et al. | |
| 2001/0018611 A1 * | 8/2001 | Solem et al. | 623/2.37 |
| 2001/0027322 A1 | 10/2001 | Bowman | |
| 2001/0044568 A1 | 11/2001 | Langberg et al. | |
| 2002/0010483 A1 | 1/2002 | Folmer et al. | |
| 2002/0010486 A1 | 1/2002 | Hirt | |
| 2002/0013571 A1 | 1/2002 | Goldfarb et al. | |
| 2002/0016628 A1 | 2/2002 | Langberg et al. | |
| 2002/0026216 A1 | 2/2002 | Grimes | |
| 2002/0029080 A1 * | 3/2002 | Mortier et al. | 623/2.36 |
| 2002/0032480 A1 * | 3/2002 | Spence et al. | 623/2.11 |
| 2002/0035361 A1 | 3/2002 | Houser et al. | |
| 2002/0042651 A1 | 4/2002 | Liddicoat et al. | |
| 2002/0077647 A1 | 6/2002 | Snow et al. | |
| 2002/0087169 A1 | 7/2002 | Brock et al. | |
| 2002/0087173 A1 | 7/2002 | Alferness et al. | |
| 2002/0103492 A1 | 8/2002 | Kaplan et al. | |
| 2002/0103532 A1 | 8/2002 | Langberg et al. | |
| 2002/0103533 A1 | 8/2002 | Langberg et al. | |
| 2002/0111637 A1 | 8/2002 | Kaplan et al. | |
| 2002/0161330 A1 | 10/2002 | Nguyen | |
| 2002/0165484 A1 | 11/2002 | Bowe et al. | |
| 2002/0165533 A1 | 11/2002 | Flores | |
| 2002/0165534 A1 | 11/2002 | Hayzelden et al. | |
| 2002/0169502 A1 * | 11/2002 | Mathis | 623/2.11 |
| 2002/0169504 A1 | 11/2002 | Alferness et al. | |
| 2002/0183835 A1 | 12/2002 | Taylor et al. | |
| 2002/0183836 A1 | 12/2002 | Liddicoat et al. | |
| 2002/0183837 A1 | 12/2002 | Streeter et al. | |
| 2002/0183841 A1 | 12/2002 | Cohn et al. | |
| 2002/0188170 A1 | 12/2002 | Santamore et al. | |
| 2003/0050598 A1 | 3/2003 | Hayzelden et al. | |
| 2003/0069593 A1 | 4/2003 | Tremulis et al. | |
| 2003/0078465 A1 | 4/2003 | Pai et al. | |
| 2003/0083538 A1 | 5/2003 | Adams et al. | |
| 2003/0093071 A1 | 5/2003 | Hauck et al. | |
| 2003/0105520 A1 | 6/2003 | Alferness et al. | |
| 2003/0120340 A1 | 6/2003 | Liska et al. | |
| 2003/0120341 A1 | 6/2003 | Shennib et al. | |
| 2003/0130731 A1 | 7/2003 | Vidlund et al. | |
| 2003/0144697 A1 | 7/2003 | Mathis et al. | |
| 2003/0144732 A1 | 7/2003 | Cosgrove et al. | |
| 2003/0167071 A1 | 9/2003 | Martin et al. | |
| 2003/0171776 A1 | 9/2003 | Adams et al. | |
| 2003/0212453 A1 * | 11/2003 | Mathis et al. | 623/2.11 |
| 2003/0216764 A1 | 11/2003 | Tu et al. | |
| 2004/0010231 A1 | 1/2004 | Leonhardt et al. | |
| 2004/0044350 A1 | 3/2004 | Martin et al. | |
| 2004/0044365 A1 | 3/2004 | Bachman | |
| 2004/0049207 A1 | 3/2004 | Goldfarb et al. | |
| 2004/0059351 A1 | 3/2004 | Eigler et al. | |
| 2004/0098092 A1 | 5/2004 | Butaric et al. | |
| 2004/0138683 A1 | 7/2004 | Shelton et al. | |
| 2004/0138744 A1 | 7/2004 | Lashinski et al. | |
| 2004/0148020 A1 | 7/2004 | Vidlund et al. | |
| 2004/0153147 A1 | 8/2004 | Mathis | |
| 2004/0260317 A1 | 12/2004 | Bloom et al. | |
| 2005/0045183 A1 | 3/2005 | Callister et al. | |
| 2005/0055089 A1 | 3/2005 | Macoviak et al. | |
| 2005/0075727 A1 | 4/2005 | Wheatley | |
| 2005/0085844 A1 | 4/2005 | Tremulis et al. | |
| 2005/0149182 A1 * | 7/2005 | Alferness et al. | 623/2.36 |
| 2005/0209633 A1 | 9/2005 | Callister et al. | |
| 2005/0267571 A1 | 12/2005 | Spence et al. | |
| 2005/0267573 A9 | 12/2005 | Macoviak et al. | |
| 2006/0020335 A1 * | 1/2006 | Kowalsky et al. | 623/2.36 |
| 2006/0041306 A1 | 2/2006 | Vidlund et al. | |
| 2006/0095025 A1 | 5/2006 | Levine et al. | |
| 2006/0282161 A1 | 12/2006 | Huynh et al. | |
| 2008/0091264 A1 | 4/2008 | Machold et al. | |

FOREIGN PATENT DOCUMENTS

| | | |
|---|---|---|
| WO | WO-98/29041 | 7/1998 |
| WO | WO-9829041 | 7/1998 |
| WO | WO-99/00059 | 1/1999 |
| WO | WO-9900059 | 1/1999 |
| WO | WO-99/13777 | 3/1999 |
| WO | WO-9913777 | 3/1999 |
| WO | WO-99/30647 | 6/1999 |
| WO | WO-9930647 | 6/1999 |
| WO | WO-99/44534 | 9/1999 |
| WO | WO-9944534 | 9/1999 |
| WO | WO-0003759 | 1/2000 |
| WO | WO-00/06026 | 2/2000 |
| WO | WO-00/06027 | 2/2000 |
| WO | WO-00/06028 | 2/2000 |
| WO | WO-0006026 | 2/2000 |
| WO | WO-0006027 | 2/2000 |
| WO | WO-0006028 | 2/2000 |
| WO | WO-0016700 | 3/2000 |
| WO | WO-0060995 | 10/2000 |

(56) References Cited

FOREIGN PATENT DOCUMENTS

| | | |
|---|---|---|
| WO | WO-00060995 | 10/2000 |
| WO | WO-0100111 | 1/2001 |
| WO | WO-0100114 | 1/2001 |
| WO | WO-01/28455 | 4/2001 |
| WO | WO-0126557 | 4/2001 |
| WO | WO-0128432 | 4/2001 |
| WO | WO-0128455 | 4/2001 |
| WO | WO-01026557 | 4/2001 |
| WO | WO-01028432 | 4/2001 |
| WO | WO-01/49213 | 7/2001 |
| WO | WO-0149213 | 7/2001 |
| WO | WO-01/54618 | 8/2001 |
| WO | WO-0154618 | 8/2001 |
| WO | WO-0189440 | 11/2001 |
| WO | WO-0200099 | 1/2002 |
| WO | WO-0201999 | 1/2002 |
| WO | WO-0234167 | 5/2002 |
| WO | WO-0239925 | 5/2002 |
| WO | WO-02/053206 | 7/2002 |
| WO | WO-02053206 | 7/2002 |
| WO | WO-02/060352 | 8/2002 |
| WO | WO-02/062263 | 8/2002 |
| WO | WO-02/062270 | 8/2002 |
| WO | WO-02/062408 | 8/2002 |
| WO | WO-02060352 | 8/2002 |
| WO | WO-02062263 | 8/2002 |
| WO | WO-02062270 | 8/2002 |
| WO | WO-02062408 | 8/2002 |
| WO | WO-02063533 | 8/2002 |
| WO | WO-02078576 | 10/2002 |
| WO | WO-03049619 | 6/2003 |
| WO | WO-03073913 | 9/2003 |
| WO | WO-2004012789 | 2/2004 |
| WO | WO-2004014282 | 2/2004 |
| WO | WO-2004045463 | 6/2004 |

OTHER PUBLICATIONS

Abbott Cardiovascular Systems, PCT International Preliminary Report on Patentability and Written Opinion for PCT Appln No. US2004/031403, mailed Apr. 13. 2006.

Abbott Cardiovascular Systems, PCT International Search Report and Written Opinion of the International Searching Authority for PCT Appln No. US2004/031403, mailed May 18, 2005.

Abbott Cardiovascular Systems, PCT International Search Report for PCT Appln. No. US2004/031403, mailed Feb. 15, 2005.

Abbott Cardiovascular Systems, Final Office Action dated Apr. 15, 2009 for U.S. Appl. No. 10/676,616.

Abbott Cardiovascular Systems, Non final office action dated Jun. 12, 2009 for U.S. Appl. No. 11/240,569.

Abbott Cardiovascular Systems, Final Office Action dated Aug. 3, 2009 for U.S. Appl. No. 10/464,132.

Abbott Cardiovascular Systems, Final Office Action mailed Nov. 15, 2010 for U.S Appl. No. 12/026,407., 6 pages.

Abbott Cardiovascular Systems, Final Office Action mailed Dec. 14, 2010 for U.S. Appl. No. 11/445,694, 12 pages.

Abbott Cardiovascular Systems, Non final office action mailed Oct. 25, 2010 for U.S. Appl. No. 12/026,439.

Abbott Cardiovascular Systems, Final office action dated Aug. 3, 2010 for U.S. Appl. No. 10/464,132.

Abbott Cardiovascular Systems, Non final office action dated May 28, 2010 for U.S. Appl. No. 12/026,407.

Abbott Cardiovascular Systems, Non-Final Office Action mailed May 20, 2010 for U.S. Appl. No. 11/445,694.

Abbott Cardiovascular Systems, Final office action dated Apr. 13, 2010 for U.S. Appl. No. 11/112,546.

Abbott Cardiovascular Systems, PCT Search Report and Written Opinion dated Nov. 16, 2007 for PCT/US2007/011948.

Abbott Cardiovascular Systems, Non final office action dated Jan. 28, 2010 for U.S. Appl. No. 12/026,439.

Abbott Cardiovascular Systems, Final office action dated Dec. 28, 2009 for U.S. Appl. No. 11/240,589.

Abbott Cardiovascular Systems, Final Office Action dated Mar. 24, 2009 for U.S. Appl. No. 10/740,360.

Abbott Cardiovascular Systems, Non final office action dated Feb. 23, 2010 for U.S. Appl. No. 10/464,132.

Abbott Cardiovascular Systems, PCT Invitation to Pay Additional Fees for PCT International Appln. No. PCT/US03/36633, mailed May 19, 2004.

Abbott Cardiovascular Systems, PCT Invitation to Pay Additional Fees for PCT International Appln. No. PCT/US2004/031403, mailed Feb. 15, 2005.

Abbott Cardiovascular Systems, PCT Invitation to Pay Additional Fees for PCT International Appln. No. US03/36633, mailed May 19, 2004.

Bonow, Robert O., et al., "Guidelines for the Management of Patients with Valvular Health Disease", Report of American College of Cardiology/American Heart Assoc. Task Force on Practice Guidelines, (Committee on Management of Patients with Valvular Heart Disease), American College of Cardiology and American Heart Assoc., Inc., (1998), pp. 1949-1984.

Messas, et al., "Chordal Cutting a New Therapeutic approach for Ischmic Mitral Regurgitation", American heart Association Inc., (2001), 1958-1963.

\* cited by examiner

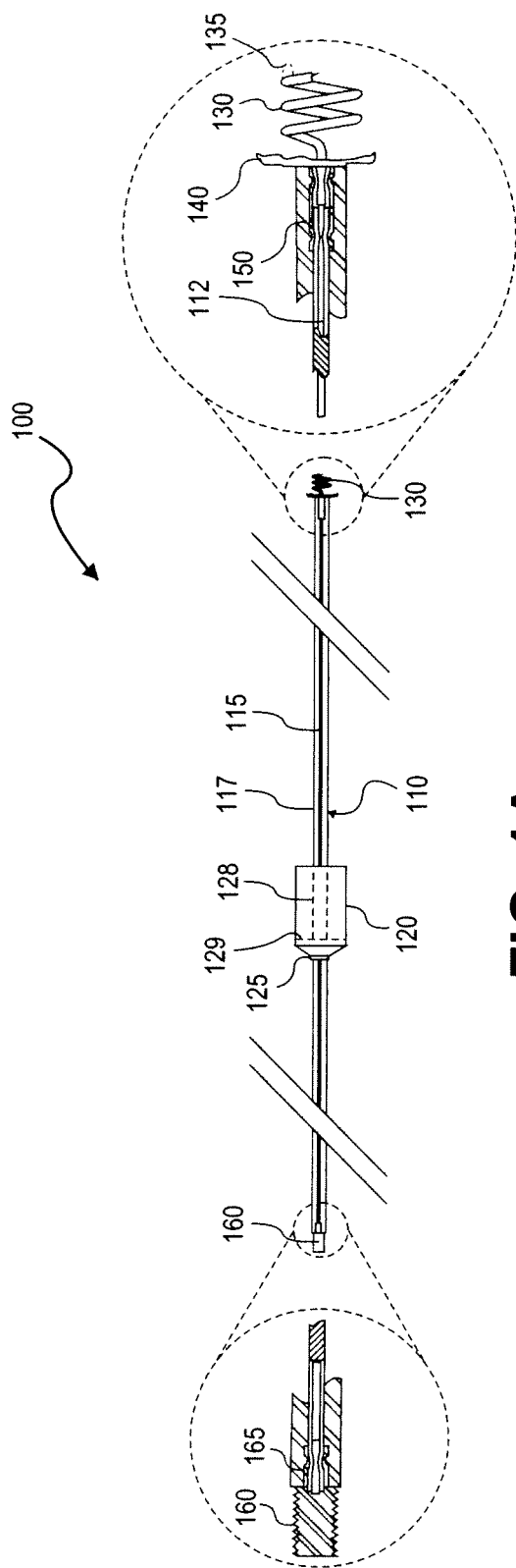

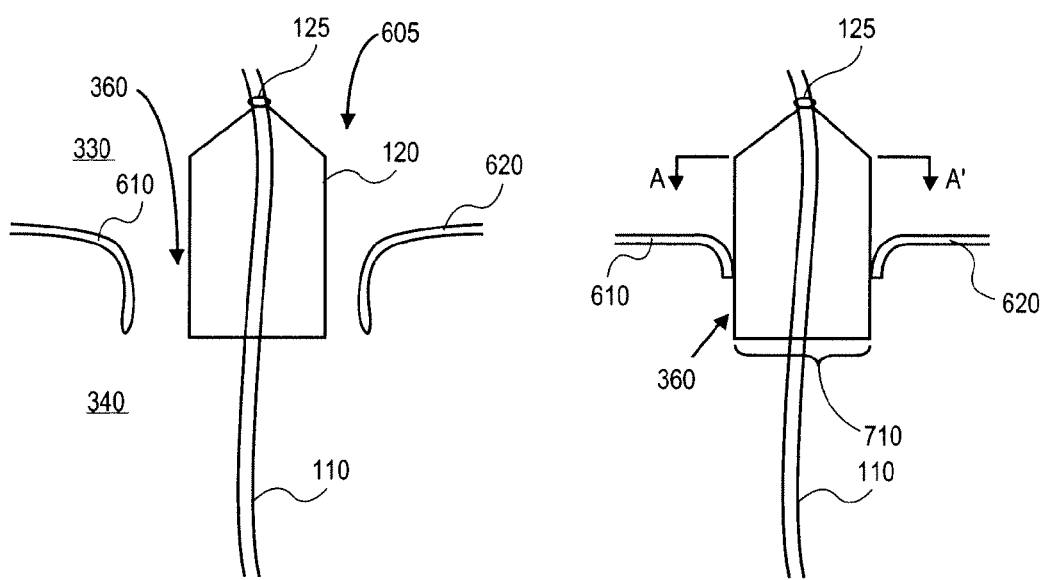
FIG. 6 FIG. 7

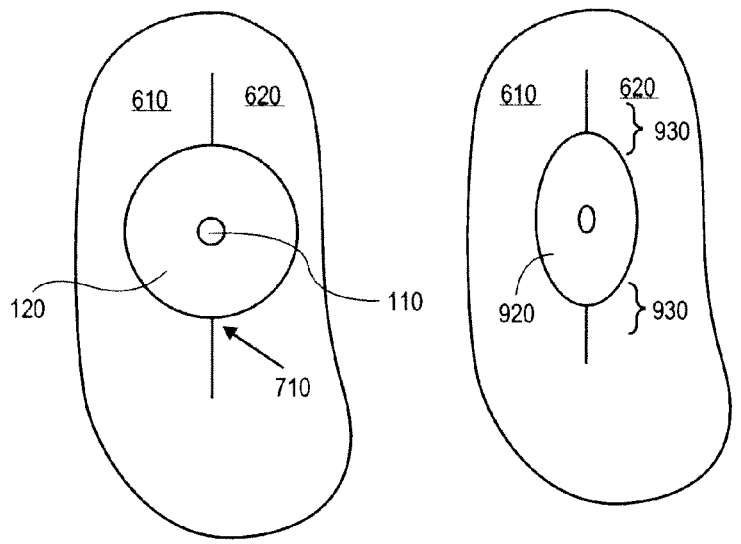
FIG. 8    FIG. 9
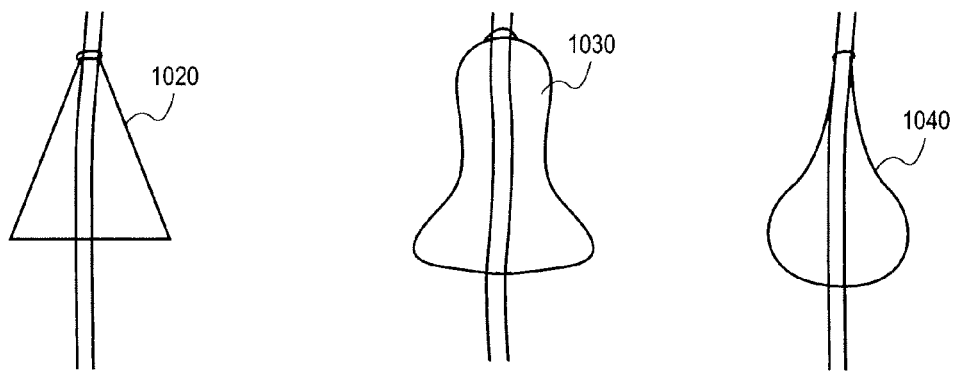
FIG. 10A    FIG. 10B    FIG. 10C
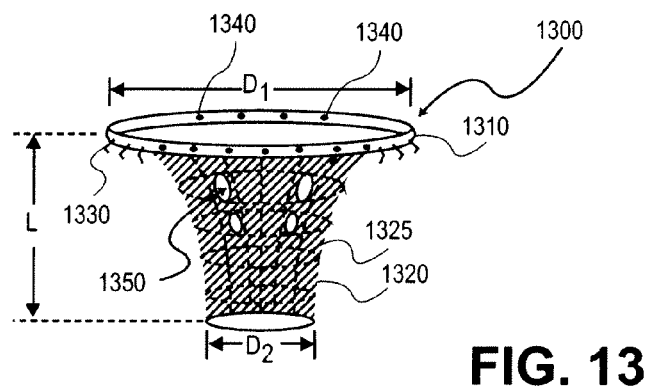
FIG. 13

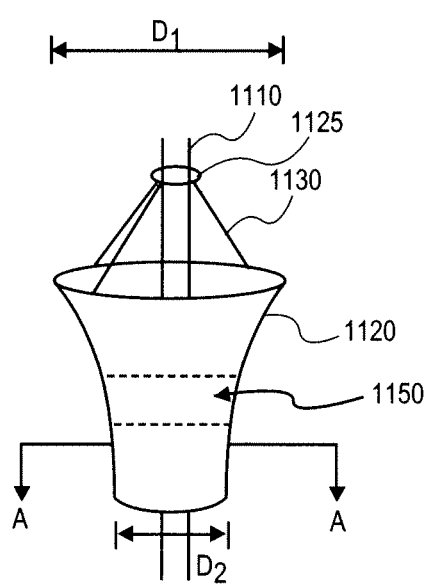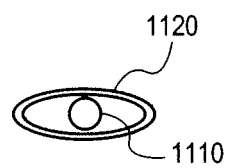
FIG. 11A　　FIG. 11B

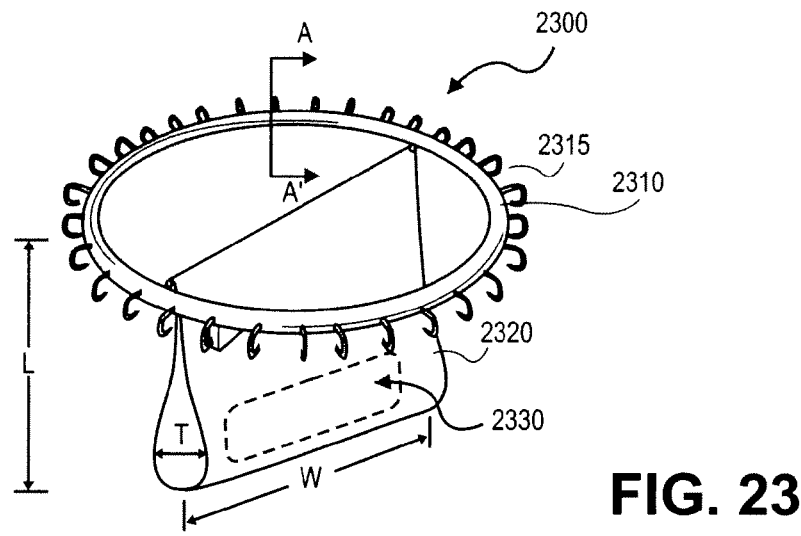
FIG. 23
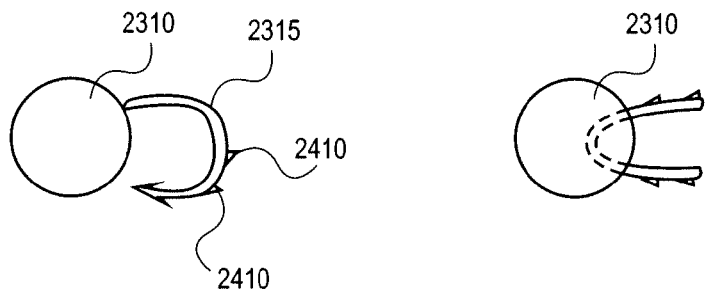
FIG. 24     FIG. 25
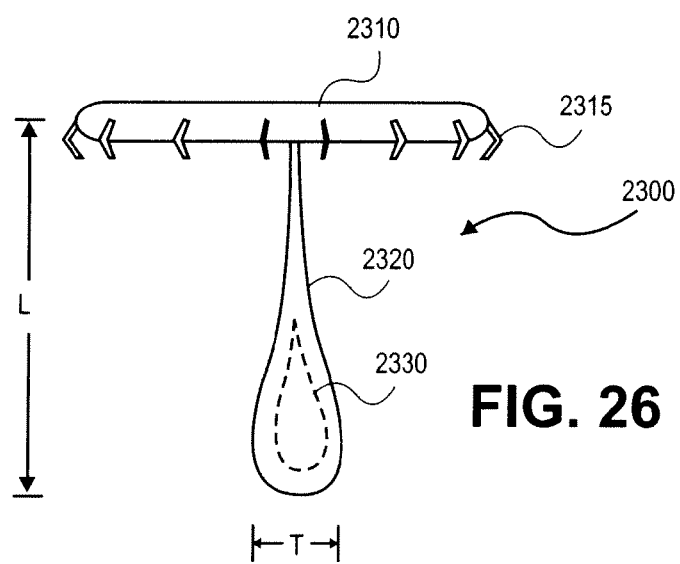
FIG. 26

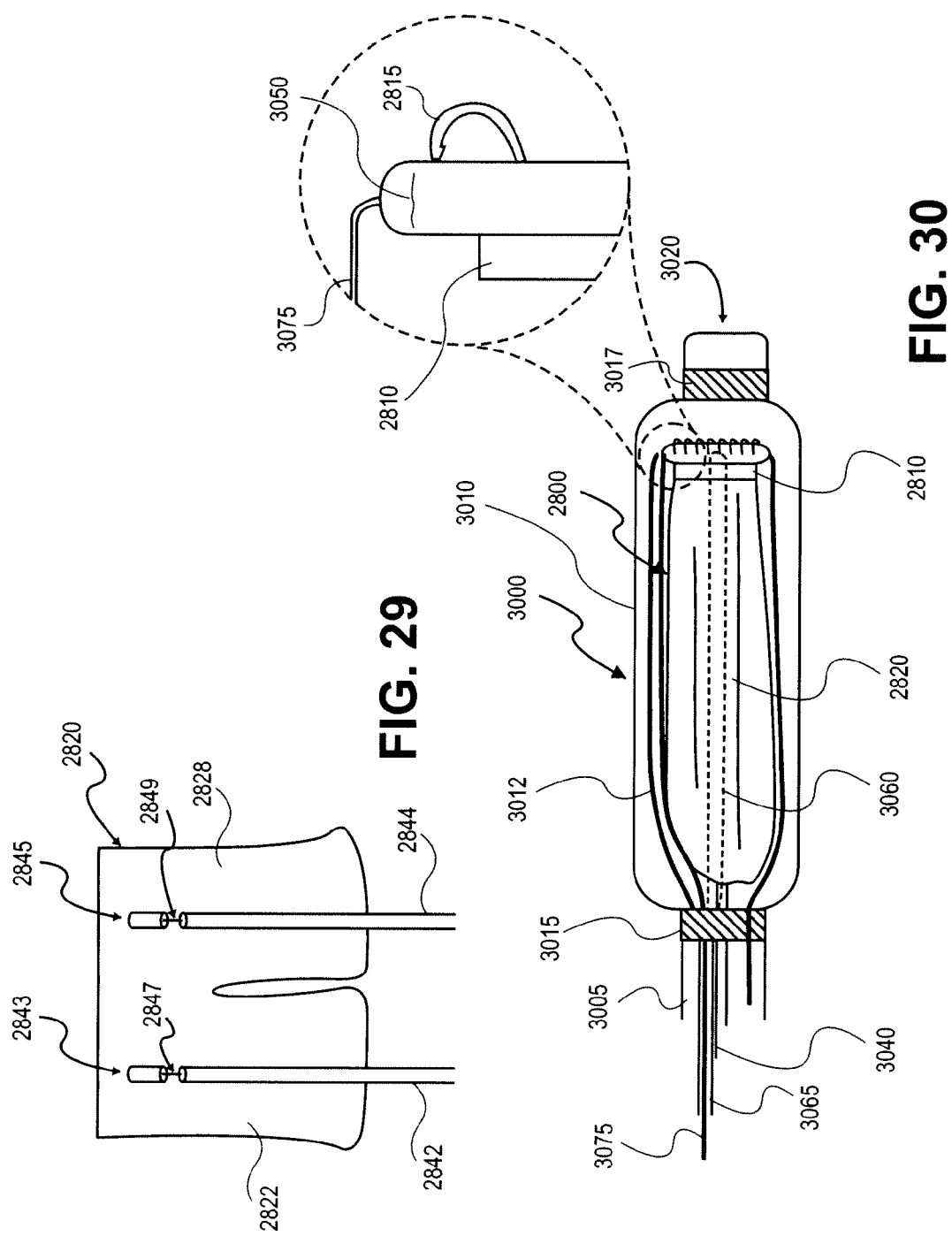

VALVE APTATION ASSIST DEVICE

CROSS-REFERENCE TO RELATED APPLICATION

This application is a divisional of U.S. patent application Ser. No. 12/026,407 filed Feb. 5, 2008, now U.S. Pat. No. 7,742,928, which is a divisional of U.S. patent application Ser. No. 10/712,553, filed Nov. 12, 2003 (now U.S. Pat. No. 7,404,824), which claims the benefit of U.S. Provisional Patent Application No. 60/426,663, filed Nov. 15, 2002.

BACKGROUND

1. Field

Atrioventricular valve repair, including percutaneous atrioventricular valve repair.

2. Background

Generally speaking, oxygenated blood travels from the lungs to the left atrium by way of the pulmonary veins. The veins from the systemic circuit, the venae cavae and coronary sinus carry blood deficient in oxygen into the right atrium. The right ventricle takes blood received from the right atrium and sends it to the lungs, while the left ventricle takes blood received from the left atrium and sends it to the aorta.

The atrioventricular valves between respective ones of the atria and ventricles play important roles in the transport of blood through the body. The atrioventricular valves open during diastole, when the heart muscle relaxes, to allow blood to flow from the atria into the ventricles. The atrioventricular valves close during systole, when the heart muscle contracts, preventing the backflow of blood into the atria and allowing blood from the ventricles to be efficiently pumped into the lungs via the pulmonary artery and to the rest of the body via the aorta.

The mitral valve is the atrioventricular valve that controls blood flow from the left atrium into the left ventricle. The mitral valve is a bicuspid valve, describing the two cusps or leaflets that open and close the valve. The cusps or leaflets are attached to a muscular and fibrous ring around the orifice (mitral valve annulus) and their apices hang down into the left ventricle. When the ventricle fills with blood and begins to contract, the valve cusps or leaflets flow into position in the atrioventricular opening and are forced shut (coaptate) by the increasing pressure. To prevent the valve cusps or leaflets from turning into the left atrium and regurgitating blood, tendinous cords, the chordae tendineae, are attached to the free margins and ventricular surfaces of the cusps or leaflets. At the other ends, these cords are attached to one of a respective pair of papillary muscles projecting from the ventricular wall. By contracting, these muscles maintain the integrity of the valve during ventricular contraction or systole.

When the two cusps or leaflets of the mitral valve do not completely close, there is backflow, or regurgitation of blood. The backflow increases the pressure in the left atrium which leads to pulmonary hypertension and dilation of the heart which are the most common symptoms to congestive heart failure. A heart then has to work harder pumping blood for the body which can lead to heart damage. Incomplete closing of the mitral valve cusps or leaflets is common, occurring generally in about seven percent of the population. Conditions contributing to incomplete closure of the mitral valve cusps or leaflets include genetic defects, infections, coronary artery disease, myocardial infarction, or congestive heart failure. These conditions contribute to mitral valve regurgitation resulting from enlargement of the mitral valve annulus and/or movement of the papillary muscles away from the valve as a result of ventricular enlargement. When the annulus enlarges, the cusps or leaflets of the valve are no longer able to close (coaptate), because the distance between the two cusps or leaflets has increased too much for the cusps or leaflets to touch each other and thus close off blood flow to the left atrium during, for example, systole. Mitral valve regurgitation can also result as a secondary etiology due to the remodeling of a distorted left ventricle in ischemic heart disease. It is known that as the ventricle is remodeled, the papillary muscles can be displaced away from their natural position. This displacement alters the natural tethering of the cusps or leaflets and restricts the ability of the cusps or leaflets to close properly at the level of the annulus.

In general, most cases of mitral valve regurgitation are mild and the symptoms may be controlled with drugs. In more serious cases, the mitral valve can be repaired through a procedure known as annuloplasty, a surgical procedure in which a synthetic ring is placed around the valve annulus. Annuloplasty encourages aptation of the mitral valve cusps or leaflets by shrinking the size of the valve opening. In other instances, a faulty mitral valve must be surgically replaced with a new valve. These surgical repairs require the opening of the chest by sternotomy or at best through small incisions in the chest wall, heart lung bypass and stopping the heart beat. Further techniques under investigation include remodeling the adjacent coronary sinus and joining two middle edges of the cusps or leaflets where they should coaptate.

A second type of regurgitation occurs not necessarily by the enlargement of the mitral valve annulus but by the extending of a cusp or leaflet into the atrium during systole. A condition known as billowing occurs when the mitral valve cusps or leaflets do not meet well but instead get pushed up into the atrium. A condition known as prolapse occurs generally when a single cusp or leaflet extends into the atrium causing incomplete closure of the valve. A condition known as flail typically occurs when a tendon is ruptured and the corresponding cusp or leaflet extends into the atrium during systole.

Current mitral valve regurgitation may be diagnosed by Trans-Thoracic Echo (TTE) in many patients or Trans-Esophageal Echo (TEE). TEE tends to provide the most reliable and definitive structural and functional mitral valve information. Both TTE and TEE imaging devices are reusable.

TTE images the heart with a hand-held transducer from under the rib cage and between the ribs and thus has limited views of the mitral valve. TTE becomes less reliable in large or obese patients as the increased distance from the probe to the valve reduces image echo strength and resolution. Also, the imaging windows between the ribs become narrower as the probe is further away from the ribs in obese patients.

TEE images the heart from inside the esophagus (canal from the throat to the stomach) using an articulating probe and is relatively unaffected by patient size. However, it is very uncomfortable for a conscious patient and some patients cannot tolerate it while conscious. TEE is commonly used to check a surgical repair prior to closing the chest.

Another diagnostic technique is Intra-Cardiac Echo (ICE). One ICE is the ACUSON ACU-NAV™ System (10F) manufactured by Siemens Corporation. ICE is a one time use, array type articulating probe, placed in the right heart and, consequently, is relatively expensive and thus is not widely used at this time. It provides good views of the mitral valve, but may not have as good Doppler views as TTE or TEE.

The historical standard for diagnosing mitral valve regurgitation is angiographically observing the regurgitation of contrast injected into the left ventricle and is the basis of the common grading system for regurgitation (1+, 2+, etc.). It is widely recognized that the angiographic technique is not as reliable or as good an outcome predictor as the measurements of regurgitant volume and flow cross-section that can be made with the Doppler enhancements of modern echo systems.

SUMMARY

In one embodiment, an apparatus is disclosed. The apparatus includes a tether having a length suitable for extending through a ventricle of a heart from, at a proximal end, an atrioventricular valve annulus to, at a distal end, a wall of a ventricle or one or more papillary muscles. Representatively, at a distal end, the apparatus may include a hook, or hooks and/or a barb or barbs connected to the tether. The apparatus also includes an aptation device connected to the tether at a position corresponding to a location to contact one or more cusps or leaflets of an atrioventricular valve during systole. The apparatus disclosed is suitable for percutaneous delivery to a patient.

In another embodiment, a method is described. The method includes percutaneously advancing an aptation device to a location to contact one or more cusps or leaflets of an atrioventricular valve and tethering the aptation device to a wall of a ventricle. In this manner, the apparatus and/or method may be used to modify (e.g., improve) the atrioventricular valve function, including the aptation of valve cusps or leaflets during contraction (e.g., systole). The capability to insert an atrioventricular valve modifying apparatus percutaneously provides an approach that can reduce patient discomfort and improve recovery and hospitalization time over current techniques such as annuloplasty. In one embodiment, the aptation device is connected to the tether at a position corresponding to a position between cusps of an atrioventricular valve when the tether is positioned through an atrioventricular valve. The aptation device may have a size suitable, when placed between the cusps of an atrioventricular valve, that the cusps aptate against the aptation device. In this manner, atrioventricular valve regurgitation conditions resulting from, among other things, a disconnect between cusps at systole, may be corrected with the aptation device. In another embodiment, the aptation device resides substantially above the cusps or leaflets, near the level of the valve annulus, or completely within an atrium during systole when the tether is positioned through an atrioventricular valve. In this manner, one or both cusps or leaflets particularly cusps or leaflets that would otherwise extend improperly into the atrium, can contact a surface of the aptation device during systole. An apparatus such as described is suitable for correcting problems such as prolapse, billowing and flail.

In another embodiment, an apparatus is described. The apparatus includes a support annulus including a length corresponding to a circumference of one of an interior portion of an atrium and an atrioventricular valve annulus. The apparatus also includes an aptation device connected to the support annulus at a location corresponding to a location to contact cusps of an atrioventricular valve during at least one of systole and diastole when the support annulus is seated in either the atrium or the atrioventricular valve annulus. The support annulus and aptation device are suitable for percutaneous delivery to a patient offering an improvement in atrioventricular valve modification without more invasive surgical procedures.

An apparatus including a support annulus may or may not have a tether that may support the apparatus at a location where the apparatus may modify an atrioventricular valve. The support annulus is of a size and shape corresponding to an interior diameter of an atrium or an atrioventricular valve annulus. The aptation device, in one embodiment, is connected at a first point and a second point on the support annulus where the first point and second point are selected such that when the support annulus adopts a shape corresponding to the shape of an atrium or an atrioventricular valve annulus, the adaptation device forms a bridge across the support annulus. Representative aptation devices include, but are not limited to, a bladder having a length dimension, when the support annulus is positioned in an atrium or an atrioventricular valve annulus, suitable to extend between cusps or leaflets of an atrioventricular valve. The volume of the bladder may be modified to conform the aptation device to a necessary size to modify (e.g., improve) the aptation of the atrioventricular valve. Alternatively, the aptation device may include a portion suitable, when the support annulus is positioned in an atrium or atrioventricular valve annulus, to contact cusps or leaflets of an atrioventricular valve to address problems of prolapse, billowing, or flail.

In a further embodiment, a method is described. The method includes percutaneously advancing an aptation device to an atrioventricular valve location and deploying the aptation device to contact cusps of the atrioventricular valve. Suitable aptation devices include, but are not limited to, aptation devices that modify the aptation of the atrioventricular valve either by being positioned in the valve or above the valve during systole.

BRIEF DESCRIPTION OF THE DRAWINGS

The features, aspects, and advantages of the invention will become more thoroughly apparent from the following detailed description, appended claims, and accompanying drawings in which:

FIG. 1A shows a schematic, view of an embodiment of an apparatus useful in atrioventricular valve modification.

FIG. 6 shows a schematic side sectional illustration of an apparatus including the aptation device disposed between cusps of an atrioventricular valve when the valve is open.

FIG. 7 shows a schematic side sectional view of the apparatus of FIG. 6 with the aptation device disposed within an atrioventricular valve when the valve is closed.

FIG. 8 shows the apparatus of FIG. 7 through line A-A' of FIG. 7.

FIG. 9 shows a second embodiment of an aptation device of FIG. 7 through line A-A' of FIG. 7.

FIG. 10A shows a cross-sectional schematic view of a portion of another embodiment of an apparatus suitable for modifying an atrioventricular valve with a conical shaped aptation device.

FIG. 10B shows a cross-sectional schematic view of a portion of another embodiment of an apparatus suitable for modifying an atrioventricular valve with a bell-shaped aptation device.

FIG. 10C shows a cross-sectional schematic view of a portion of another embodiment of an apparatus suitable for modifying an atrioventricular valve with a tear drop shape.

FIG. 11A shows a perspective top side view of another embodiment of a portion of an apparatus suitable for modifying an atrioventricular valve with a conical shaped aptation device.

FIG. 11B shows the aptation device of FIG. 11A through line A-A'.

FIG. 13 shows a perspective top schematic view of another embodiment of an apparatus suitable for modifying an atrioventricular valve.

FIG. 23 shows a perspective top schematic view of another embodiment of an apparatus suitable for modifying an atrioventricular valve.

FIG. 24 shows a portion of the apparatus of FIG. 23 through line A-A' illustrating an anchoring device.

FIG. 25 shows a portion of the apparatus of FIG. 23 through line A-A' illustrating an alternative type of anchoring device.

FIG. 26 shows a schematic side view of the apparatus of FIG. 23.

FIG. 29 shows a portion of the apparatus of FIG. 28 through line A-A'.

FIG. 30 shows the apparatus of FIG. 28 confined in a catheter sheath.

DETAILED DESCRIPTION

Figure 1B:
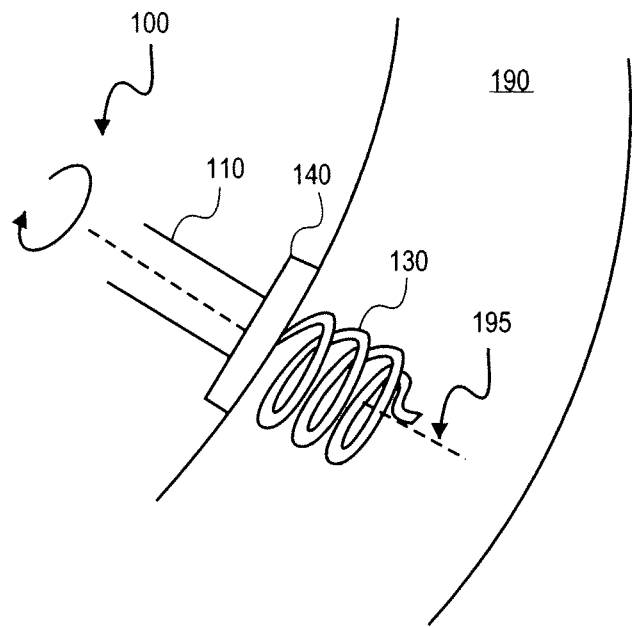
FIG. 1B shows a magnified view of a distal portion of the apparatus of FIG. 1A deployed in a tissue according to a first embodiment.

In the following description, various embodiments of an apparatus suitable, in one aspect, for use in modifying an atrioventricular valve (such as by improving the aptation or closing of the valve) are described. Methods of locating apparatuses and improving atrioventricular valve aptation are also described. Various properties, dimensions, functionalities, and techniques (collectively "attributes") are described with regard to the embodiments. It is appreciated that many if not all the attributes, may be applied to all of the embodiments. Thus, the following description should be read broadly in the sense of incorporating various attributes (where not specifically mentioned) to each embodiment.

FIG. 1A shows a schematic side view of an embodiment of an apparatus suitable for use in modifying an atrioventricular valve. Apparatus 100 includes tether 110 and aptation device 120 each of a size suitable for percutaneous delivery to an atrium and/or a ventricle of a heart. In one embodiment, tether 110 has a length suitable for being connected, at a proximal end, to an interatrial septum and, at a distal end, to a wall of a ventricle, such as the apex of the left ventricle, or to papillary muscles within the ventricle. A representative length is on order of 10 to 20 centimeters. Aptation device 120 is connected to tether 110 at a position corresponding to a location to contact cusps or leaflets of an atrioventricular valve during, for example, systole. In one embodiment, aptation device 120 is connected to tether 110 at a proximal end of aptation device 120 (at connection 125).

In one embodiment, tether 110 is adapted to be fixed (anchored) to a wall of a ventricle, such as the left ventricle, or papillary muscles by twisting (screwing) an anchoring device at a distal end of tether 110 into the wall of the ventricle. When delivered percutaneously, tether 110 is provided with sufficient torsional stiffness to allow it to respond in kind at a distal end to a torque applied at a proximal end of the tether. In one embodiment, tether 110 includes duplex spring 115 to provide the torsional stiffness. A duplex spring is a spring within a spring, each spring wound in a different direction. The springs are usually multi-filar (contain more than one wire). When torqued/twisted in the proper direction, the diameter of the outer coil tends to decrease and the diameter of the inner coil tends to increase, locking the inner coil and the outer coil together and providing an increased torsional modulus. Duplex springs are often made of various 18-8 type stainless steel (SST) wires like 302 and 304. For duplex springs that are used as a part of pacing leads (IDF3538), it is common to include an inner core of a better conductor than SST, like silver, within the SST wire of the duplex spring. If apparatus 100 were to be placed in a patient that could benefit from bi-ventricular pacing, then the duplex spring could be made from pacing lead-like materials, the tether lengthened and it could function, for example, as the left heart pacing lead, avoiding the coronary sinus pacing lead placement procedure. The outside diameter (OD) of a representative duplex spring (duplex spring 115) will be on the order of 0.030 inches to 0.125 inches. Although a duplex spring is described with reference to FIG. 1A, a duplex spring is not the only construction possible. For example, three or more layers of counter wound springs or wires as well as braided wires may also be suitable. In the embodiment shown in FIG. 1A, tether 110 also includes sheath 117 covering duplex spring 115.

Duplex (and three or more layers) springs can be made to resist compression, usually by winding the inner spring closed (little or no gap between adjacent windings), but are generally poor in tensile characteristics. Coating of tether 110 may not provide an adequate increase in the tensile characteristics of the tether. Increased tensile characteristics (higher tensile modulus) may be required for the delivery of certain designs (e.g., pressure on aptation device 120 during systole and setting of attachment hooks). A higher tensile modulus can be attained by attaching (e.g., by an adhesive) a fiber(s) (e.g., Kevlar, nylon, etc.) or a wire(s) to the inner diameter (ID) or outside diameter (OD) of the spring at two or more places.

Duplex springs are also very flexible (low flexural modulus) which is beneficial in many portions of apparatus 100 and this can be preserved by using a flexible fibers(s) or wire(s) to provide desired tensile properties. However, in the portion of the tether between helical anchor 130 and connection 125 of aptation device 120 to tether 110 both a higher tensile modulus and a higher flexural modulus may be required to keep aptation device 120 in position during diastole and systole. During systole, for example, aptation device 120 is subjected to the pressure differential between a ventricle and an atrium and thus tether 110 is placed in tension in this portion. A high tensile modulus keeps aptation device 120 from changing its position due to tether 110 extension as ventricular pressure rises and falls (reduces requirements for aptation device placement accuracy and reduces possible leaflet abrasion). During diastole, when the blood in the atrium rushes into the ventricle, aptation device 120 and thus, tether 110 are under pressure and subjected to viscous forces that tend to wash the aptation device 120 into the ventricle. A higher flexural modulus will prevent tether 110 from buckling (bending too much) and allowing aptation device 120 to wash into the ventricle. If aptation device 120 washed into the ventricle, then it could be forced into the closed valve cusps or leaflets during systole and damage the cusps or leaflets. If aptation device 120 got between the cusps or leaflets before they closed fully, there could still be some abrasion and the inertia of a blood filled aptation device 120 could place undesirably high forces on a distal anchor for tether 110 when tether 110 straightened. The higher flexural modulus can be accomplished by the choice of material for sheath 117 and/or by choosing a larger outside diameter (OD) wire to provide an increased tensile modulus. The enlarged distal view of FIG. 1A shows wire 112 in the inner diameter (ID) of duplex spring 115. Wire 112 may optionally be included to increase the tensile modulus and/or the flexural modulus of tether 110. In one embodiment, wire 112 is attached to the distal end of duplex spring 115 and to duplex spring 115 at a point corresponding approximately with connection 125 of aptation device 120 to tether 110.

In one embodiment, an anchoring device at the distal end of tether 110 of apparatus 100 is adapted to be twisted (screwed) into a wall of a ventricle. FIG. 1A shows helical anchor 130 connected to a distal end of tether 110 (e.g., a distal end of duplex spring 115). Helical anchor 130 is selected, in one embodiment, to be completely embedded within the myocardial tissue of the left ventricle. Thus, in one embodiment, helical anchor 130 is a material such as stainless steel or other material having a length corresponding up to the thickness of myocardial tissue or greater and selected to be sufficient to secure tether 110 to the ventricle wall during contractions of the heart. In an application where duplex spring 115 functions in the additional capacity as a pacing lead, helical anchor 130 may, alternatively be, or additionally include platinum iridium as a conductive lead. Helical anchor 130 may also include laterally and/or longitudinally extending barbs 135 (shown in ghost lines). Helical anchor 130 may be connected to duplex spring 115 by, for example, crimp ferrule 150.

A patch may be placed between tether 110 and helical anchor 130. Patch 140, in one embodiment, has a diameter greater than a width (diameter) of helical anchor 130. Patch 140 may be used as a twist or screw stop to indicate to a physician or other operator inserting tether 110 into a wall of ventricle, a stopping point for insertion. Alternatively, a torquing device (e.g., torque wrench) may be connected by an operator at a proximal end of a catheter and connected to tether 110. The torquing device may be set to indicate a stopping point for insertion of helical anchor 130 into a wall of a ventricle. Patch 140, when positioned, is, in one embodiment, designed to be within a ventricle (e.g., left ventricle). Patch 140 may also be configured to promote healing, through tissue incorporation into a porous body of patch 140 or a bioactive coating on patch 140.

FIG. 1B shows an embodiment of a portion of apparatus 100 deployed in a tissue, for example, a wall of a ventricle or papillary muscle(s). FIG. 1B shows a distal portion of tether 110, helical anchor 130 and patch 140. In this embodiment, helical anchor 130 is axially deployed (identified by axis 195) in the tissue, for example, by twisting the anchor into tissue 190.

Figure 1C:
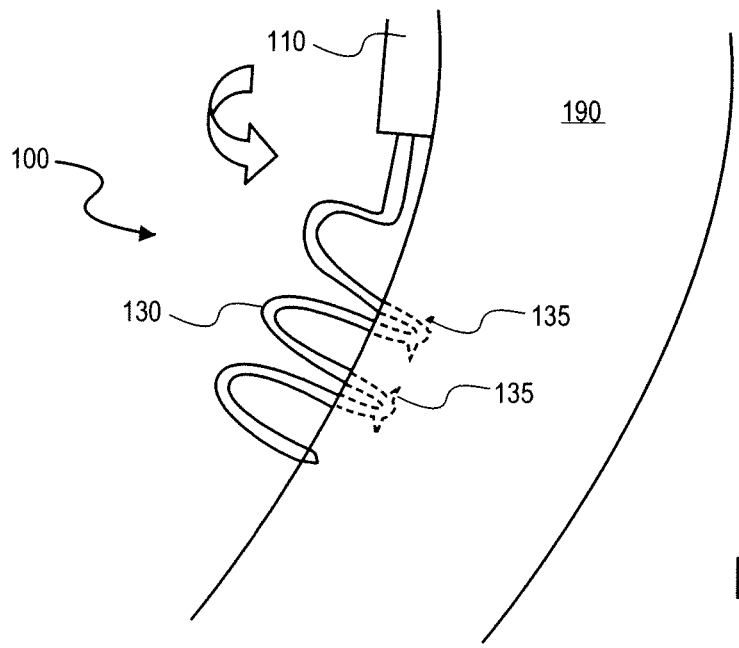
FIG. 1C shows a magnified view of a distal portion of the apparatus of FIG. 1A deployed in a tissue according to a second embodiment.

FIG. 1C shows another embodiment of a portion of apparatus 100 deployed in a tissue, for example, a wall of a ventricle or a papillary muscle(s). In this embodiment, helical anchor 130 is connected to tissue 190 along a side portion of helical anchor 130 (e.g., laterally connected). In one embodiment, helical anchor 130 includes a number of helical loops of similar diameter. Helical anchors having a similar configurations are described in U.S. Pat. No. 5,810,882. Representatively, a distal end of helical coil 130 may puncture the tissue on initial deployment. As helical coil 130 is rotated, the distal end exists the tissue at a point other than the initial puncture point, thus capturing a portion of the tissue with a portion of the initial loop of helical anchor 130. Additional twisting will cause the distal end of helical coil 130 to re-enter the tissue at a different point. Continued twisting deploys (connects) multiple loops of helical 130 to tissue 190. Using several puncturing turns (loops of helical anchor 130) tends to distribute any tearing force over several puncture points to make tearing less likely. In another embodiment, at least the side of one or more loops of helical anchor 130 may include barbs 135 that may assist in securing helical anchor 130 in tissue 190. Also in this embodiment, a patch (e.g., patch 140) may not be necessary.

Figure 1D:
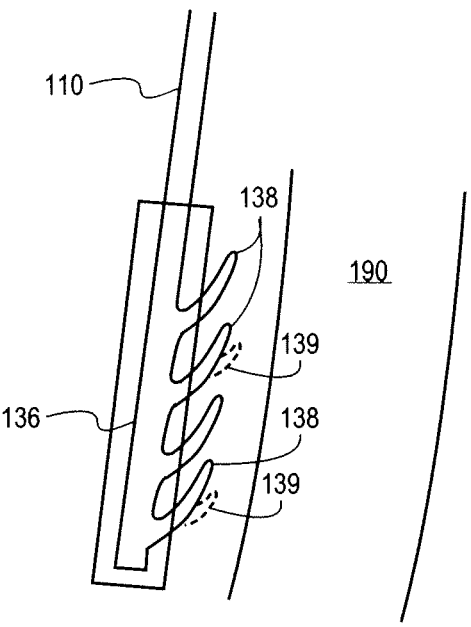
FIG. 1D shows a magnified view of a distal portion of an apparatus similar to the apparatus of FIG. 1A and having a plurality of hooks to connect to a tissue according to a third embodiment.

In another embodiment, apparatus 100 may be secured to a tissue, for example, a wall of a ventricle or a papillary muscle (s) by hooks. The hooks may be connected to or a portion of a distal segment of tether 110. Tether 110, in one embodiment, may not need to be designed to resist torsion. FIG. 1D shows distal end of tether 110 including hook portion 136 with a number of hooks 138 and possibly barbs (e.g., barbs 139 on hooks 138). In this view, hook portion 136 is adjacent tissue 190 (e.g., a ventricle wall or a papillary muscle). Hook portion 136 is covered, in one embodiment, by patch 140 so that only hooks 138 are exposed.

Figure 1E:
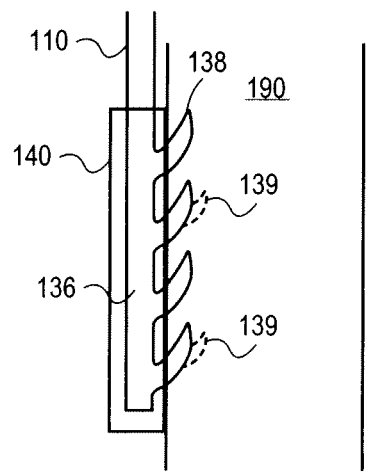
FIG. 1E shows the portion of the apparatus of FIG. 1D connected to a tissue.

To deploy hook portion 136 in tissue 190, hooks 138 may be pressed against tissue 190 and set with a proximal pulling (tension) on tether 110. FIG. 1E shows hook portion 136 deployed in tissue 190.

In one embodiment, apparatus 100 is suitable for residence in the left atrium and ventricle of a heart. It is generally recognized that thrombosis or clotting caused by foreign materials is particularly significant on the left side of the heart. Although clots from foreign articles may form on either side of the heart, clots on the left side tend to be problematic in their ultimate effect. In some situations, of course, articles must be placed on the left side of the heart that have a potential to induce thrombosis. To reduce the risk of problems, patients with such articles often are required to take an anti-thrombotic medication, potentially for the rest of their lives. Therefore, articles placed on the left side of the heart generally seek to reduce the potential for thrombosis or clot formation. In one embodiment, therefore, it is preferred that blood contact surfaces of apparatus 100 be made of non-thrombogenic or less thrombogenic materials. One material that is suitable as tending to inhibit thrombosis is a treated tissue such as porcine tissue. A treated tissue is generally a tissue including the connective tissue matrix with the cells of the tissue removed. Thus, the connective tissue web when placed within, for example, the left side of the heart provides an area for cell growth within the matrix or web. The tissue can undergo endothelialization which inhibits thrombosis.

In addition to modified tissue, certain artificial materials are similarly suitable as materials that inhibit or reduce the tendency for thrombosis. Suitable materials include, but are not limited to, woven polymers, including but not limited to, expanded polytetrafluoroethylene (ePTFE) or GORTEX™ (a registered trademark of W.L. Gore & Associates, Inc. of Wilmington, Del.), woven DACRON™ (polyethylene terephthalate) (DACRON™ is a registered trademark of E.I. duPont de Nemours and Company of Wilmington, Del.), and certain high density polyethylenes (HDPE). One type of expanded high density polyethylenes (eHDPEs) suitable as a material that inhibits thrombosis is described in commonly-assigned U.S. patent application Ser. No. 10/174,073, titled "Porous Polymer Articles and Methods of Making the Same," filed Jun. 17, 2002. Expanded HDPEs have a node and fibril microstructure allowing cells to take up residence within the node and fibril microstructure to encourage or promote endothelialization.

In one embodiment, it is desired that materials for apparatus 100 that are exposed to blood, particularly on the left side of a heart, such as a material for sheath 117 of tether 110, patch 140, aptation device 120, and any distal anchor portion exposed in the ventricle are a material that does not promote or inhibits thrombosis (e.g., non-thrombogenic or less thrombogenic). Alternatively or additionally, the surface of one or more materials for apparatus 100 may be modified (e.g., treated to reduce its/their thombogenicity). Other materials such as silicone (e.g., poly(dimethyl siloxane))) may be used for the exposed materials. However, it is appreciated that the use of such material may also require a regimen of anticoagulation drugs for a patient having apparatus 100 placed in the left side of his or her heart. Another alternative embodiment is to coat blood contact surfaces of apparatus 100 with a material that reduces its thrombogenicity or incorporate bioactive drugs/materials into the material to encourage endothelialization and/or to reduce thrombogenicity.

As noted above, in one embodiment, tether 110 shown in FIG. 1A is adapted to be twisted (screwed) into a wall of a ventricle or a papillary muscle(s). Referring to FIG. 1A, a proximal side of apparatus 100 includes threaded stud 160 to receive, for example, a female mate extending to a proximal end of a catheter to transmit the rotation of the catheter or an instrument within the catheter to apparatus 100. In one embodiment, stud 160 is connected to duplex spring 115 of tether 110 through crimp ferrule 165. In one embodiment, stud 160 is adapted to be placed on a right side of the heart, for example, through the interatrial septum. Therefore, concerns regarding thrombosis of the material for stud 160 are not as pronounced. Material for stud 160 includes, but is not limited to, a stainless steel material or a hard plastic such as an acetal.

Connected to tether 110 in the embodiment shown in FIG. 1A is aptation device 120. Aptation device 120, in this embodiment, includes a cylindrical body connected to the tether at a position on the tether corresponding to a position between cusps or leaflets of an atrioventricular valve when the tether is positioned through the valve and connected to the ventricle. In one embodiment suitable for mitral valve modification, a proximal end of aptation device 120 is located five to 10 centimeters from a distal end of tether 110. In one embodiment, aptation device 120 has a size that is suitable, that when placed between cusps or leaflets of an atrioventricular valve (e.g., a mitral valve), the cusps or leaflets of the valve will aptate against the aptation device. Representative lengths on the order of one to three centimeters are suitable but other lengths may be used depending on the requirements of a particular patient. In one embodiment, in terms of a length dimension, the aptation device 120 has a length suitable such that when the atrioventricular valve is closed, half of the exposed length of aptation device 120 resides in the atrium and half in the ventricle. In terms of a diameter for a cylindrical embodiment of aptation device, a diameter that will minimize regurgitation through an atrioventricular valve by providing surface area at the closing point of the valve is suitable. Representative suitable diameters include, but are not limited to, on the order of 0.5 to 2 centimeters.

As noted above, one purpose of aptation device is to provide surface area at the closure point of the atrioventricular valve. Aptation device 120 is, in one embodiment, a hollow cylindrical material that is suitable for residence on the left side of the heart. Preferably, aptation device 120 is a material that resists or inhibits thrombosis, such as porcine tissue or artificial material such as ePTFE or eHDPE. Aptation device 120 is deformable in the sense that its hollow cross-section may deform in response to forces applied to it by the atrioventricular valve cusps or leaflets contacting aptation device 120 and thus may cushion the compact/impact forces of the cusps or leaflets. In one embodiment, aptation device 120 is connected to tether 110 (at connection 125) only at a proximal end of aptation device 120.

Figure 1F:
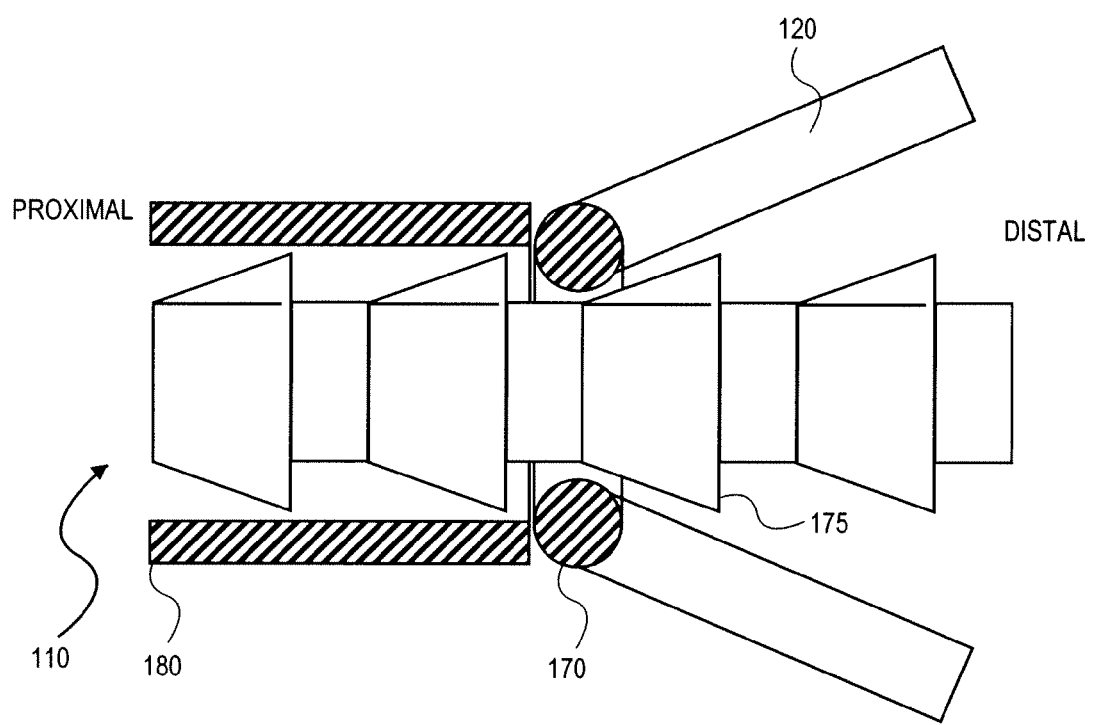
FIG. 1F shows a magnified view of a portion of one embodiment of the apparatus of FIG. 1a showing the connection between an aptation device and a tether.

FIG. 1A shows a conical section of aptation device 120 connected to tether 110 at connection 125 by an adhesive such as a silicone adhesive. Another suitable connection of aptation device 120 to tether 110 is one where the point of connection may be modified to accommodate distance variations of aptation devices on tethers among, e.g., patients. FIG. 1F illustrates a magnified view of a connection between aptation device 120 and tether 110 and shows a ratchet type connection. The illustrated ratchet-type connection allows aptation device 120 to be moved distally (see FIG. 1A) during delivery but prevents aptation device 120 from moving proximally after delivery. In the embodiment shown in FIG. 1F, a proximal end of aptation device 120 includes relatively rigid ring 170 around tether 110. A portion of tether 110, in this embodiment includes relatively deformable conical/inclined features on an outside diameter (OD) of tether 110, a distal base of which are larger in diameter than an inner diameter (ID) of ring 170. Representatively, inner sheath 180 surrounding tether 110 (not shown in FIG. 1A) may be included at delivery to maneuver (e.g., push) aptation device 120. For example, aptation device 120 would be delivered in a proximal position and inner sheath 180 extending, for example, to a proximal end of the catheter would be used to push aptation device 120 distally into position (e.g., an operator pushing on a proximal end of inner sheath 180) either prior to or after aptation device 120 had been deployed (see FIGS. 2-7).

In one embodiment, aptation device 120 has sufficient structural integrity to be folded within a catheter sheath suitable for percutaneous delivery and to adopt a desired shape when deployed. Aptation device 120 may therefore include, necessary or desired, structural support. FIG. 1A shows longitudinally extending structural support members 128 and circumferentially disposed structural support member 129 embedded in or otherwise providing a framework for aptation device 120. Suitable material for structural support members 128 and 129 include metals such as, but not limited to, nickel-titanium (NiTi) alloys that may have, where necessary, a shape memory and/or superelastic property to adopt a desired shape when deployed from a catheter sheath. Structures, material, and processes similar to those used in the manufacturing of self-expanding stents may be adapted to create a support member (e.g., support member 128 and/or support member 129) that provides a desired shape and resilience for aptation device 120. Other superelastic materials (e.g., metals) and/or metals, elastic and/or polymer reinforcement materials may also be utilized. In the embodiment of aptation device 120 shown in FIG. 1F, ring 170 may be structural material such as described with reference to support member 128 and support member 129.

Figure 2A:
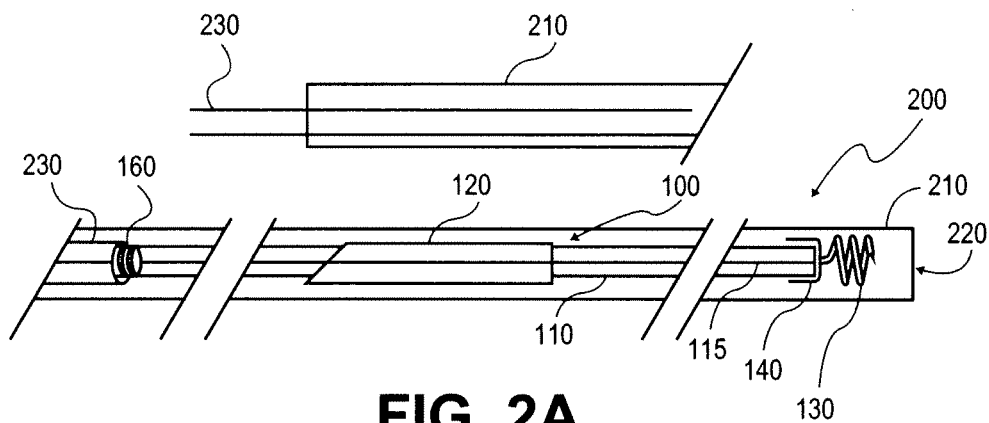
FIG. 2A shows the apparatus of FIG. 1A confined in a catheter sheath.

As noted above, in one embodiment, the apparatus suitable for modifying the cusps or leaflets of an atrioventricular valve is also suitable to be inserted percutaneously. FIG. 2A representatively shows apparatus 100 disposed within a catheter lumen. In the embodiment shown, catheter 200 includes catheter sheath 210 having a lumen therethrough of a diameter sufficient to encompass apparatus 100 of tether 110 and aptation device 120. In one embodiment, aptation device 120 is folded over to reduce its diameter within lumen 220. As illustrated in FIG. 2A, the inner diameter of lumen 220 may be of a size that is smaller than the diameter of patch 140 at the distal end of apparatus 100. Patch 140 is also folded inward (in a proximal direction) to decrease the profile of apparatus 100 within catheter sheath 210. Aptation device 120 may also be collapsed. Patch 140 may also be collapsed as well as patch 140 may have a support structure (like aptation device 120). One property of an expanded polymer (e.g., ePTFE, eHDPE) is that it can be collapsed. Collapsed, in this sense, means the fibrils are deformed (e.g., placed in compression or bent) such that the distance between the nodes is reduced. This allows the aptation device and/or patch to have its dimensions reduced without folding or to reduce the amount of folding required. When deployed, the fibrils are straightened (placed in tension). It takes little force to keep the fibrils collapsed, to straighten them or to bend them, but a much larger force to stretch the fibrils (having a much larger cross-section, the nodes deform much less than the fibrils, so the bulk of any deformation is confined to the fibrils). Thus the devices are flexible when collapsed and take little force to expand back to size, but when deployed the expanded polymer "skin" may be taut but is still a relatively soft/low friction skin which provides less cusp or leaflet abrasion. The relatively low friction characteristics of materials such as ePTFE, eHDPE also aid in the deployment because they create little resistance to withdrawing catheter sheath 210.

FIG. 2A also shows stud 160 at the proximal end of tether 110. Stud 160, in this embodiment, is mated, such as by a threaded connection, to shaft 230 that extends to a proximal end of catheter 200. Shaft 230 may, in addition to providing a mating receptacle for stud 160, be composed of a duplex spring or other structure to allow a torque to be applied at a proximal end of catheter 200 and deliver a similar response to tether 110. Catheter sheath 210 may be sized to fit within a multi-lumen catheter (catheter 200), a guide catheter (not shown) and/or a deflecting catheter (not shown) or deflecting guide. A representative outside diameter (OD) for catheter sheath 210 is on the order of 0.060 inches to 0.250 inches. Additional lumens of a multi-lumen catheter may be used, for example, insertion of a guiding apparatus (e.g., guidewire) or visualization device.

Figure 2B:
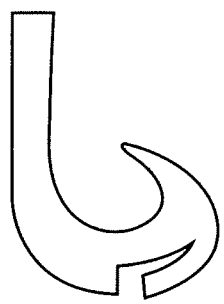
FIG. 2B shows an embodiment of a distal hook portion of an embodiment of an apparatus such as the apparatus of FIG. 1A where the hook portion is in a collapsed (or partially collapsed) state.
Figure 2C:
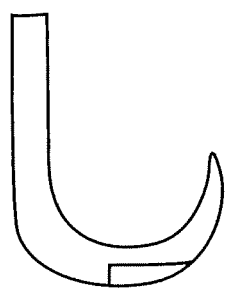
FIG. 2C shows a hook portion is in a deployed state.

In the embodiment, shown in FIG. 2A, apparatus 100 includes helical anchor 130 sized to fit within catheter sheath 210. Where a distal anchor is a number of hooks (such as illustrated in FIG. 1D and FIG. 1E), the hooks may be made, if necessary in such a way that they are collapsed in a catheter sheath and expand/deploy when the catheter sheath is withdrawn. One way that a hook may be collapsible is by forming it of flexing/spring-like materials, such as stainless steel and nitinol. Additionally, the base curve of the hook may include a mechanical design that permits a collapse in the sheath, but resists the further flexing of the hook once deployed. FIGS. 2B-2C illustrate an example of a hook that is mechanically collapsible. FIG. 2B shows hook 230 in a collapsed state and FIG. 2C shows hook 230 in a deployed configuration.

To deliver catheter 200 and apparatus 100 into the left ventricle of left atrium of a heart, standard catheter procedures may be followed. For instance, a guidewire may first be inserted via the femoral or jugular artery. The guidewire (and possibly a guide catheter) may be advanced through the aortic arch and into the left ventricle and across the mitral valve. In another embodiment, the catheter may be delivered via a vein into the right atrium and cross to the left atrium, by a transeptal approach. One way this may be accomplished is by puncturing the fossa ovalis, a thin-walled structure between the right and left atriums (in adults). The fossil ovalis may be punctured and the left atrium accessed using the methods and tools currently used for this purpose, e.g., for percutaneous atrial ablation to prevent or reverse atrial fibrillation. Such a puncture may be performed or followed by a guidewire or guidewire-like device that may then provide a path for a guiding catheter, a deflecting guide, a device delivery catheter, and the like, as in other percutaneous procedures.

Figure 3:
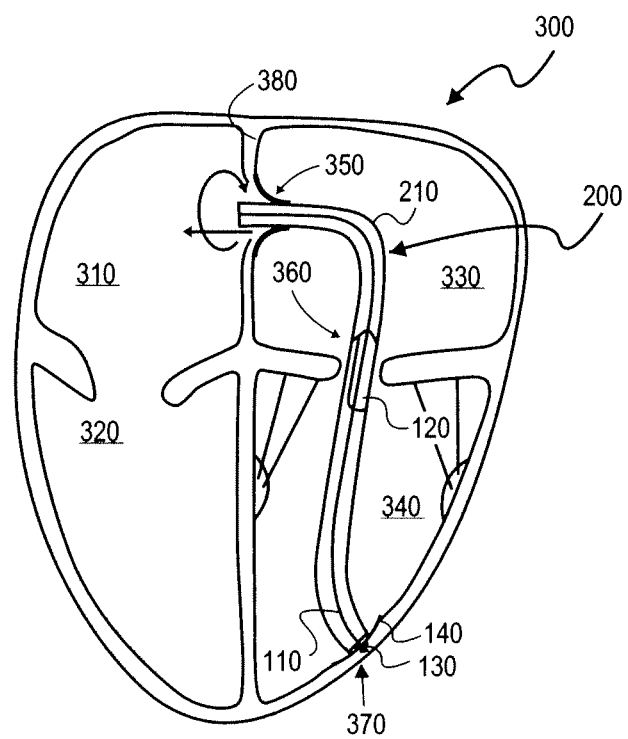
FIG. 3 shows a schematic, cross-sectional front view of a heart with the apparatus of FIG. 1A (in a catheter) positioned within a left atrium and ventricle of a heart and shows fastening of the apparatus to a wall ventricle.

FIG. 3 is a simplified schematic representation of a front side view of a heart showing right atrium 310, right ventricle 320, left atrium 330 and left ventricle 340. FIG. 3 also shows heart 300 having catheter 200 inserted through fossa ovalis 350 and through mitral valve 360. Catheter 200, in this representation, may be advanced until catheter 200 contacts a portion of a wall of left ventricle 340, such as the apex of the ventricle. Imaging techniques, including, but not limited to, fluoroscopy or ultrasound, may be used to place catheter 200. Accordingly, in one embodiment, sheath 117 and/or aptation device may include visualization markers embedded therein or coated thereon (e.g., radiopaque markers).

FIG. 3 shows a portion of catheter 200 including tether 110 and aptation device 120 of apparatus 100 therein advanced through right atrium 310, through fossa ovalis 350 into left atrium 330, through mitral valve 360, and connected to a wall of left ventricle 340 at point 370. In one embodiment, point 370 is a location directly below mitral valve 360 at the apex of left ventricle 340. FIG. 3 also shows a mechanism of connecting apparatus 100 at point 370 of left ventricle 340. FIG. 3 shows helical anchor 130 connected to the wall of left ventricle 340 at point 370. One way helical anchor 130 is connected to a wall of ventricle 330 is by contacting a wall of left ventricle 340 at point 370 with catheter 200 and pulling back catheter sheath 210 from a proximal end of catheter 200. Catheter 200 is then twisted, such as twisted clockwise, to advance helical anchor 130 into the tissue. In one embodiment, catheter sheath 210 is retracted to expose helical anchor 130 and patch 140. Catheter 200 is twisted until helical anchor 130 is advanced into the wall of left ventricle 340 a distance such that patch 140 contacts the wall of left ventricle 340. The contacting of the wall creates an additional resistance in twisting that an operator (e.g., physician) will be able to sense to know that a stopping point has been reached. Alternatively, shaft 230 may be connected to a torquing device (e.g., torque limiting driver) at a proximal end of catheter 200. When a predetermined torque is applied by an operator (e.g., physician), helical anchor 130 is set in the wall of left ventricle 340.

FIG. 3 shows heart 300 with tether 110 connected at a distal end to a wall of left ventricle 340 by helical anchor 130 with patch 140 opened and contacting the wall of left ventricle 340. FIG. 3 also shows catheter sheath 210 of catheter 200 removed from the distal portion of apparatus 100. Once helical anchor 130 is set in a wall of left ventricle 340, catheter sheath 210 is retracted out of left ventricle 340. As catheter sheath 210 is further removed to expose more of apparatus 100, aptation device 120 is exposed. As shown in FIG. 3, aptation device 120 of a generally cylindrical structure is located within mitral valve 360. In one embodiment, approximately half of the cylindrical body of aptation device 120 is located in left atrium 330 and approximately half in left ventricle 340 when cusps or leaflets of mitral valve 360 aptate against aptation device 120 during, for example, systole.

Figure 4:
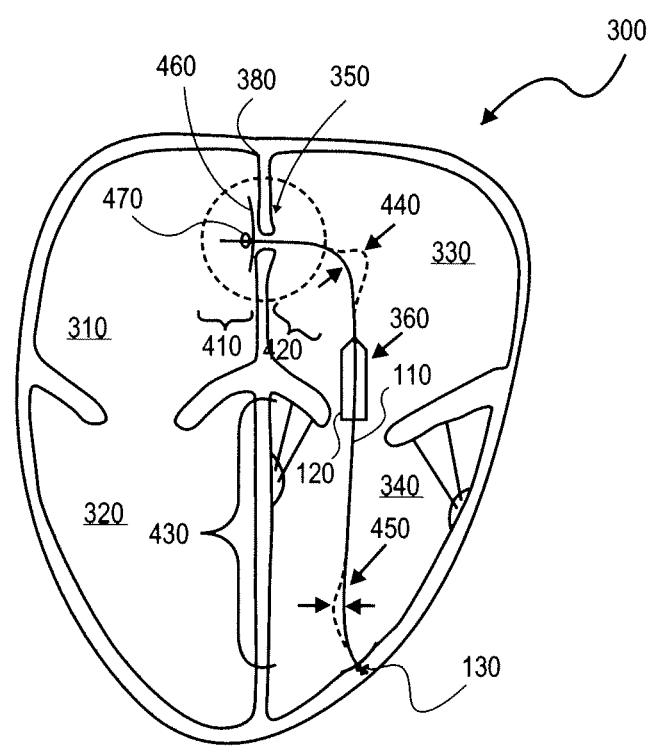
FIG. 4 shows the heart structure of FIG. 3 and the apparatus of FIG. 1 following the removal of a catheter sheath from the apparatus and deployment of a proximal patch at the interatrial septum.

FIG. 4 shows heart 300 having apparatus 100 placed in left atrium 330 and left ventricle 340 and connected to left ventricle 340 and to interatrial septum 380. In this view, aptation device 120 is connected to tether 110 and is shown deployed within mitral valve 360. As viewed, mitral valve 360 is open and the cusps or leaflets of mitral valve 360 are not closed or aptated against aptation device 120. Thus, aptation device 120 adopts, when removed from catheter sheath 210 a cylindrical shape. In one embodiment, the shape may be deformed when the cusps or leaflets of mitral valve 360 close against aptation device 120.

FIG. 4 also shows the flexural support characteristics of tether 110 in left atrium 330 and left ventricle 340. As viewed, that portion of tether 110 in left atrium 330 has a flexural play indicated by play 440 while that portion of tether 110 in left ventricle 340 has play 450. In one embodiment, the play in left ventricle 340 (play 450) is less relative to play in left atrium 330 (play 440). By minimizing the amount of play 450 of the tether 110 in left ventricle 340, the location of aptation device 120, relative to mitral valve 360 is controlled. Ideally, play 450 is minimized or is absent in tether 110 within left ventricle 340. Play 440 of tether 110 in left atrium 330, by contrast can be present to allow aptation device 120 to float into position between cusps and leaflets of mitral valve 360.

FIG. 4 indicates three portions of tether 110. Proximal portion 410 is disposed in right atrium 310. Medial portion 420 is disposed in left atrium 330. Distal portion 430 is disposed in left ventricle 340. FIG. 4 also shows the connecting of tether 110 to interatrial septum 380. In one embodiment, proximal portion 410 of tether 110 extends into right atrium 310. In this manner, concerns of materials such as stud 160, used, for example, to connect tether 110 to a torquing device are not as pronounced on the right side of the heart as they are on the left side. Nevertheless, materials should still be selected that limit the formation of thrombosis, even on the right side of the heart. On the right side, the consequences of minor thrombotic emboli are relatively minor, compared to the strokes that such emboli can cause on the left side. However, large emboli in the right side of the heart can cause pulmonary embolism (PE).

Figure 5A:
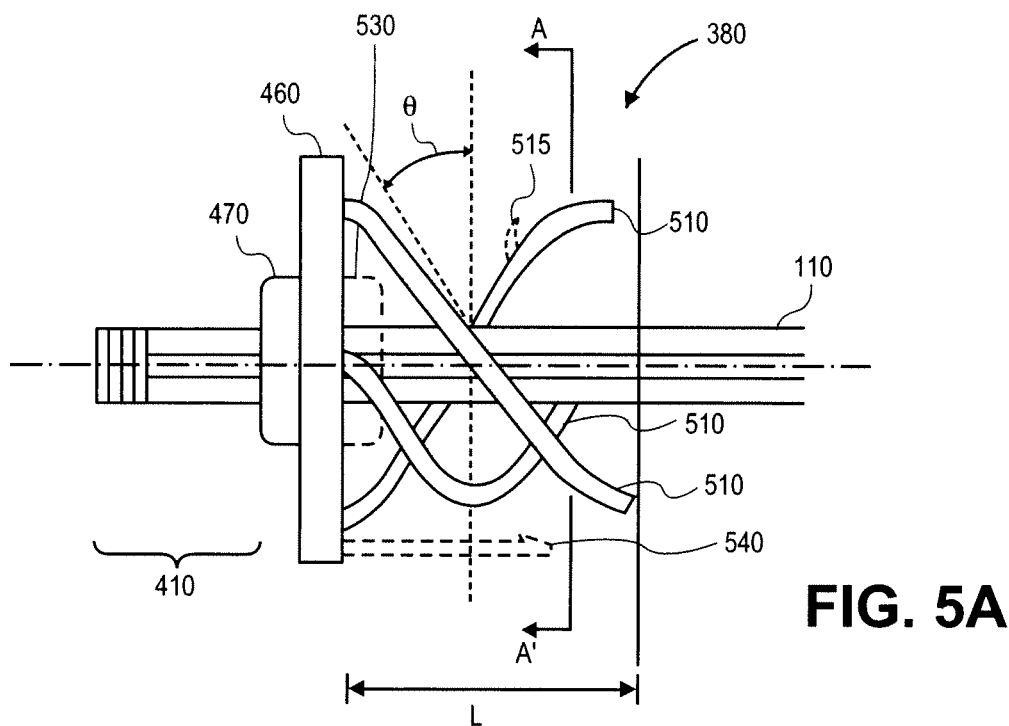
FIG. 5A is a close-up schematic view of a proximal portion of the apparatus of FIG. 4 shown fixed to the interatrial septum of FIG. 4.

To maintain proximal portion 410 of tether 110 in right atrium 310 and medial portion 420 in left atrium 330, tether 110 is connected about interatrial septum 380. One way this is accomplished is shown in FIG. 5A.

Connected to proximal portion 410 of tether 110 is patch 460. Patch 460 is positioned on tether 110 to abut a proximal side (right atrium side) of interatrial septum 380. Proximal to patch 460 is raised bump 470 to hold patch 460 in position against a proximal side (right atrium side) of interatrial septum 380. Patch 460 inhibits the movement of tether 110, once positioned, into left atrium 330. In one embodiment, patch 460 is a material selected to be collapsed or folded onto tether 110 when apparatus 100 is disposed within a catheter sheath and percutaneously positioned within the heart. Patch 460 is also selected, in one embodiment, to have sufficient structural strength to hold tether 110 in position against a proximal side (right atrium side) of interatrial septum 380. A suitable material is, for example, ePTFE, eHDPE, or a DACRON™ material possibly with support structures similar to support structures in aptation device 120. Patch 460 may also be configured to promote healing, through tissue incorporation into a porous body of patch 460 or a bioactive coating on patch 460. In one embodiment, patch 460 has a diameter larger than an outside diameter of tether 110 and sufficient to cover any opening around tether 110 through interatrial septum 380.

Raised bump 470 is connected to a proximal side of patch 460. In one embodiment, raised bump 470 surrounds a portion, including the entire portion, of tether 110. Raised bump 470 is of a size suitable to maintain patch 460 in position (e.g., greater than a cross-sectional opening of patch 460 around tether 110). Raised bump 470 may be selected from various materials suitable to be placed on a right side of the heart and bond, possibly through an adhesive, to a material selected for tether sheath 117. Suitable materials include, but are not limited to, polymers and metals (e.g., a stainless steel band).

Figure 5B:
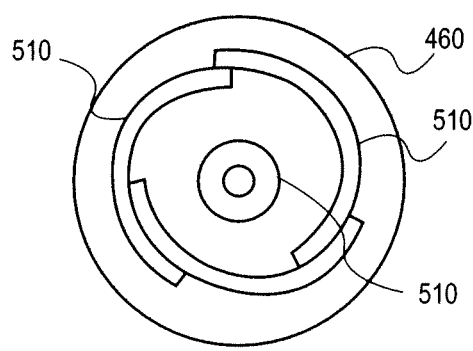
FIG. 5B shows a view of the apparatus of FIG. 5A through line A-A'.

In one embodiment, tether 110, in addition to being fixed on a proximal side of interatrial septum 380, is also fixed to interatrial septum 380 to prevent movement of tether 110, once fixed, into right atrium 310. Referring to FIG. 5A, in one embodiment, one or more spring screws 510 is/are connected to a distal side of patch 460. In one embodiment, three or more spring screws 510 are connected to a distal side of patch 460 (three shown), distributed at, for example, equal angles relative to one another and equally distributed around where tether 110 goes through patch 460. Spring screws 510 are selected, in one embodiment, to have a length, L, corresponding to a portion, including the entire portion of the thickness of interatrial septum 380. Spring screw 510 should also have a diameter greater than a diameter of tether 110 and may have less than one turn. In one embodiment, spring screws 510 are connected at an outer radial point of patch 460 and circle around tether 110. FIG. 5B shows a view of the apparatus of FIG. 5A from line A-A'.

Spring screws 510 are configured, in one embodiment, to be set in interatrial septum 380 by a twist action. Representatively, spring screws 510 are configured to have a wind angle, θ, representatively on the order of 30° and higher, for example on the order of 60° to 70°. In general, the higher the wind angle, θ, the less rotation occurs and the more push force in a distal direction is translated into a twisting force. To locate spring screw 510 in interatrial septum 380, patch 460 and/or bump 470 is pushed in a direction toward left atrium 330 (e.g., a distal direction) by the sheath or a guide to locate spring screws 510 on a proximal side of interatrial septum 380. The pushing of spring screws 510 causes it to twist into the septum tissue in a cork screw fashion. With equally spaced spring screws 510 (e.g., three or more), prior to and during pushing of/on patch 460 and/or bump 470, the points of multiple spring screws 510 will contact interatrial septum 380 at multiple points (e.g., three or more points) and be supported at the proper angle relative to the septum (e.g., will not bend/tip tether 110 during pushing) and the force applied to each of them will be relatively similar. One or more spring screws 510 may include one or more protruding barbs 515. Patch 460 may be free to rotate relative to tether 110 with its position confined by bump 470 and/or raised bump 530 (described below).

In addition to or as an alternative to spring screws 510, tether 110 may be fixed at interatrial septum 380 by raised bump 530 (shown in FIG. 5A ghost lines). Raised bump 530 is located on and around a portion, including the entire portion, of tether 110 at a position distal to patch 460. Raised bump 530 may be similar in size and to raised bump 470 on a proximal side of patch 460. In one embodiment, raised bump 530 has a dimension such that it may be embedded in a portion of interatrial septum 380 (e.g., in a fossa ovalis valve) to allow a distal side of patch 460 to be seated against interatrial septum 380.

As an alternative to one or more spring screws 510 and/or raised bump 530, a distal side of patch 460 may include a number of protruding barbs 540 (shown in ghost lines). Barbs 540 are of a dimension (e.g., length) suitable for embedding in interatrial septum 380. Barbs 540 serve in one aspect to connect patch 460 to interatrial septum 380. In one embodiment, patch 460 need not be rotationally free of tether 110 when one or more barbs 540 is/are employed.

Figure 5C:
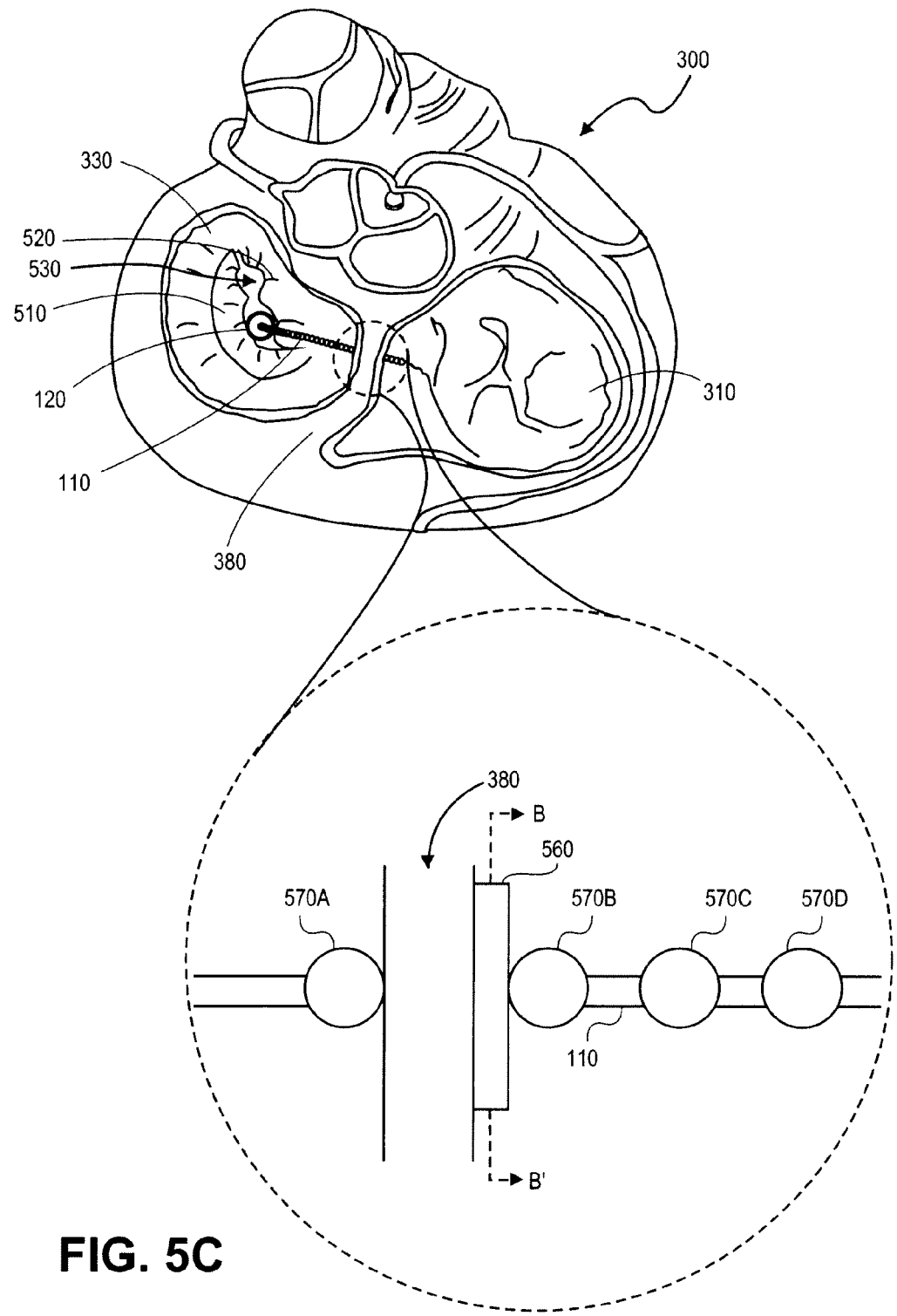
FIG. 5C shows a top perspective cross-section of a heart and shows an apparatus positioned in the left atrium and mitral valve.

FIG. 5C shows an embodiment of heart 300 through a top cross section. The view shows right atrium 310 and left atrium 330. In left atrium is cusp or leaflet 510 and cusp or leaflet 520 of a mitral valve. The mitral valve is shown open (opening 530).

Disposed between cusp or leaflet 510 and cusp or leaflet 520 in FIG. 5B is apparatus 100 including tether 110 and aptation device 120. A proximal end of tether 380 is connected to interatrial septum 380.

As can be seen in FIG. 5C, opening 530 between cusp or leaflet 510 and cusp or leaflet 520 extends approximately laterally across a portion of left atrium 330. In one embodiment, aptation device 120 is sized so that it occupies only a portion of opening 530 between cusp or leaflet 510 and cusp or leaflet 520 (see FIG. 5C). Representatively, regurgitation through a mitral valve may not occur along the entire closure or aptation line between cusp or leaflet 510 and cusp or leaflet 520 but only at a point or region along the closure or aptation line. In other words, with mitral regurgitation, the valve cusps or leaflets usually close normally against each other, except in a small region. Apparatus 100 may be adjusted so that aptation device 120 is positioned between cusps or leaflets 510 and 520 at a point of the closure or aptation line where regurgitation is noted or potential regurgitation is noted. In such manner, aptation device 120 may be sized to be large enough (e.g., diameter) only to inhibit the regurgitation. Thus, aptation device may have a reduced cross-sectional area that has the advantages of easier delivery, generates less tether forces on the distal anchor, and interferes less with the inflow of blood into the ventricle during diastole.

One way to selectively place aptation device of apparatus 100 at a point or region of the closure or aptation line of cusp or leaflet 510 and cusp or leaflet 520 is by adjusting tether 110 to position aptation device 120 toward or away from interatrial septum 380. FIG. 5C illustrates an embodiment where the length of tether 110 in, for example, left atrium 330 may be adjusted. The inset of FIG. 5C shows tether 110 having a series of raised bumps 570A, 570B, 570C, and 570D along its length at a proximal end. Raised bumps 570A, 570B, 570C and 570D have an outside diameter greater than the diameter of tether 110. It is appreciated that there may be a number of bumps along a proximal portion of tether 110 spaced incrementally from one another and extending, collectively approximately the length of the closure or aptation line. FIG. 5C also shows diaphragm or patch 560 on a proximal side (right atrium side). Diaphragm 560 may be similar to patch 460 described above and may be deployed percutaneously by collapsing (e.g., folding) in a catheter sheath and removing/retracting the sheath at a delivery site. Diaphragm 560 has a size and an opening therethrough such that a raised bump (raised bump 570A, 570B, 570C, or 570D) placed proximal to diaphragm 560 is inhibited from moving distally toward left atrium 330 without an external force such as a pushing force by an operator. Similarly, a raised bump placed distal to diaphragm 560 is inhibited from moving proximally toward right atrium 310 without an external force such as pulling by an operator.

Figure 5D:
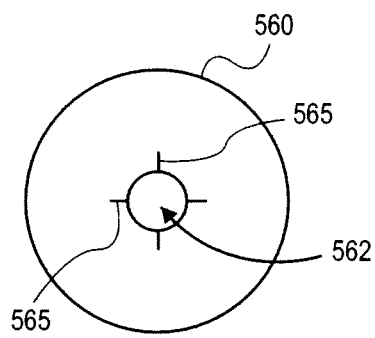
FIG. 5D shows a cross-section through line B-B' of the apparatus of FIG. 5B.

FIG. 5D shows a cross-section through line B-B' of FIG. 5C to illustrate a cross-section of diaphragm 560. In this embodiment, diaphragm 560 has central opening 562 to accommodate tether 110. Diaphragm 560 also has a number of slits 565 extending from opening 562 that serve to increase the diameter of opening 562 in response to pushing/pulling larger diameter objects, such as bumps 570A, 570B, 570C, and 570D, through opening 562.

Figure 5E:
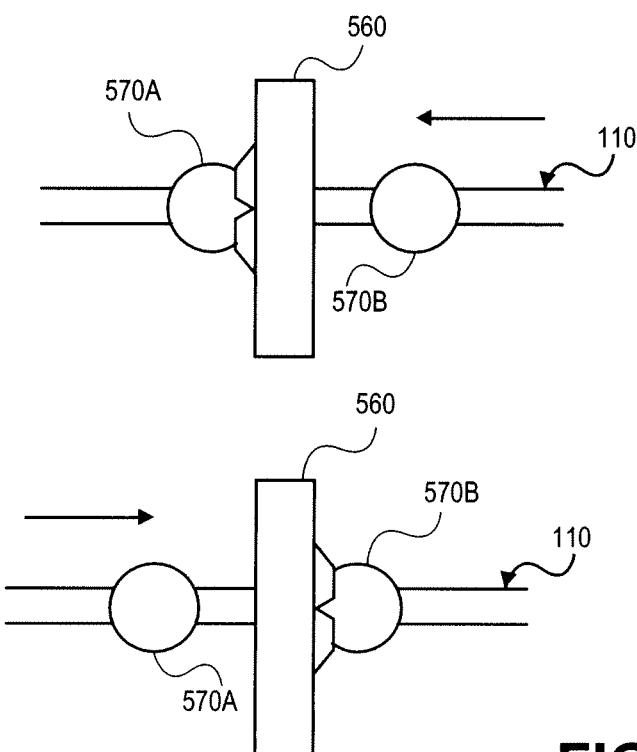
FIG. 5E shows a portion of the tether of the apparatus of FIG. 5B illustrating the movement of the tether.

FIG. 5E shows tether 110 including bump 570A and bump 570B. FIG. 5E also shows diaphragm 560 connected to tether 110. In this embodiment, tether 110 may allow bumps to be moved in either direction during the delivery procedure. Once diaphragm 560 has been deployed on a proximal side (e.g., right atrium side) of interatrial septum 380, the size of diaphragm 560 inhibits it from being easily pushed through septum 380 by forces generated, for example, on tether 110 and moving bumps 570A and 570B through diaphragm 560.

For a pulling force on tether 110, a sheath used to percutaneously deliver the apparatus (e.g., sheath 210 in FIG. 2A) may be retracted to deploy diaphragm 560 then advanced to hold diaphragm 560 in place against interatrial septum 380 while bumps (e.g., bumps 570A and 570B) are moved through diaphragm 560.

Bumps may pass in either direction through diaphragm 560 with the application of a small force. This allows the operator to locate the device to achieve the best result (e.g., minimize regurgitation). The required force to effect movement can be modified by the design/materials used. Tissue ingrowth should seal any small gaps after deployment.

Using the embodiment illustrated in FIG. 5C, to position aptation device 120 at a point or region along the closure or aptation line, an operator could, starting, for example, with aptation device 120 between cusp or leaflet 510 and cusp or leaflet 520 at a distal end of the closure or aptation line relative to interatrial septum 380, pull tether 110 toward right atrium 310 until aptation device 120 is at a desired point. By increasing the number of raised bumps (e.g., raised bumps 570A, 570B, 570C, and 570D), and decreasing the spacing between the bumps, the accuracy of positioning of aptation device 120 may be increased.

In certain of the above paragraphs, attention has focused on connecting apparatus 100, including tether 110 and aptation device 120, principally within left atrium 330 and left ventricle 340. One consideration in connection with an apparatus such as apparatus 100 within the left side of a heart, is the amount of pressure or force that the apparatus will see in the operation (e.g., contracting) of the heart. Referring to tether 110 of apparatus 100, in general, distal portion 430 sees a significantly greater force during the operation of a heart than medial portion 420 (see FIG. 4). This additional force is due, in one aspect, to the force created by filling left ventricle 340 with blood and discharging the blood. Therefore, in general, aspects concerned with connecting (tethering) tether 110 to left ventricle 340 may generally be more pronounced than connecting tether 110 at interatrial septum 380.

FIGS. 6-8 schematically illustrate the function of apparatus 100, specifically aptation device 120 with respect to mitral valve aptation. FIG. 6 shows aptation device 120 connected to tether 110 and positioned within mitral valve 360. In this embodiment, aptation device 120 is generally cylindrical and connected to tether 110 at a superior portion (as viewed) of aptation device 120. In one embodiment, aptation device 120 is generally hollow and its inferior portion (as viewed) is open.

FIG. 6 illustrates a condition of diastole, when the heart is relaxed and left ventricle 340 is, representatively, filling with blood (indicated by arrow 605). At this point, mitral valve 360 is open and cusps or leaflets 610 and 620 do not contact (or minimally contact) aptation device 120. Aptation device 120 preferably has a dimension (e.g., diameter) that minimizes the obstruction of blood flow from left atrium 330 to left ventricle 340.

FIG. 7 illustrates a condition of systole, where left ventricle 340 contracts and sends the blood collected therein to the aorta. During or prior to systole, mitral valve 360 closes by the aptation of cusps or leaflets 610 and 620. For patients suffering a condition where cusp or leaflet 610 does not aptate with cusp or leaflet 620, aptation device 120 fills the void left between the cusps or leaflets. FIG. 7 shows cusps or leaflets 610 and 620 pushed against two sides of aptation device 120. Aptation device 120 in a sense plugs the opening (indicated by reference numeral 710) between cusp or leaflet 610 and cusp or leaflet 620. FIG. 8 illustrates a cross-sectional side view through line A-A' of FIG. 7. FIG. 8 shows cusps or leaflets 610 and 620 in a closed position with gap 710 between the cusps or leaflets.

In the above description (e.g., FIGS. 6-8), aptation device 120 was described and illustrated as a cylindrical body. It is appreciated that an aptation device may be a variety of shapes selected, in one aspect, to modify (reduce) any opening between cusps or leaflets during, for example, systole, or, in another aspect, to minimize restriction of blood flow from an atrium to a ventricle during systole. FIGS. 9-11B illustrate various embodiments of aptation devices that may be substituted for aptation device 120. FIG. 9 shows aptation device 920 that has an ellipsoidal (e.g., oval) cross-section. FIG. 9 illustrates aptation device between cusps of an atrioventricular valve (e.g., a mitral valve) during, for example, systole. An ellipsoidal cross-section may be self-oriented due to the contact pressure of the leaflets/cusps, interfere less (relative to a circular cross-section) with inflow into the left ventricle and be better adapted (relative to a circular cross-section) for leaflet closure at edges 930, where the cusps transition from aptating against aptation device 120 to aptating against each other.

FIG. 10A shows another embodiment of an aptation device. Aptation device 1020 in this embodiment has a concial body that may minimize impedance of blood flow from an atrium to a ventricle. FIG. 10B illustrates an embodiment of aptation device 1030 of a bell shape as yet another possible configuration. FIG. 10C shows yet another embodiment of aptation device 1040 having a teardrop shape.

FIG. 11A illustrates another embodiment of an aptation device suitable, in one configuration, to be connected to a tether between cusps or leaflets of an atrioventricular valve. In this embodiment, aptation device 1120 is hollow with a cylindrical or elliptical proximal end having a diameter $D_1$. Aptation device narrows toward its distal end to a diameter, $D_2$ less than diameter $D_1$. Aptation device 1120 is positioned on tether 1110 such that cusps or leaflets of an atrioventricular valve contact aptation device 1120 at approximately region 1150. Aptation device 1120 may be connected to tether 1110 by tendons or wires 1130 (e.g., two or more) connected to ring 1125 that may be connected to tether 1110 by adhesive or other connection (e.g., a ratchet-type connection).

The body of aptation device 1120 may include support or reinforcement material such as a shape memory material that maintains an open inner diameter (ID) of aptation device 1120 at, in one example, a point below region 1150 identified by line A-A'. FIG. 11B shows a cross-section of aptation device 1120 through line A-A' of FIG. 11A. Below line A-A', the body of aptation device 1120 is a flexible material that acts like a valve. Accordingly, when blood is flowing from an atrium to a ventricle, the ID of aptation device 1120 below line A-A' is open. If blood attempts, however, to flow from the ventricle to the atrium, the ID of aptation device is closed by the collapsing of the flexible material of aptation device 1120.

In another embodiment, aptation device 1120 includes a reinforcement structure (skeleton) that extends through the device including below line A-A'. Accordingly, under pressure by the reinforcement structure, the ID of aptation device 1120 below line A-A' is slightly open in a rest state. The pressure is sufficient to avoid an endothelial closure. During an event such as systole, however, the pressure applied to aptation device 1120 by cusps or leaflets of an atrioventricular valve is transmitted distally by the reinforcement structure (skeleton) to force the distal end of aptation device 1120 (the ID at the distal end) closed. It is appreciated that aptation device 1120 may close by other mechanisms besides the pressure from cusps/leaflets contacting it. For example, the rapid flow of blood up the ID of aptation device 1120 causes its ID to be at a lower pressure than its OD and, therefore, a closure force is generated (venturi effect). When the cusps/leaflets close around aptation device 1120 and the left ventricle muscle contracts at systole, the pressure in the left ventricle exceeds that of the left atrium. As a result, the ID of aptation device 1120 which communicates with the left atrium is at a lower pressure than the OD of aptation device 1120 which communicates with the left ventricle. As before, this pressure differential between the ID and the OD creates a force that tends to close aptation device 1120.

Figure 12C:
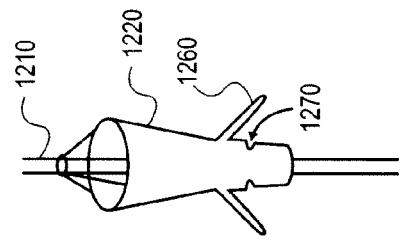
FIG. 12C shows a perspective top second side view of the apparatus of FIG. 12B.
Figure 12E:
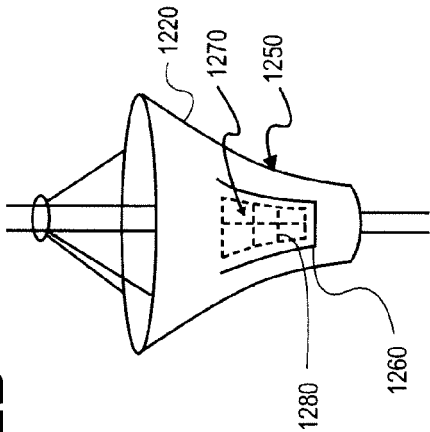
FIG. 12E shows a perspective top side view of another embodiment of a portion of an apparatus suitable for modifying an atrioventricular valve with a conical shaped aptation device.
Figure 12B:
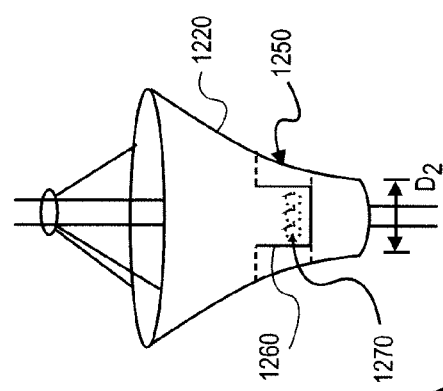
FIG. 12B shows a perspective top side view of another embodiment of a portion of an apparatus suitable for modifying an atrioventricular valve with a conical shaped aptation device.
Figure 12D:
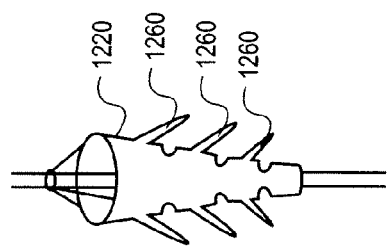
FIG. 12D shows a perspective top side view of another embodiment of a portion of an apparatus suitable for modifying an atrioventricular valve with a conical shaped aptation device.
Figure 12A:
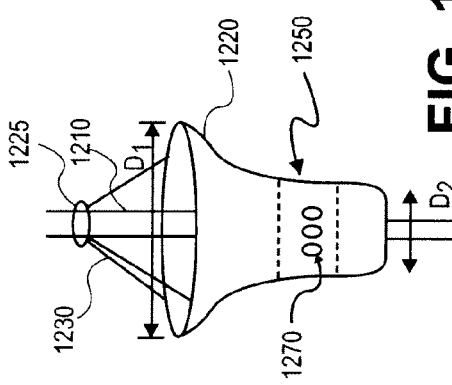
FIG. 12A shows a perspective top side view of another embodiment of a portion of an apparatus suitable for modifying an atrioventricular valve with a conical shaped aptation device.

FIG. 12A illustrates another embodiment of an aptation device. Aptation device 1220, in one embodiment, has a cylindrical or elliptical shape at a proximal end having a hollow diameter, $D_1$. Aptation device narrows toward its distal end, to a diameter, $D_2$ that is less than diameter, $D_1$. In one embodiment, the inner diameter (ID) at a distal end is substantially or completely closed. Aptation device 1220 is positioned on tether 1210 such that cusps or leaflets of an atrioventricular valve contact aptation device 1220 at approximately region 1250. Aptation device 1220 may be connected to tether 1210 by tendons or wires 1230 connected to ring 1225 that may be connected to tether 1210 by adhesive or other connection (e.g., a ratchet-type connection).

In the embodiment shown in FIG. 12A, the body of aptation device 1220 includes one or more openings (e.g., holes or slots) 1270 (three shown) into an interior of aptation device 1220. Openings 1270 allow blood to flow, for example, during diastole through an open proximal end of aptation device 1220 through openings 1270 into a ventricle. During systole, leaflets or cusps of an atrioventricular valve contact aptation device 1220 at region 1250 and cover openings 1270.

In the embodiment shown in FIG. 12B, the body of aptation device 1220 includes flaps 1260 within region 1250. In one embodiment, aptation device 1220 includes flaps equivalent to the number of cusps or leaflets of an atrioventricular valve in which aptation device 1220 will be placed (e.g., two flaps for a mitral valve). Flaps 1260 are connected to (e.g., integral with) the body of aptation device 1220 at a proximal end of the flaps. Beneath flaps 1260 in the body of aptation device 1220 are one or more openings 1270 (three shown) into an interior of aptation device 1220. Flaps 1260 allow blood to flow, for example, during diastole through an open proximal end of aptation device 1220 through openings 1270 into a ventricle. During systole, flaps 1260 are forced shut by a pressure differential between the ventricle and an atrium (or by a momentary reverse flow from the ventricle toward the atrium). In another embodiment, flaps 1260 may include a support structure that bias flaps 1260 open. The support structure of flaps 1260 may be part of any support structure (skeleton) of the main body of aptation device 1220 or may be separate from any support structure. In another embodiment, a distal end of each flap 1260 may be tethered, for example, to tether 1210 or to a ventricle.

FIG. 12C shows a side view of FIG. 12B with flaps 1260 in an open position. FIG. 12D shows an alternative configuration with multiple flaps 1260 extending longitudinally along a length of aptation device 1220 (e.g., on sides of the device intended to be positioned adjacent cusps or leaflets) and one or more openings beneath each flap. FIG. 12E shows another embodiment with a single large opening 1270 perhaps supported by reinforcement structure 1280 and flap 1260 over opening 1270.

The embodiments shown above in FIGS. 11A-12E are representative of aptation devices having open proximal ends that are suitable for use in modifying the aptation of cusps or leaflets of an atrioventricular valve. It is appreciated that modifications are possible, including closing the distal end. Representatively, openings, such as opening 1270, provide a way to minimize blood from pooling in the device (which could cause clot/emboli formation) by allowing flow through them during diastole. Flaps, such as flaps 1260 (see FIGS. 12B-12F), and/or the cusps or leaflets inhibit backflow during systole and provide increased blood flow from the atrium to the ventricle in diastole. Another alternative would be to close the proximal end of the aptation device (e.g., aptation device 1220). In this alternative flaps that open inward could be used on the device. It is also appreciated that the use of more than one of these approaches may be implemented in an aptation device to gain a more durable flow-through device outcome and reduce the resistance to blood flow from an atrium to a ventricle (e.g., during diastole).

FIG. 13 illustrates another embodiment of an apparatus suitable as an atrioventricular valve aptation device. FIG. 13 shows apparatus 1300 including support annulus 1310 and body or aptation device 1320. In one embodiment, support annulus 1310 and body 1320 are a single unitary body of, for example, a single material. Representatively, body 1320 is a relatively thin, flexible material, such as a polymer material (e.g., expanded polytetrafluoroethylene (ePTFE) or eHDPE) that may be deformed (e.g., folded, collapsed) by cusps or leaflets of an atrioventricular valve. A suitable material for support annulus 1310 and body 1320 (at least exposed or blood contact surface portions of support annulus 1310 and body 1320) is a material that will resist or inhibit thrombosis. Support annulus 1310 may be made of similar material, perhaps with additional structural integrity (e.g., thicker or supported with an additional material).

The material of support annulus 1310 and body 1320 is also suitable for being reduced in diameter (e.g., folded or collapsed) to a diameter suitable to be placed within a catheter sheath. Thus, in one embodiment, apparatus 1300 is suitable for percutaneous delivery. One percutaneous delivery approach is the transeptal approach described above with reference to apparatus 100 (e.g., FIGS. 3-4 and the accompanying text). FIG. 13 shows apparatus 1300 in a deployed configuration. As noted above, support annulus 1310 may include a reinforced body (e.g., a reinforced ring) embedded, for example, in a material that is otherwise selected for support annulus 1310 and body 1320. Representatively, a suitable reinforcement material is representatively a thin, flexible (e.g., superelastic) metal (e.g., about 0.1 to 0.2 millimeters). One suitable metal material is a nickel-titanium (NiTi) alloy having a shape memory of the deployed stage (illustrated in FIG. 13).

In one embodiment, where apparatus 1300 is selected to modify the aptation of a mitral valve, support annulus 1310 is selected to have a shape corresponding to the shape of the inner surface of the left atrium, particularly, the base of the left atrium. Representatively, the shape is circular. It is appreciated that with the contracting of a heart, the shape of the left atrium is not completely static. Accordingly, support annulus 1310 may be selected of a diameter, $D_1$, suitable to maintain its shape with contraction of a left atrium in which it is placed. A representative diameter, $D_1$, is on the order of 19 to 31 centimeters. In another embodiment, the diameter, $D_1$, and shape of support annulus 1310 is selected to conform to the shape of an atrioventricular valve annulus (e.g., a mitral valve annulus). To maintain support annulus 1310 at a location either in the atrium or an atrioventricular valve annulus, barbs 1330 extending from the exterior diameter of support annulus may be included to anchor support annulus to the tissue that makes up the atrium or atrioventricular valve annulus inner circumference.

To properly position apparatus within an atrium or atrioventricular valve annulus, support annulus 1310 (possibly body 1320) may include visualization markers included therewith (e.g., embedded therein). Suitable markers include, but are not limited to, radiopaque markers. FIG. 13 shows visualization markers 1340 around support annulus 1310.

Apparatus 1300 also includes body 1320, in this embodiment, shown as having a funnel or a conical shape from a first diameter, approximately $D_1$, to a smaller second diameter, $D_2$. Body 1320, in one embodiment, is selected to have a length, L, suitable for being deployed either in an atrium or an atrioventricular valve annulus and to extend beyond an atrioventricular valve so that the cusps or leaflets of the atrioventricular valve can contact body 1320 and collapse body 1320 onto itself upon closing. For an apparatus, such as apparatus 1300, intended to modify a mitral valve, where support annulus 1310 is intended to be anchored into the wall of an atrium, a suitable length, L, for body 1320 is on the order of 20 to 30 millimeters. Body 1320 may also include visualization markers (e.g., embedded therein).

In operation in an atrioventricular valve, it is desirable that an apparatus such as apparatus 1300 minimize the inhibition of blood flow from an atrium to a ventricle during, for example, diastole. Accordingly, a suitable diameter, $D_2$, for a base of a body 1320 is on the order of three to four centimeters. In addition, to further improve blood flow from an atrium to a ventricle during, for example, diastole, body 1320 may include a number of orifices preferably located, when apparatus 1300 is positioned in an atrioventricular valve location superior to the portion of body 1320 that will be collapsed by atrioventricular valve cusps or leaflets. One representative location of orifices 1350 is that position of the body that will reside within an atrium when an atrioventricular valve is closed. Body 1320 may also have reinforcement structures disposed therein or thereon. FIG. 13 shows longitudinally and circumferentially disposed support structures 1325 above body 1320.

Figure 14:
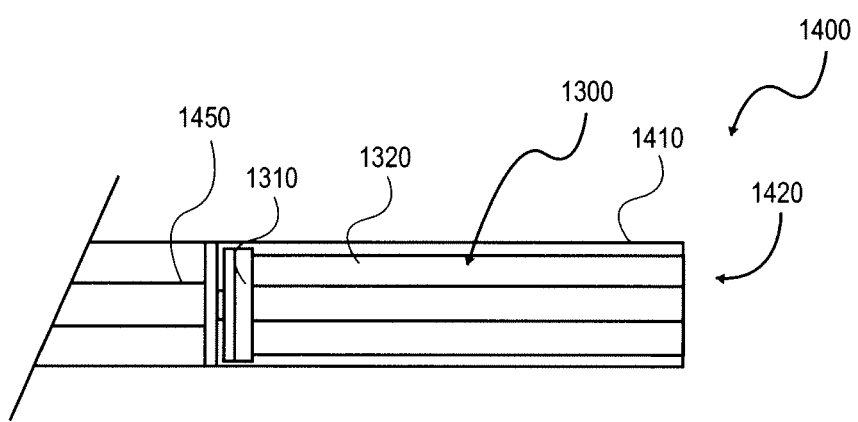
FIG. 14 shows the apparatus of FIG. 13 confined in a catheter sheath.

FIG. 14 shows the distal end of a catheter including an apparatus such as apparatus 1300 disposed therein. Catheter 1400 includes catheter sheath 1410 having lumen 1420 therethrough. A representative diameter for lumen 1420 is on the order of 16 to 24 French (Fr) (about 5 to 8 millimeters).

Disposed within lumen 1420 of catheter sheath 1410 is apparatus 1300. As illustrated in FIG. 14, apparatus 1300, including support annulus 1310 and body 1320, is folded or collapsed within catheter sheath 1410 to have a diameter side to fit within lumen 1420 of catheter 1400. Also disposed in catheter 1400 is plunger sheath 1450 to allow an operator to deliver apparatus 1300 to an atrioventricular valve either by pulling back on catheter sheath 1410 or advancing plunger sheath 1450. Catheter sheath 1410 may be suitable for insertion into a patient through a multi-lumen catheter. A multi-lumen catheter may be used to advance catheter 1400 over, for example, a guidewire. Alternatively, catheter sheath 1410 may be positioned using a guide catheter, deflecting catheter, and/or deflecting guide.

Figure 15:
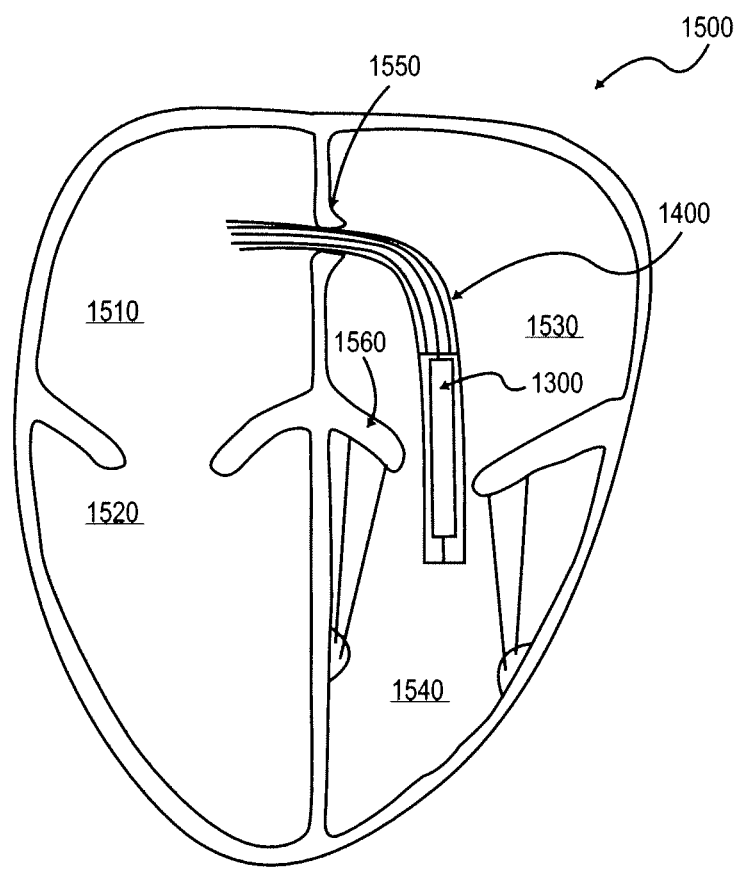
FIG. 15 shows a schematic, cross-sectional front view of a heart with the apparatus of FIG. 13 (in a catheter) inserted transeptally in the left atrium.

FIG. 15 shows catheter 1400 disposed within a heart to position apparatus 1300 within a mitral valve. FIG. 15 schematically illustrates a simplified view of a heart including right atrium 1510 and right ventricle 1520. FIG. 15 also shows heart 1500 having catheter 1400 inserted through fossa ovalis 1550 and through mitral valve 1560. In this illustration, mitral valve 1560 is open. Catheter 1400, in this representation, may be advanced until apparatus 1300 is properly positioned within mitral valve 1560, between atrium 1530 and ventricle 1540. Imaging techniques, including, but not limited to, fluoroscopy or ultrasound may be used to establish an appropriate position for apparatus 1300.

Figure 16:
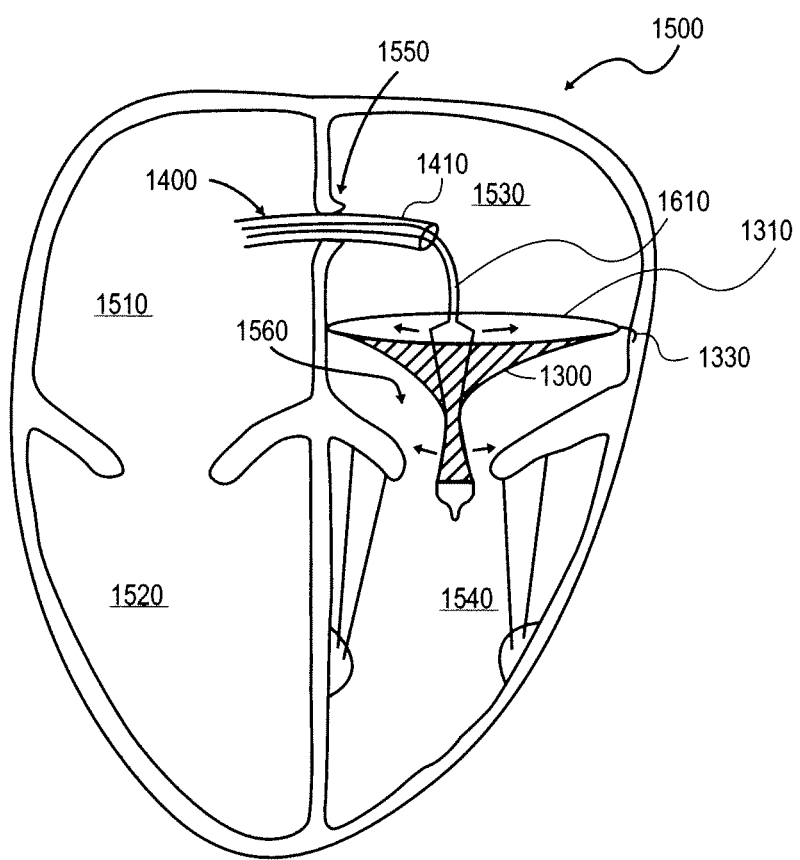
FIG. 16 shows the heart of FIG. 15 during a deployment of the apparatus of FIG. 13 in the atrium and through the mitral valve and using a balloon catheter to deploy the apparatus.

FIG. 16 shows heart 1500 following an initial deployment of apparatus 1300 within mitral valve 1560. In this embodiment, catheter sheath 1410 has been pulled back toward fossa ovalis 1550. Support annulus 1310, when freed from catheter sheath 1410, deploys to a shape, in this embodiment, coinciding with a shape of the wall of left atrium 1530. FIG. 16 also shows barbs 1330 extending into the wall of left atrium 1530.

When deployed, support annulus 1310 and body 1320 of apparatus 1300 may need assistance in adopting a desired shape, such as the shape illustrated in FIG. 13. Accordingly, in one embodiment, a dilation balloon catheter (such as used for valvuloplasty), with an approximately three centimeter inflated balloon diameter, may be advanced through catheter 1400 or through another catheter into apparatus 1300. FIG. 16 shows dilation balloon 1610 disposed within apparatus 1300 (e.g., through support annulus 1310) into body 1320. Dilation balloon 1610 may then be expanded to deploy body 1320 and/or support annulus 1310. Dilation balloon 1610 may also be used to deploy barbs 1330 into the wall of left atrium 1530. Once deployed, dilation balloon 1610 may be deflated and removed.

Figure 17:
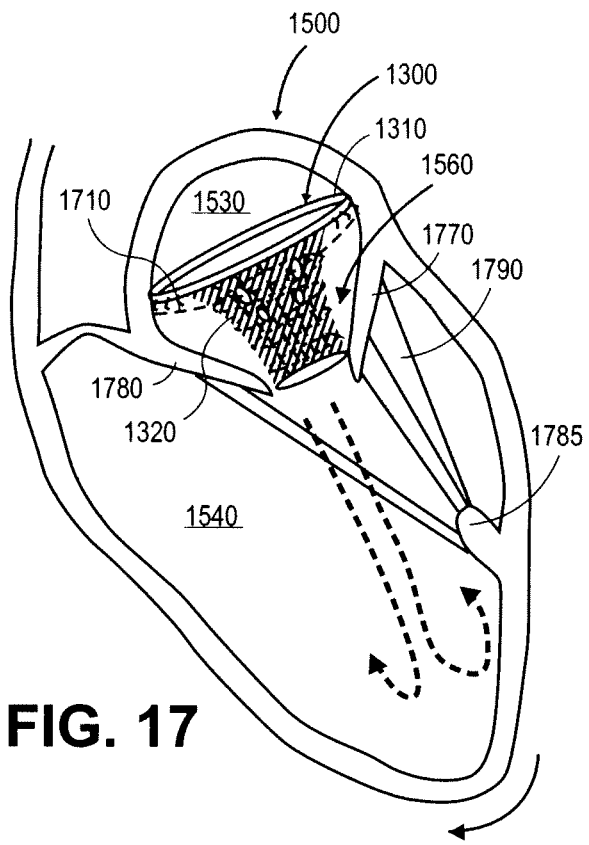
FIG. 17 shows a schematic, cross-sectional view of the left side of the heart of FIG. 15 at diastole with the apparatus of FIG. 13 deployed.
Figure 18:
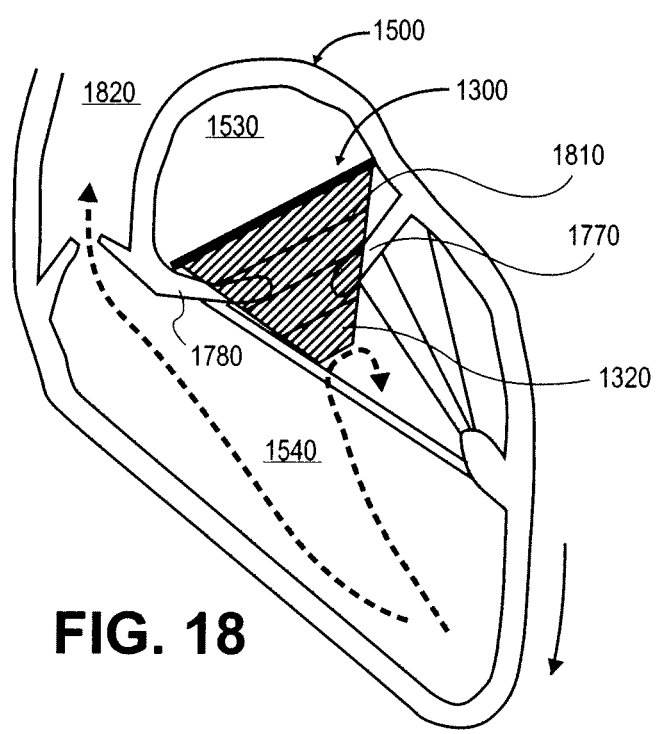
FIG. 18 shows a schematic, cross-sectional view of the left side of the heart of FIG. 15 at systole with the apparatus of FIG. 13 deployed.

FIGS. 17 and 18 show apparatus 1300 within a mitral valve. FIGS. 17 and 18 show a simplified schematic view of a left side of heart 1500. FIG. 17 shows apparatus 1300 disposed in left atrium 1530 in this case, above mitral valve annulus 1710. Support annulus 1310 is disposed in left atrium 1530. Body 1320 resides within mitral valve. Cusps or leaflets 1770 and 1780 of the mitral valve are shown connected to papillary muscle 1785 through chordae tendinae 1790. During diastole, blood flows (dashed lines) into left ventricle 1540. Because of its funnel-like shape, the effective orifice area of apparatus 1300 will be somewhat smaller than that of a dilated native mitral valve. However, the resulting smaller diastolic flow area should result in an increased convective acceleration of the blood through apparatus 1300. This effect may have the added advantage of increasing a forward blood flow washout between left atrium 1530 and left ventricle 1540, thereby reducing the likelihood of the formation or dislodgment of any thromboembolic material in cases where left atrium 1530 may be enlarged.

FIG. 18 shows heart 1500 during systole. Left ventricle 1540 is shown pumping blood through aortic arch 1820. During systole, a portion of apparatus 1300 corresponding to body 1320 protruding into left ventricle 1540 collapses during the pressure rise accompanying systole. The collapse causes body 1320 to close a gap between cusps or leaflets 1770 and 1780. The collapse of body 1320 of apparatus 1300 is illustrated by folds 1810 in body 1320. By reducing the area of any opening between cusps or leaflets 1770 and 1780, regurgitation through mitral valve 1660 is reduced.

Figure 19:
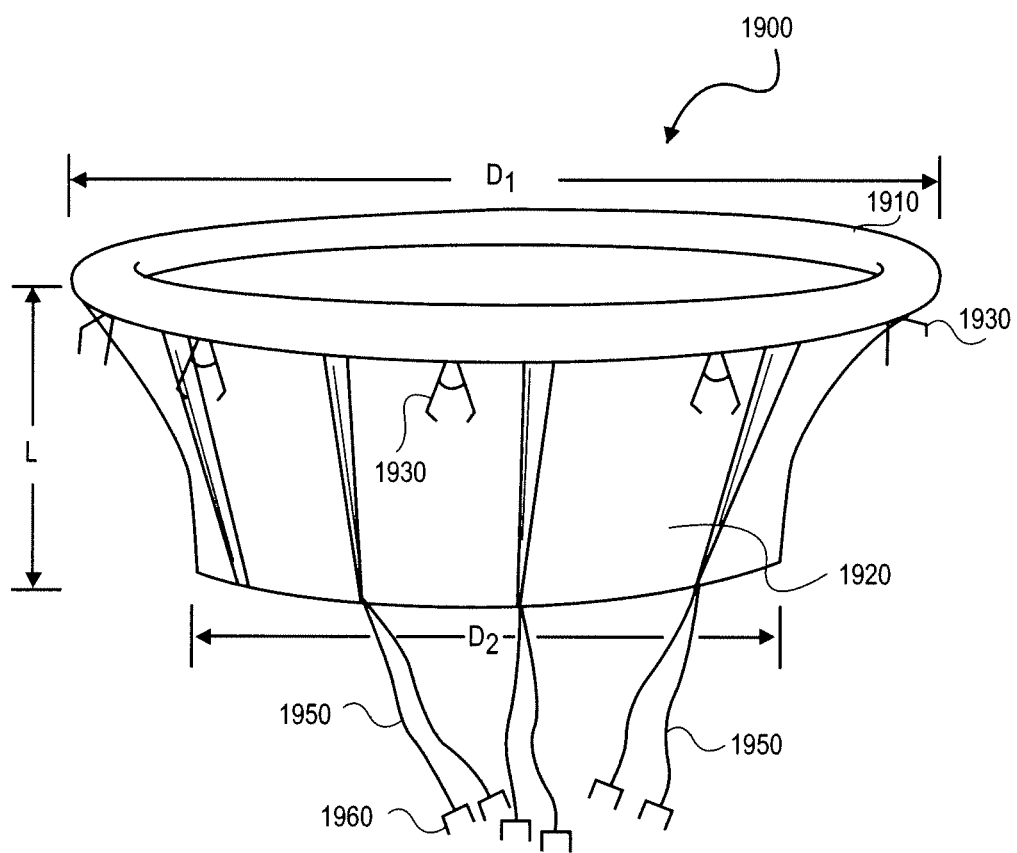
FIG. 19 shows a perspective top schematic view of another embodiment of an apparatus suitable for modifying an atrioventricular valve.

FIG. 19 shows another embodiment of an apparatus sized to be suitable to modify an atrioventricular valve, such as to improve the aptation of the valve. Apparatus 1900 includes support annulus 1910 and body or aptation device 1920. In one embodiment, support annulus 1910 and body 1920 are a single, unitary body of, for example, a single material. Representatively, body 1920 is a relatively thin, flexible material such as a polymer material (e.g., ePTFE or eHDPE) that may be deformed by cusps or leaflets of an atrioventricular valve. Support annulus 1910 may be made of similar material, perhaps with additional structural integrity (e.g., thicker or supported with an additional material). In one embodiment, a suitable material for support annulus 1910 and body 1920 is or is coated with a material that resists or inhibits thrombosis.

Support annulus 1910 has a diameter, $D_1$, suitable to be anchored against the wall of an atrium (e.g., left atrium) or atrioventricular valve annulus (e.g., mitral valve annulus). A representative diameter is on the order of 19 to 31 centimeters. Body 1920 has a length, L, selected to be long enough to extend between cusps or leaflets of an atrioventricular valve and provide surface area for the cusps or leaflets to aptate against when the atrioventricular valve is closed. Body 1920 is shown with a proximal diameter, $D_1$, of support annulus 1910. At a distal end, the diameter, $D_2$, of body 1920 tapers (or is reduced).

Support annulus 1910 may be a material that is flexible to maintain its position with the contraction of a heart. Support annulus 1910 may also be a material that is selected to be suitable to stabilize the size and geometry of the atrioventricular valve annulus to inhibit progressive valvular degradation and to provide a stable platform for body 1920. The material of support annulus 1910 and body 1920 is also suitable for being reduced in diameter (e.g., folded) to a diameter suitable to be placed within a catheter sheath. Thus, in one embodiment, apparatus 1900 is suitable for percutaneous delivery.

Apparatus 1900 shown in FIG. 19 may include barbs or hooks 1930 to anchor support annulus 1910 to the inner wall of an atrium or an atrioventricular valve annulus. One suitable hook is a hook similar to ENDO-HOOKS™ (a registered trademark of Endo Vascular Technologies, Inc. of Menlo Park, Calif.). Representative hooks or barbs are described in EP0712614 titled "Intraluminal Stent for Attaching a Graft." and U.S. Pat. No. 5,681,346 titled "Expandable Stent Forming Projecting Barbs and Method for Deploying," issued to Orth et al. and assigned to Advanced Cardiovascular Systems, Inc. of Santa Clara, Calif.

In one embodiment, body 1920 of apparatus 1900 in FIG. 19 is flexible enough to collapse with the pressure buildup in a ventricle or by the action of atrioventricular valve closure. To prevent prolapse, body 1920 may be reinforced with struts 1940 that extend longitudinally from support annulus 1910 to the base of body 1920 (as viewed). Struts 1940 may taper in a longitudinal direction from support annulus 1910. A suitable material for struts 1940 is a metal, including but not limited to, a NiTi alloy or a polymer material. In the case of a metal or thrombogenic material for struts 1940, struts 1940 may be encapsulated or coated with a non-thrombogenic material. The presence of struts 1940 will serve, in one aspect, to reduce prolapse upon closure of an atrioventricular valve.

Apparatus 1900 also includes flexible cords or tethers 1950 extending beyond the base of body 1920 and, optionally, connected at a proximal end to struts 1940. Cords or tethers 1950 have a length suitable to anchor apparatus 1900 to the papillary muscles associated with an atrioventricular valve. Cords or tethers 1950 may terminate in distal clips 1960 to anchor apparatus 1900 to papillary muscle.

Figure 20:
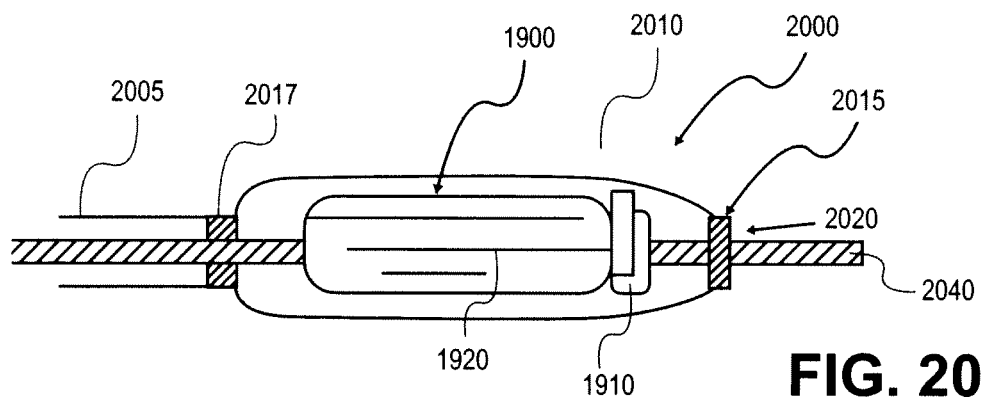
FIG. 20 shows the apparatus of FIG. 19 confined in a catheter sheath.

FIG. 20 shows the distal end of a catheter including an apparatus such as apparatus 1900 disposed therein. Catheter 200 includes catheter sheath 2010 having lumen 2020 therethrough. A representative diameter for lumen 2020 to contain apparatus 1900 is on the order of 16-24 Fr.

Disposed within lumen 2020 of catheter sheath 2010 is apparatus 1900 disposed over optional guide support 2040 (e.g., guide wire). As illustrated in FIG. 20, apparatus 1900, including support annulus 1910 and body 1920, is folded or collapsed within catheter sheath 2010 to have a diameter to fit within lumen 2020 of catheter 2000. At a proximal end of catheter sheath 2010 is primary lumen 2005 having a diameter on the order of 8-10 Fr. In this embodiment, disposed on each end of catheter sheath 2010 are visualization markers 2015 and 2017. Visualization markers are, for example, radiopaque markers.

One percutaneous delivery approach is the transeptal approach described above with respect to apparatus 100 (e.g., FIGS. 3-4 and the accompanying text) and apparatus 1300 (e.g., FIGS. 14-16 and the accompanying text). Alternatively, to insert apparatus 1900 about a mitral valve, apparatus 1900 may be introduced through the aortic arch into the left ventricle and across the mitral valve.

Figure 21:
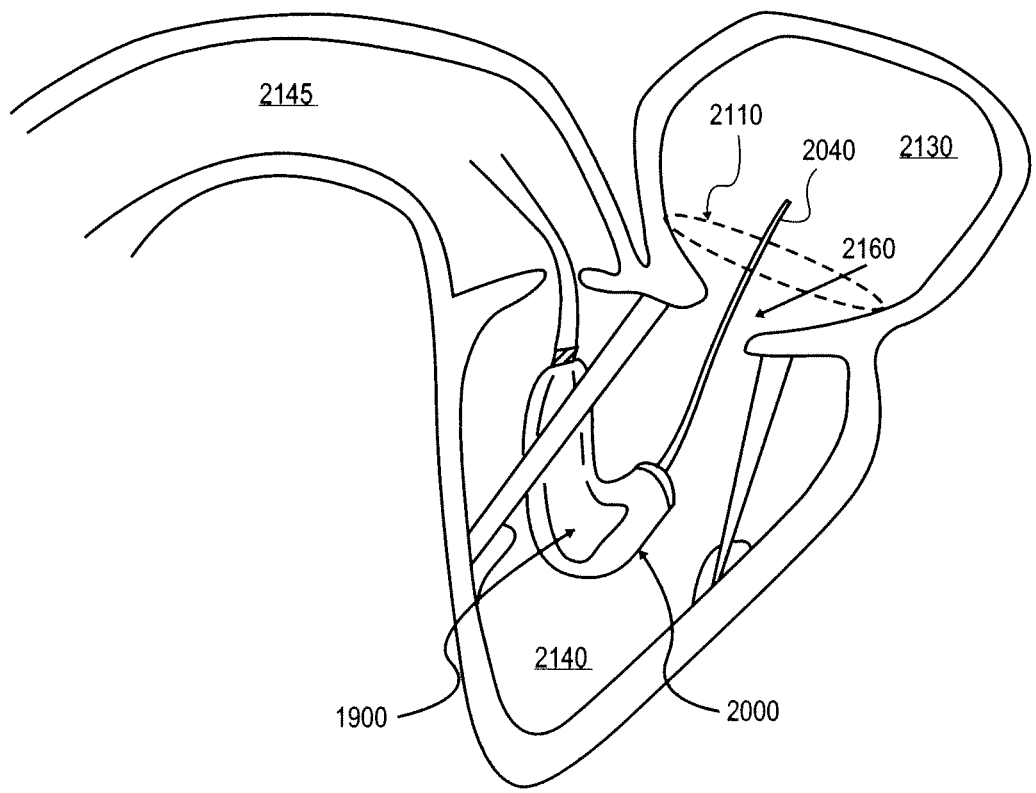
FIG. 21 shows a schematic cross-sectional side view of a left side of the heart with the apparatus of FIG. 19 (in a catheter) introduced into a left ventricle.

FIG. 21 shows catheter 2000 disposed within a heart to position apparatus 1900 within a mitral valve. FIG. 15 schematically illustrates a simplified view of the left side of a heart, including left atrium 2130 and left ventricle 2140. Aortic arch 2145 is shown extending from left ventricle 2140. In this embodiment, catheter 2000 is advanced, for example, over guide support 2040 (e.g., guidewire) over aortic arch, into left ventricle 2140, and into left atrium 2130. Although shown in FIG. 21 as extending over a guide support that may be a guidewire, it is appreciated that alternatively, catheter 2000 may be advanced through a guide catheter that has traversed mitral valve 2160. In one embodiment, catheter 2000 is advanced through mitral valve 2160. Apparatus 1900 may be deployed by retracting catheter 2000 and support annulus 1910 of apparatus 1900 may be seated, perhaps through the aid of visualization markers in, in this embodiment, mitral valve annulus 2110. By continuing to retract catheter 2000, catheter 2000 will pull a distal end of apparatus 1900 forcing cords or tethers 1950 to the base of mitral valve annulus 2110 and into left ventricle 2140.

Figure 22:
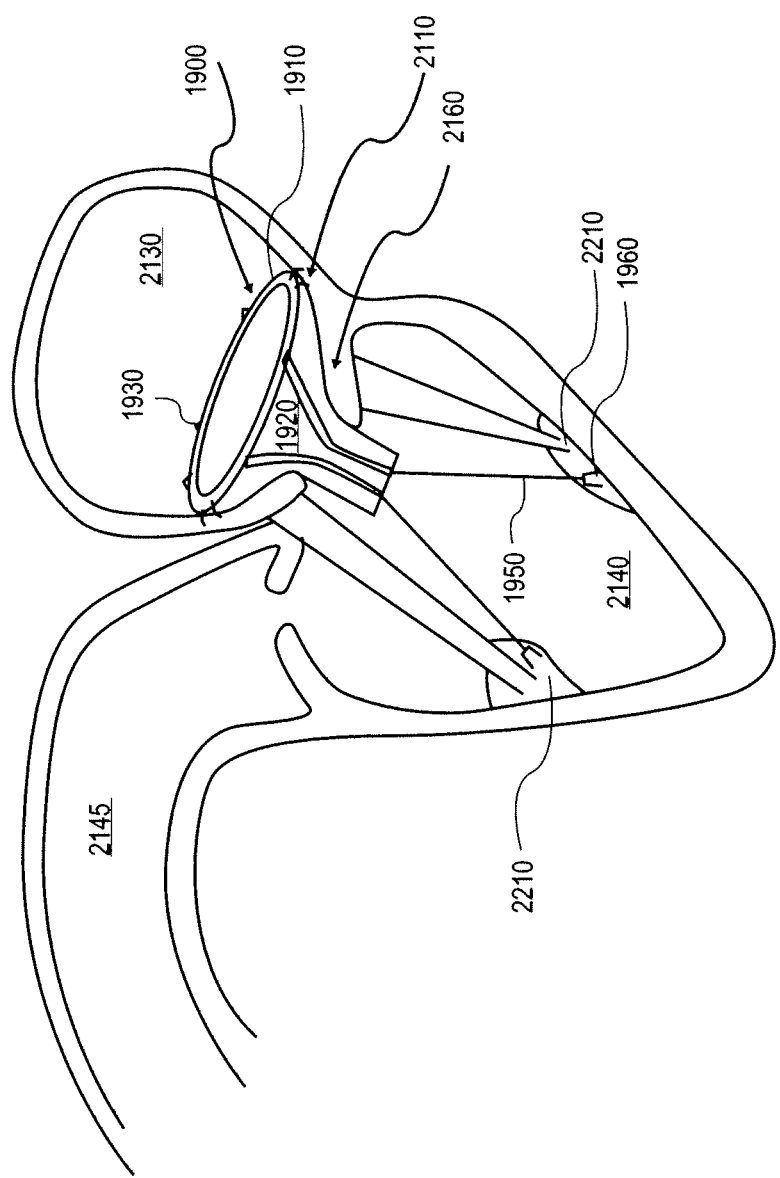
FIG. 22 shows the heart of FIG. 21 with the apparatus of FIG. 19 deployed about the mitral valve.

FIG. 22 shows apparatus 1900 deployed about mitral valve 2160. FIG. 22 shows support annulus 1910 of apparatus 1900 connected, in this embodiment, to mitral valve annulus 2110 and body 1920 extending into left ventricle 2140. Cords or tethers 1950 are connected to papillary muscles 2210 in left ventricle 2140. Distal clips 1960 may be connected to papillary muscles 2210 through the use of an additional tool inserted through catheter 2000 or a separate catheter.

FIG. 23 shows another embodiment of an apparatus sized to be suitable to modify an atrioventricular valve, such as to improve the aptation of the valve. Apparatus 2300 includes support annulus 2310 and body 2320. Support annulus 2310 has a dimension suitable, in one embodiment, for being seated in an atrioventricular valve annulus, such as a mitral valve annulus. Representatively, support annulus 2310 has a diameter on the order of 19 to 31 mm. In one embodiment, support annulus 2310 is made of a material suitable to stabilize the size and geometry of the atrioventricular valve annulus to inhibit progressive valvular degradation, and to provide a stable platform for body 2320.

In one embodiment, support annulus 2310 includes "C"-shaped or "U"-shaped rings 2315 connected to the exterior perimeter of support annulus 2310 as mechanical features to anchor support annulus 2310 to an atrioventricular valve annulus. FIG. 24 shows a cross-sectional view through lines A-A' and illustrates "C"-shaped ring 2315. "C"-shaped ring 2315 includes, in this embodiment, optional barbs 2410 to further aid in anchoring support annulus 2310 to an atrioventricular valve annulus. FIG. 25 illustrates a "U"-shaped ring as an alternative anchoring device. A suitable material for "C"-shaped or "U"-shaped ring 2315 is a metal material that may be completely embedded in the tissue of an atrioventricular valve annulus. One suitable metal material is a NiTi alloy having a shape memory property. Such material may be placed in one configuration to aid in percutaneous delivery and return to a predetermined shape when introduced in a heart.

Apparatus 2300 shown in FIG. 23 also includes body or aptation device 2320. Body 2320, as viewed, is connected to support annulus 2310 at a superior portion of body 2320 and that, from a side or cross-sectional view, resembles a tear-drop shape with a base of the tear-drop shaped body having a thickness T measured from the side or a cross-section. The tear-drop shape provides a minimum profile at an atrioventricular valve annulus that tends to maximize the available cross-sectional valve area for proper blood flow through the valve when the valve is open. The tear-drop shape also accommodates the natural shape of an atrioventricular valve (e.g., mitral valve) transition into the ventricle. A suitable length, L, for body 2320 is one that, with support annulus 2310 in an atrioventricular valve annulus, extends a distance sufficient so that cusps or leaflets of the atrioventricular valve (e.g., mitral valve) contact side 2325 and side 2327 of body 2320 on the closure of the valve.

In one embodiment, body 2320 is designed to be laterally immobile. According to this embodiment, a width, W, of body 2320 is slightly wider (e.g., 105 to 115 percent) than a nominal width of a native atrioventricular valve (e.g., mitral valve). In another embodiment, body 2320 is designed to be laterally mobile. In this embodiment, a width, W, of body 2320 is the majority of the width of a native atrioventricular valve (e.g., mitral valve). A representative majority is greater than 50 percent, and, in another embodiment, 70 percent to 80 percent of the native valve. Representatively, an operator (e.g., physician) can move body 2320 laterally to a desired location within the valve. In one embodiment, apparatus may include a rod across support annulus 2310 to which body 2320 is connected and can be displaced laterally (e.g., a proximal end of body 2320 may wrap around the rod). For example, after deployment of support annulus 2310, an operator can verify proper placement/orientation of body 2320 within an atrioventricular valve using various visualization techniques. Once positioned, body 2320 can be locked in place such as by clamping a proximal end of body 2320 to a rod or to support annulus 2310. In another embodiment, possibly including a rod bridging support annulus 2310, body 2320 may have a lateral dimension less than an inner diameter of support annulus 2310. In this embodiment, body 2320 is fixed in place (e.g., fixed to a rod) in an offset position. The off-center embodiment may be desired, for example, in situations where regurgitation results from chordae rupture on one end of a mitral valve.

As noted above, in one embodiment, body 2320 is formed of a tear-drop-like shape. FIG. 26 illustrates this shape. In one embodiment, a majority of the thickness of body 2320 is selected to be of a flexible material, such as silicone, urethane, or other suitable polymer, which will conform to the natural shape/contour of the atrioventricular valve. In one embodiment, body 2320 is encompassed within a flexible, bio-compatible fabric, such as DACRON™, ePTFE, or eHDPE. The bio-compatible fabric provides mechanical protection against wear and abrasion and maintenance of a general shape. Another preferred material for the exterior or exposed portions of body 2320 is a non-thrombogenic material.

As illustrated in FIG. 23 and FIG. 26, body 2320 is connected to support annulus 2310 across an inner diameter of support annulus 2310. In this manner, a superior portion of body 2320 (as viewed) acts as a bridge across support annulus 2310. Since the superior portion of body 2320 in this embodiment of a tear drop shape is configured to be the smallest thickness of the body, obstruction of blood flow when apparatus 2300 is placed in an atrioventricular valve, is minimized.

In another embodiment, body 2320 of apparatus 2300 includes chamber or cavity volume 2330 inside, as illustrated, the thickest part of the body. Chamber or cavity volume 2330 provides a volume for injecting material to enlarge (uniformly or non-uniformly, as needed) the thickness of body 2320 to match the contour of a patient's valve requirement for a given patient. Alternatively, chamber or cavity volume 2330 provides a volume for contrast material to be included in body 2320 to act, in one sense, as a visualization aid.

Figure 27:
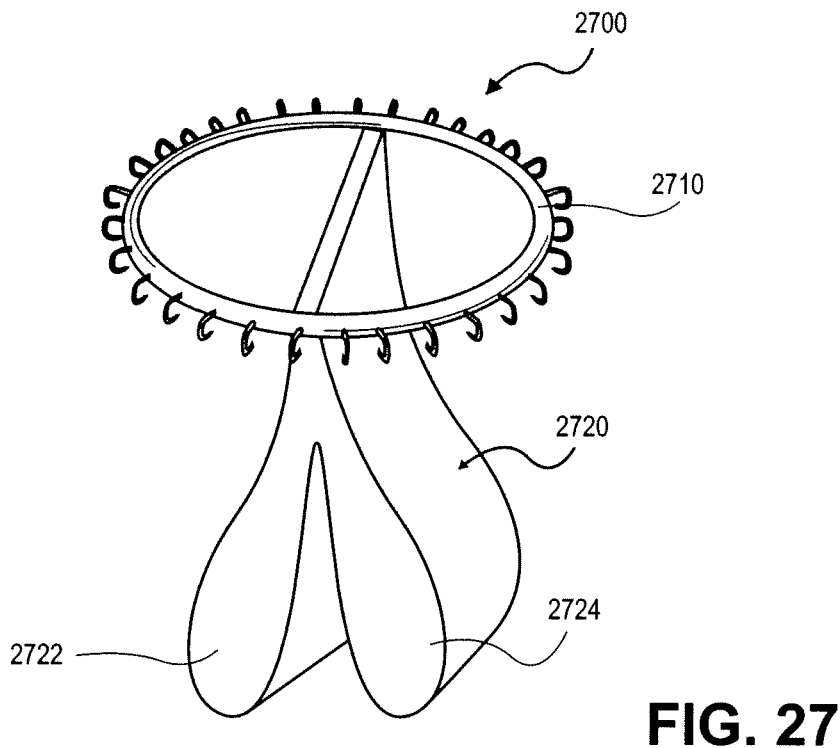
FIG. 27 shows a perspective top schematic view of another embodiment of an apparatus suitable for modifying an atrioventricular valve.

FIG. 27 illustrates another embodiment of an apparatus sized to be suitable to modify an atrioventricular valve, such as to improve the aptation of the valve. Apparatus 2700 is similar to apparatus 2300 (see FIGS. 23-26 and the accompanying text) with support annulus 2710 and body or aptation device 2720. In the embodiment shown in FIG. 27, body 2720 is divided, at a portion of its base (as viewed) into two halves along a central axis. The separate portions are denoted by reference numerals 2722 and 2724. By dividing a portion of body 2720 into separate portions along a central axis, negative pressure caused by ventricular contraction may tend to force portions 2722 and 2724 apart, creating a seal at a ventricular side of an atrioventricular valve, while still providing surface area between the valve cusps or leaflets to allow the cusps or leaflets to close upon side 2725 and side 2727 of body 2720.

Figure 28:
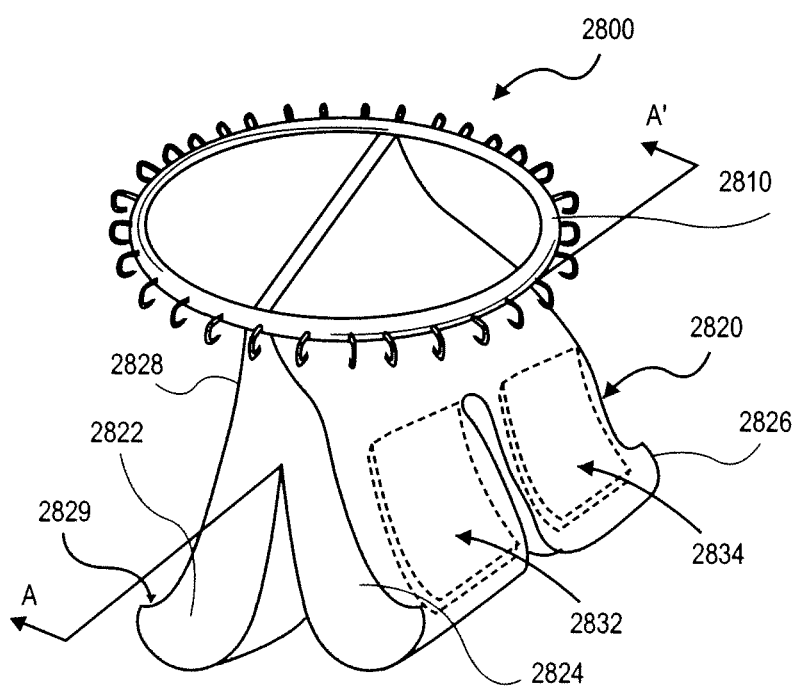
FIG. 28 shows a perspective top schematic view of another embodiment of an apparatus suitable for modifying an atrioventricular valve.

FIG. 28 shows another embodiment of an apparatus sized to be suitable to modify an atrioventricular valve. FIG. 28 is similar to the embodiment described in FIGS. 23-26 and the accompanying text. Apparatus 2800 includes support annulus 2810 and body 2820. In this embodiment, an inferior portion of body 2820 is divided into four portions along two central axes. FIG. 28 illustrates portions 2822, 2824, 2826, and 2828. Additionally, a base of each of the portions of body 2820 are shaped such that the ends are biased outward from a central longitudinal body axis. The shape is illustrated by reference numeral 2829. Shape 2829 of portions 2822, 2824, 2826, and 2828 provides a bias for the portions to open if minimal ventricular back pressure occurs. Body 2820 may also include support structures illustrated by reference numerals 2832 and 2834 (shown in ghost lines) may be incorporated in a body of one or more portions 2822, 2824, 2826, and 2828. Support portions 2832 and 2834 may provide stiffness or a specific contour to a body portion. It is also appreciated that, in either embodiment in either apparatus 2700 or apparatus 2800, a chamber or cavity volume may be present inside the body portions to contain a desired substance, for example to enlarge the thickness (in a uniform or non-uniform manner) to match the contour of a given atrioventricular valve requirement.

In one embodiment, the apparatuses described with reference to FIGS. 23-28 are intended to be introduced percutaneously. Accordingly, in one embodiment, it may be desirable to orient the apparatus within an atrioventricular valve so that the body portion fits desirably between the cusps or leaflets of the valve. FIG. 29 shows a portion of apparatus 2800 through line A-A'. Specifically, FIG. 29 shows body portions 2822 and 2828 of body 2820. Shown connected to respective ones of portions 2822 and 2828 are wires or cords 2842 and 2844, respectively. The wires or cords may extend, for example, the length of a catheter shaft to a proximal end to allow an operator of a catheter to maneuver body 2820. Wires or cords 2842 and 2844 are connected to portion 2822 and 2828 at connecting points 2843 and 2845, respectively. Each wire or cord 2842 and 2844 includes a disengagement point (2847 and 2849, respectively) that, in response to a sufficient tensile force in a controlled direction will separate from connecting points 2843 and 2845, respectively. A separate cord or cords may alternatively or additionally be connected in a similar fashion to support annulus 2310, 2710, and 2810.

In an embodiment where the apparatus is shown in FIGS. 23-29 are intended to be introduced to a patient percutaneously, the material for support annulus (e.g., support annulus 2310 (FIG. 23), support annulus 2710 (FIG. 27), and support annulus 2810 (FIG. 28), and body (body 2320 (FIG. 23), body 2720 (FIG. 27), body 2820 (FIG. 28)) are suitable for being reduced in diameter (e.g., folded, collapsed) to a diameter suitable to be placed within a catheter. Thus, one percutaneous delivery approach is the transeptal approach described above with respect to apparatus 100 (e.g., FIGS. 3-4 and the accompanying text) and apparatus 1300 (e.g., FIGS. 14-16 and the accompanying text). Alternatively, to insert, for example, apparatus 2300, 2700, or 2800 about a mitral valve, the apparatus may be introduced through the aortic arch into the left ventricle and across the mitral valve.

FIG. 30 shows a distal end of a catheter including an apparatus, such as apparatus 2300, apparatus 2700, or apparatus 2800. For ease of discussion, reference will be made to apparatus 2800 within the catheter. Catheter 3000 includes catheter sheath 3010 having lumen 3020 therethrough. Catheter sheath 3010 is disposed around optional protective sheath 3012 that contains apparatus 2800. Protective sheath may include perforated or tear away sections 3060 connected, in one embodiment, to cords 3065. Cords 3065 may extend to a proximal end of a delivery catheter allowing an operation to free apparatus 2800 from protective sheath 3012 by pulling cords 3065.

A representative diameter for lumen 3020 to contain apparatus 2800 is on the order of 16-24 Fr. Disposed within lumen 3020 of catheter sheath 3010 is apparatus 2800. As illustrated in FIG. 30, apparatus 2800, including support annulus 2810 and body 2820 is folded or collapsed within catheter sheath 3010 to have a diameter to fit within lumen 3020 of catheter 3000. At a proximal end of catheter sheath 3010 is primary lumen 3005 having a diameter on the order of 8-10 Fr. In this embodiment, disposed on each end of catheter sheath 3010 are visualization markers 3015 and 3017. Visualization markers are, for example, radiopaque markers.

FIG. 30 shows apparatus 2800 oriented in catheter 3000 with support annulus 2810 at a distal end. Adjacent a portion of support annulus 2810 within catheter 3000, possibly in an annular configuration around support annulus 2810 is mandrel 3050. Mandrel 3050 provides a contact point for ends of "C" or "U"-shaped rings 2315 to contact within catheter 3000. Mandrel 3050 may also serve to bias "C"-shaped or "U"-shaped rings such that when mandrel 3050 is removed, the "C"-shaped or "U"-shaped rings advance into tissue of an atrioventricular valve annulus.

Wires or cords 3040 extend through primary lumen 3005 to a proximal end of the catheter. On a distal end, wire or cords 3040 are connected to apparatus 2800 to provide a capability to position apparatus 2800 within an atrioventricular valve (e.g., to support annulus 2810 or body 2820 (e.g., wires or cords 2842 and 2844). As noted above, cords 3065, connected at a distal end to protective sheath 3012, extend, in one embodiment, through primary lumen 3005. Wire or cords 3040 may also be connected in one embodiment to mandrel 3050 to maneuver mandrel 3050 and orient support annulus 2810. Alternatively, separate wire or cord 3075 may be connected to mandrel 3050.

Figure 31:
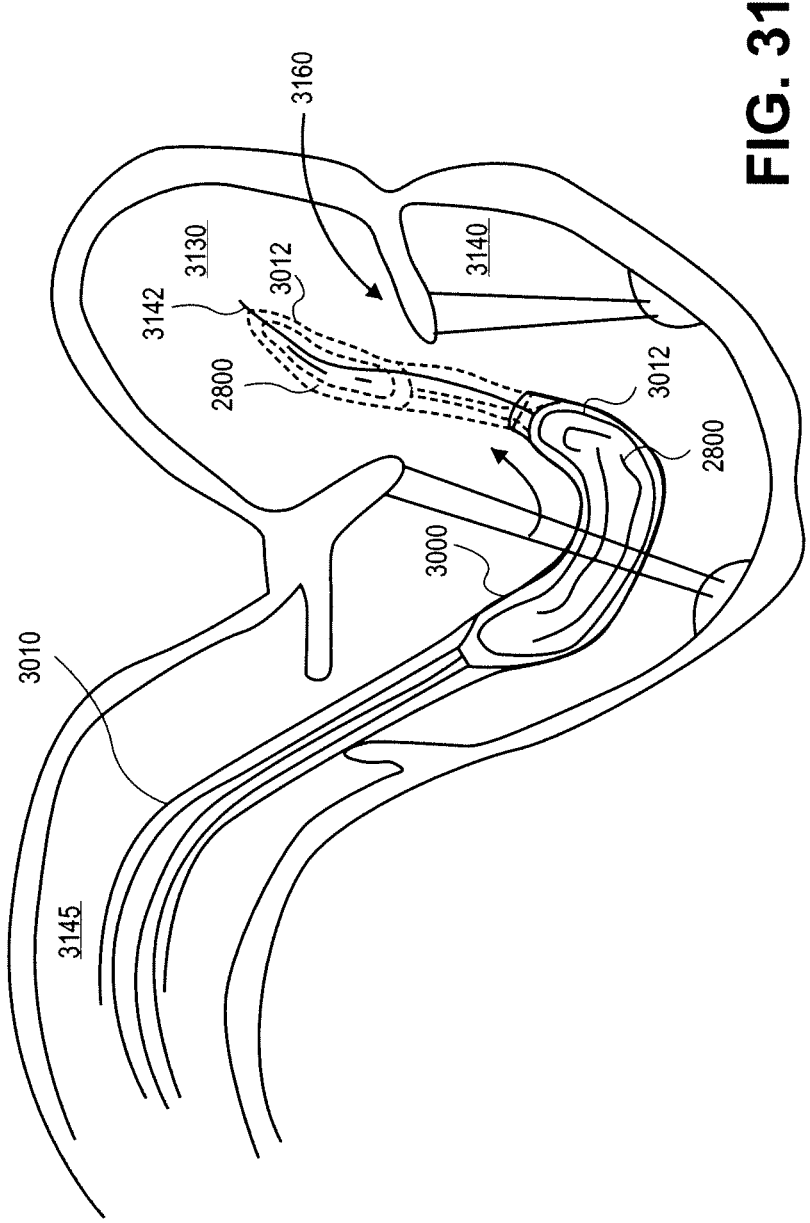
FIG. 31 shows a schematic, cross-sectional side view of a left side of the heart with the apparatus of FIG. 28 (in a catheter) introduced into a left ventricle.

FIG. 31 shows catheter 3000 disposed within a heart to position apparatus 2800 within or about a mitral valve. FIG. 31 schematically illustrates a simplified view of the left side of a heart, including left atrium 3130 and left ventricle 3140. Aortic arch 3145 is shown extending from left ventricle 3140. In this embodiment, catheter 3000 is advanced, for example, over guide support 3142 (e.g., guidewire) over aortic arch, into left ventricle 3140. In one embodiment, protective sheath 3012 is then advanced through catheter sheath 3010 across mitral valve 3160 into left atrium 3130 as illustrated in ghost lines. Once the sheathed and folded apparatus 2800 is across mitral valve 3160 into left atrium 3130, protective sheath 3012 can be removed or retracted, allowing for the initial unfolding of apparatus 2800 into left atrium 3130. Wires or cords 3040 may then be used to position apparatus 2800 within mitral valve 3160 possibly with the use of imaging modalities, such as fluoroscopy, magnetic imaging angiography, doppler, echocardiography, etc.

Figure 32:
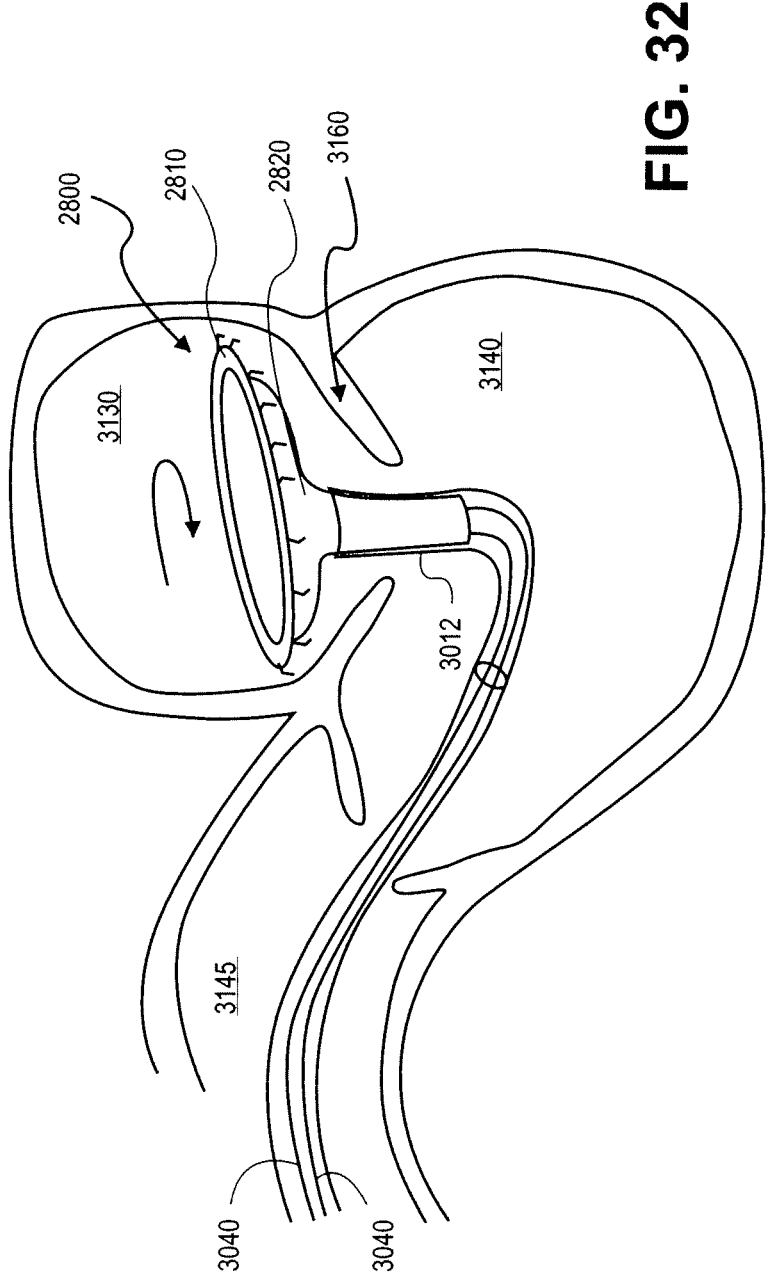
FIG. 32 shows the heart of FIG. 31 with a portion of the apparatus of FIG. 28 introduced into the left atrium.
Figure 33:
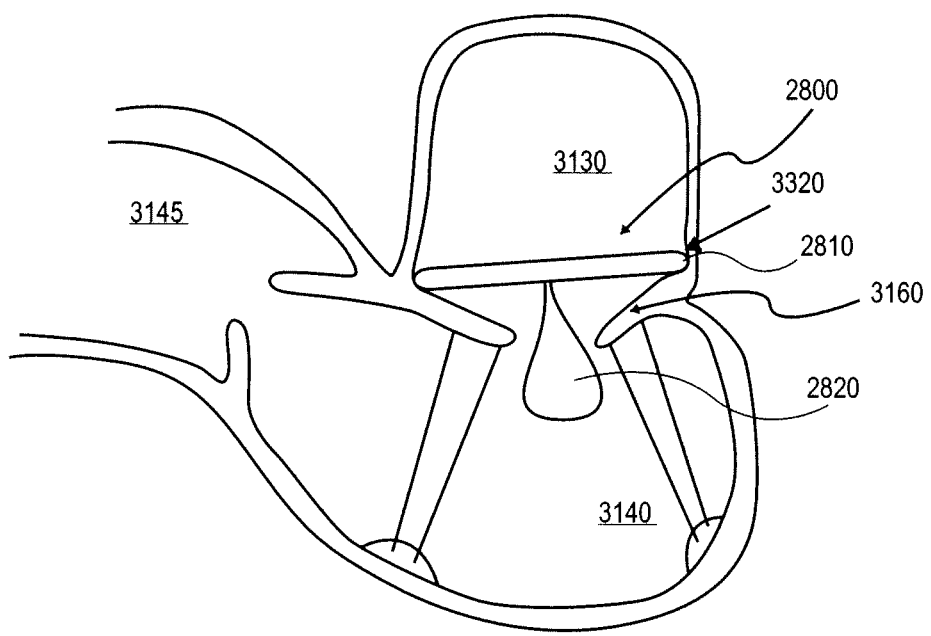
FIG. 33 shows the heart of FIG. 31 with the apparatus of FIG. 28 deployed about the mitral valve.

FIG. 32 shows apparatus 2800 partially unfolded within atrium 3130. In this illustration, apparatus 2800 is oriented so that the inferior portions of body 2820 are not properly positioned between cusps or leaflets of mitral valve 3160. As schematically illustrated, it is desired to rotate apparatus 2800 approximately 180°. An operator (e.g., positioned) may use wires or cords 3040 to rotate apparatus 2800, possibly with the aid of a visualization technique or device. Once support annulus 2810 is properly positioned, protective sheath 3012 is retracted to release body 2820 to flow freely inside left ventricle 3140. FIG. 33 shows support annulus 2810 anchored at mitral valve annulus 3320 and body 2820 extending through mitral valve 3160 into left ventricle 3140.

Using real-time imaging modality such as two-dimensional or three-dimensional color doppler, the placement of body 2820 may be optimized by manipulating its location relative to mitral valve annulus 3320 and support annulus 2810. For example, the optimization may be based on providing spatial and temporal information about the actual extension, direction, origin, and size of intracardiac flows. Representatively, the procedure for the segmentation of turbulent and laminar flows using three-dimensional color doppler allows for the measurement of mitral regurgitant jet volumes that may be used to optimize location of body 2820.

Figure 34:
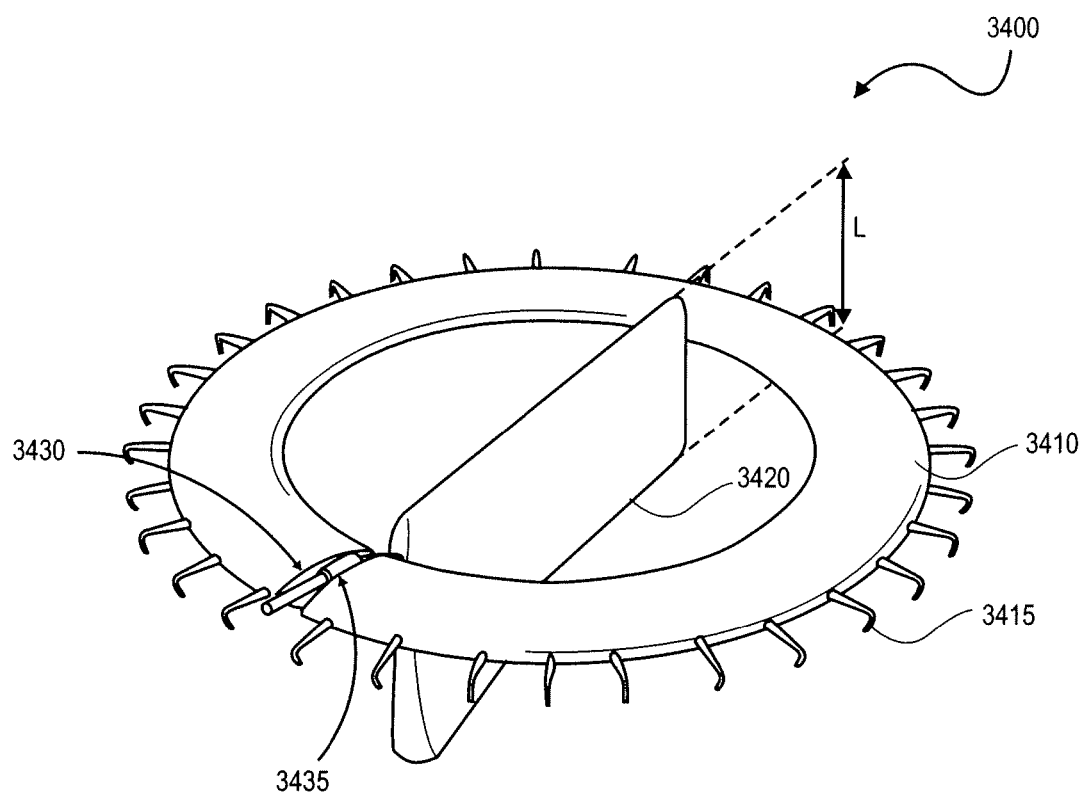
FIG. 34 shows a perspective top schematic view of another embodiment of an apparatus suitable for modifying an atrioventricular valve.

FIG. 34 shows another embodiment of an apparatus sized to be suitable to modify an atrioventricular valve, such as to improve the aptation of the valve. Apparatus 3400 includes support annulus 3410 and body or aptation device 3420. Support annulus 3410 has a dimension suitable, in one embodiment, for being seated in an atrioventricular valve annulus, such as a mitral valve annulus. Representatively, support annulus 3410 has a diameter on the order of 19 to 31 mm. In one embodiment, support annulus 3410 is made of a material suitable to stabilize the size and geometry of the atrioventricular valve annulus to inhibit progressive valvular degradation, and to provide a stable platform on which to attach body 3420. A representative diameter is on the order of 19 to 31 centimeters. In the embodiment illustrated in FIG. 34, body 3420 is attached to support annulus 3410 at two points in such a way to bisect the inner diameter of support annulus 3410.

In one embodiment, support annulus 3410 is a tubular structure having first end 3430 and second end 3435. First end 3430 and second end 3435 are connected to define the annular shape. A number of hooks or barbs, possibly similar to ENDO-HOOKS™ are shown on an exterior of support annulus 3410 to assist in anchoring support annulus to an atrium wall or an atrioventricular valve annulus.

Aptation device or body 3420 has a length, L, selected in one embodiment to extend from support annulus 3410 (a superior portion of body 3420 viewed) through an atrioventricular valve (e.g., mitral valve). In this manner, when apparatus is deployed, for example, with support annulus 3410 in a mitral valve annulus, cusps or leaflets of the mitral valve will contact body 3420 during, for example, systole. A representative length, L, is such that body 3420 is on the order of zero to five millimeters above and one to 30 millimeters below support annulus 3410.

Aptation device or body 3420 may be formed of an elastic material suitable for being folded into a catheter sheath and possibly stretched with the placement of support annulus 3410 in a catheter sheath. An exposed portion of body 3420 and support annulus 3410 may include or be coated with a material that resists or inhibits thrombosis.

Figure 35:
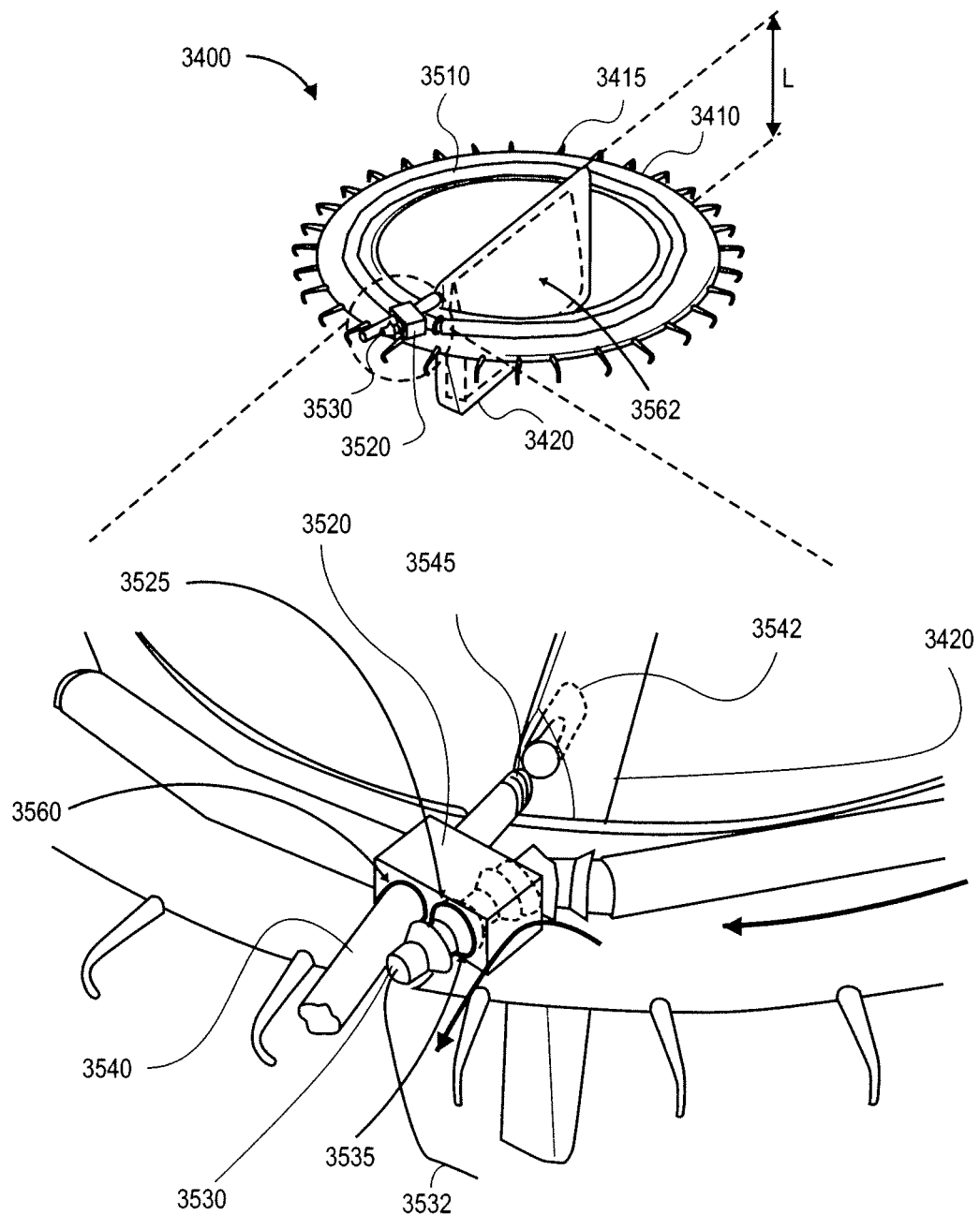
FIG. 35 shows a perspective, cross-sectional schematic view through a superior (as viewed) portion of FIG. 34.

FIG. 35 shows another view of apparatus 3400, specifically a top, perspective cross-sectional view through support annulus 3410. From this view, support annulus 3410 is shown as a tubular structure including inner body 3510. Inner body 3510 includes housing 3520 at one end and second end 3530, designed to be connected to one another to define an annular body within support annulus 3410. In one embodiment, a diameter of inner body 3510 is adjustable. The connection between housing 3520 and second end 3530 illustrate a zip tie (e.g., cable tie-like) fitting where, for example, second end 3530 includes relatively deformable conical/inclined features and opening 3535 in housing 3520 has, for example, a diameter to catch the conical/inclined features therein as a locking mechanism. The fitting and housing 3520 is adjustable by pulling a length of inner body 3510 through housing 3520 by second end 3530. Wire 3532 extends from second end 3530 and is of a length that extends to a proximal end of, for example, a catheter to allow an operator to connect and adjust inner body 3510. Wire 3532 is removable from second end 3530, such as by torquing.

Housing 3520 also includes opening 3560 therethrough for the placement of transport tube 3540 therethrough. Transport tube 3540 extends between ends 3530 to 3435 and connects to bladder 3562 in body 3420. FIG. 35 shows transport tube 3540 having threaded portion 3545 at one end to mate with body 3420. Transport tube 3540 may be utilized to introduce a liquid into bladder 3562 through valve 3542 (e.g., a one-way valve). In one embodiment, once bladder 3562 is filled, transport tube 3540 may be unscrewed from valve 3542, removed from housing 3520 and discarded.

Figure 36:
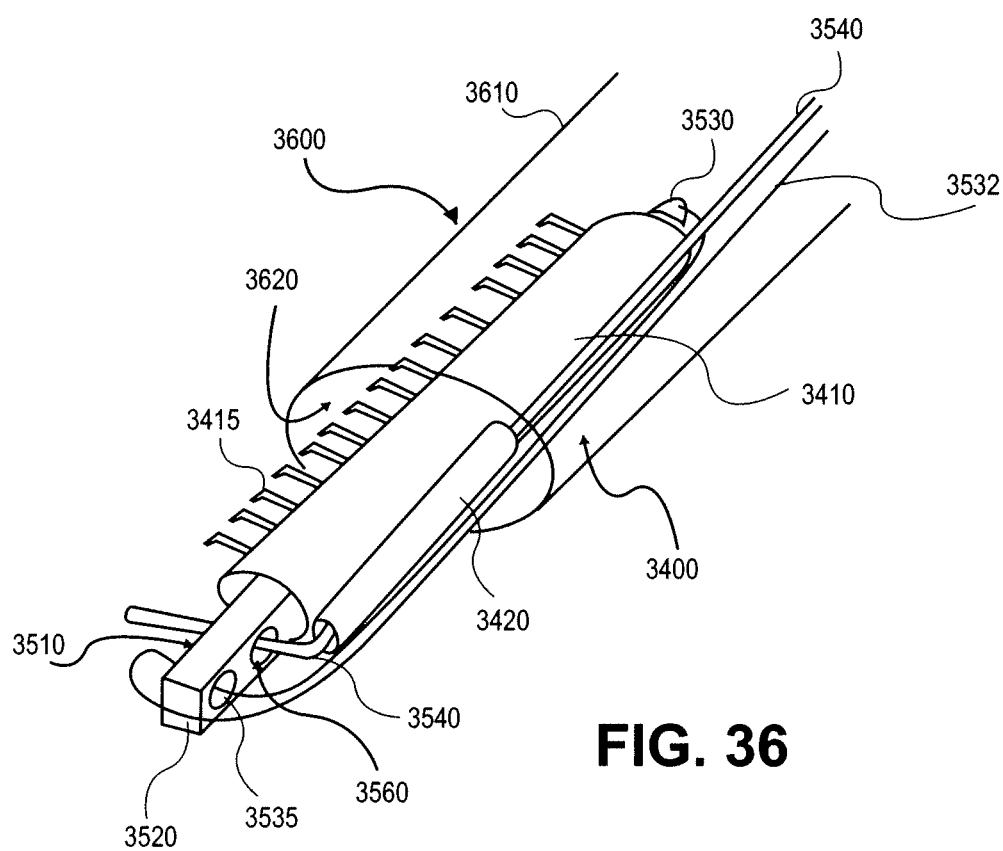
FIG. 36 shows the apparatus of FIG. 34 confined in a catheter sheath.

In one embodiment, apparatus 3400 may be introduced percutaneously. To introduce apparatus 3400 to modify a mitral valve, apparatus 3400 may be introduced transeptally or through the aortic arch into the left ventricle and across the mitral valve. One advantage to the embodiment shown is that apparatus 3400 may be conformed to a desired shape and geometry of an atrioventricular valve annulus (or atrium) in situ. Representatively, apparatus 3400 may be introduced through a catheter as a linear structure (e.g., support annulus 3410) and modified to an annular shape about an atrioventricular valve. FIG. 36 shows apparatus 3400 linearly disposed within a catheter. FIG. 36 shows support annulus 3410 of apparatus 3400 housed in catheter 3600 as a linearly extending tube with hooks or barbs 3415 on one side. Catheter 3600 includes catheter sheath 3610 having lumen 3620 therethrough. Lumen 3620 has a diameter sufficient to encompass apparatus 3400 including support annulus 3410 and body 3420. FIG. 36 shows inner body 3510 extending through support annulus 3410. A portion of inner body 3510, including housing 3520, is exposed from catheter 3600. In this view, opening 3535 and opening 3560 are shown which accommodate second end 3530 and transport tube 3540, respectively. Looped through opening 3535 is wire 3630. One end of wire 3630 extends to a proximal end of catheter 3600 allowing an operator to manipulate inner body 3510, for example, to place second end 3530 within opening 3535 to form an annular structure. A second end of wire is detachably connected to second end 3530. Representatively, once second end 3530 is placed through opening 3535 and inner body 3510 is adjusted to be a desired diameter, wire 3630 may be detached from second end 3530 such as by applying a sufficient torquing or pulling force. Transport tube 3540 is shown extending through opening 3560. Another end of transport tube extends to a proximal end of catheter 3600 allowing an operator to introduce a material into transport tube 3540.

Figure 37:
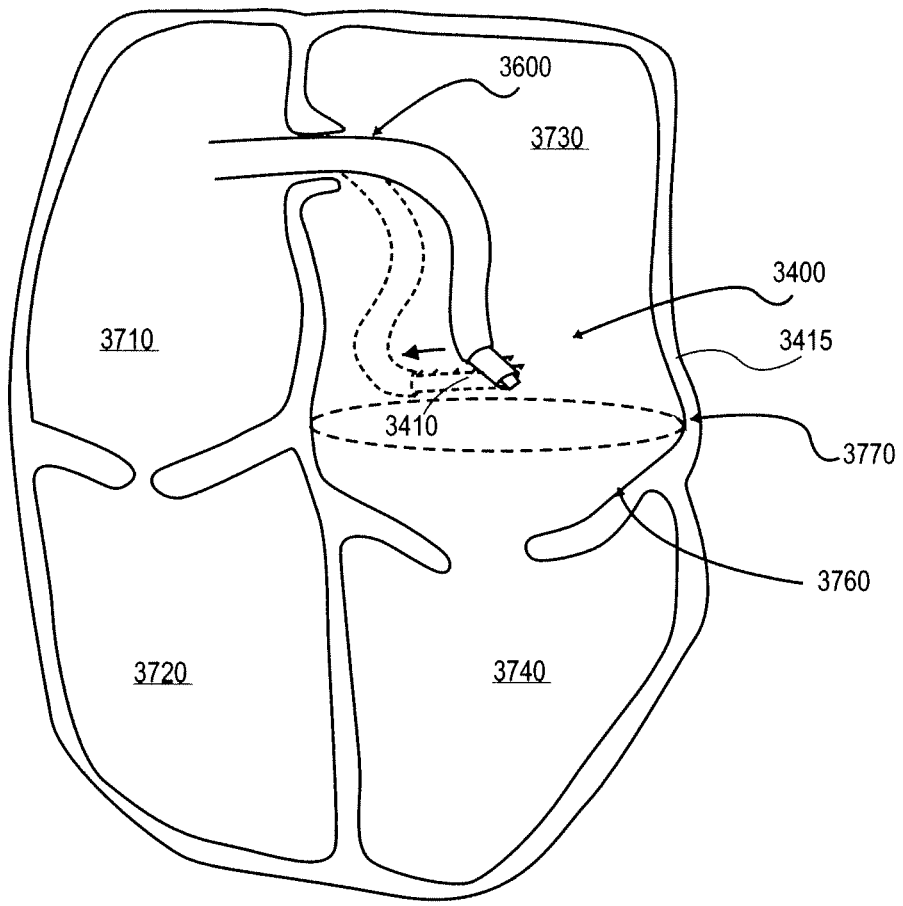
FIG. 37 shows a perspective, cross-sectional schematic front view of a heart and the deployment of the apparatus of FIG. 34 about the mitral valve annulus.

FIG. 37 shows apparatus 3400 introduced into a left atrium transeptally through catheter 3600. In one embodiment, apparatus 3400, once introduced, is advanced out of catheter 3600 incrementally to expose linearly configured support annulus 3410. FIG. 37 shows the incremental advancement of support annulus 3410 from catheter 3600 and around mitral valve annulus 3770. As illustrated, hooks 3415 are positioned so that as apparatus 3400 is advanced from catheter 3600, hooks are adjacent to the tissue around mitral valve annulus 3770. Imaging techniques may be utilized to properly orient apparatus 3400. Accordingly, hooks 3415 are anchored incrementally into the tissue of mitral valve annulus 3770 and support annulus 3410 is advanced around mitral valve annulus 3770.

Once all hooks 3415 are in place and support annulus 3410 encircles mitral valve annulus 3770, the diameter of support annulus 3410 is modified or optimized. Referring to FIG. 36 in conjunction with FIG. 38, an operator will place second end 3530 of inner body 3510 in opening 3535 of housing 3520. The operator may then use wire 3630 to pull second end 3530 through opening 3535 until a desired diameter of inner body 3510 and support annulus 3410 is established. At this point, wire 3630 may be pulled or torqued so that it disconnects from inner body 3510. Apparatus 3400 appears tilted forward in the otherwise cross-sectional front view of the heart to illustrate one representative orientation of apparatus 3400.

Figure 38:
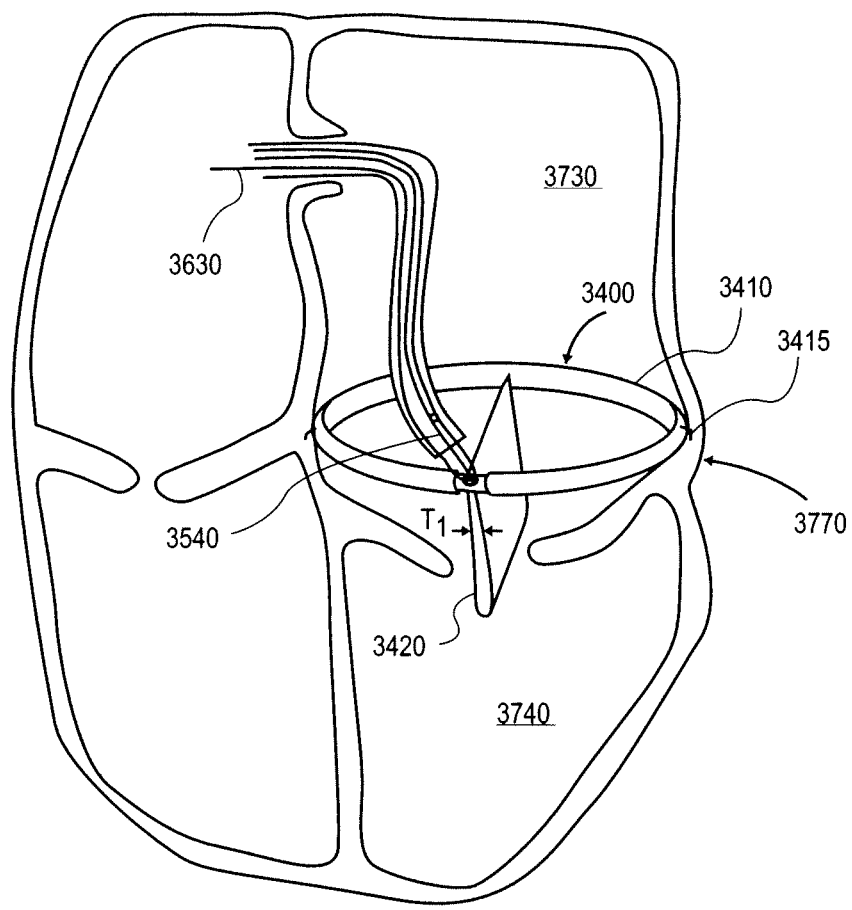
FIG. 38 shows the heart of FIG. 37 with a portion of the apparatus of FIG. 34 deployed and a further operation in the deployment of the apparatus.

As illustrated in FIG. 38, body 3420 is connected to support annulus 3410 at one end and approximately at half the length of the annulus. In this manner, when support annulus 3410 is formed into an annular shape, a superior portion (as viewed) of body 3420 bisects or acts as a bridge across support annulus 3410. Where support annulus 3410 is desired to be introduced as a linear structure prior to being deployed within mitral valve annulus 3770, a material for body 3420, at least at the portions connected to support annulus 3410 should be sufficiently elastic so that the portion can stretch along approximately one-half the length of support annulus 3410 in a linear, pre-deployed position.

Figure 39:
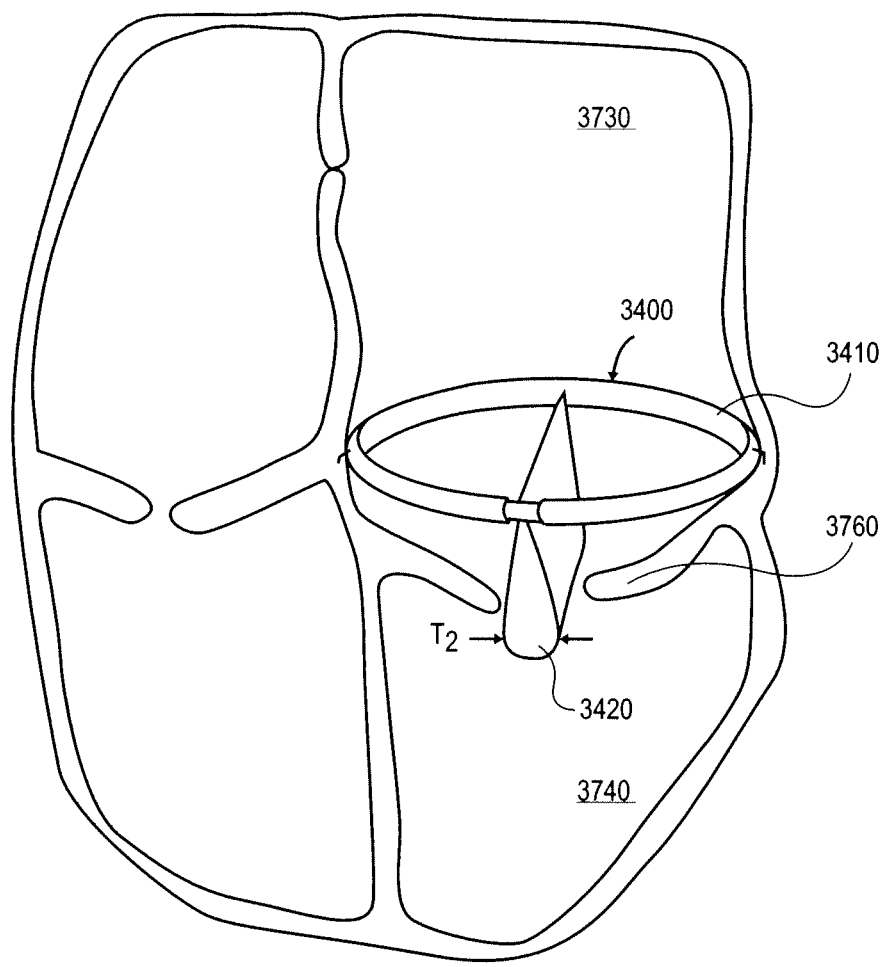
FIG. 39 shows the heart of FIG. 37 with the apparatus of FIG. 34 deployed about the mitral valve.

Once support annulus 3410 is in place and inner body 3510 is adjusted or modified, body 3420 extends between cusps or leaflets of a mitral valve. At this point, a liquid or other material may be introduced into bladder 3562 to modify the volume (thickness) of body 3420. FIG. 38 shows body 3420 having a thickness, $T_1$. Transport tube 3540 extends from valve 3542 to bladder 3562 through catheter 3600 to a proximal end of catheter 3600. A suitable material, such as a liquid material, may be added to bladder 3562 to change the dimensions of body 3420. In one embodiment, a solidifying liquid is introduced into bladder 3562. Representatively, transport tube 3540 may be a dual lumen transport tube to accommodate two-part solidifying liquids, such as used in adhesives and epoxies. One example is REPROSIL™ (a registered trademark of Dentsply International Inc. of Milford, Del.). REPROSIL™ is a hydrophilic vinyl polysiloxane impression material. Once a sufficient volume of material has been added to bladder 3562, transport tube 3540 is cleared using, for example, a vacuum or suction. Transport tube 3540 may then be torqued and unscrewed from valve 3542. Catheter 3600 may then be removed from the patient leaving in place apparatus 3400. FIG. 39 shows apparatus 3400 disposed within/about mitral valve 3760, with apparatus 3400 again tilted forward for understanding purposes. As illustrated, body 3420 has a thickness, $T_2$ resulting from a material being added to bladder 3562. In one embodiment, $T_2$ is greater than $T_1$ shown in FIG. 38. In FIG. 39, body 3420 has a tear drop shape. It is appreciated that the final shape may be many different shapes (e.g., rectangular).

Figure 40:
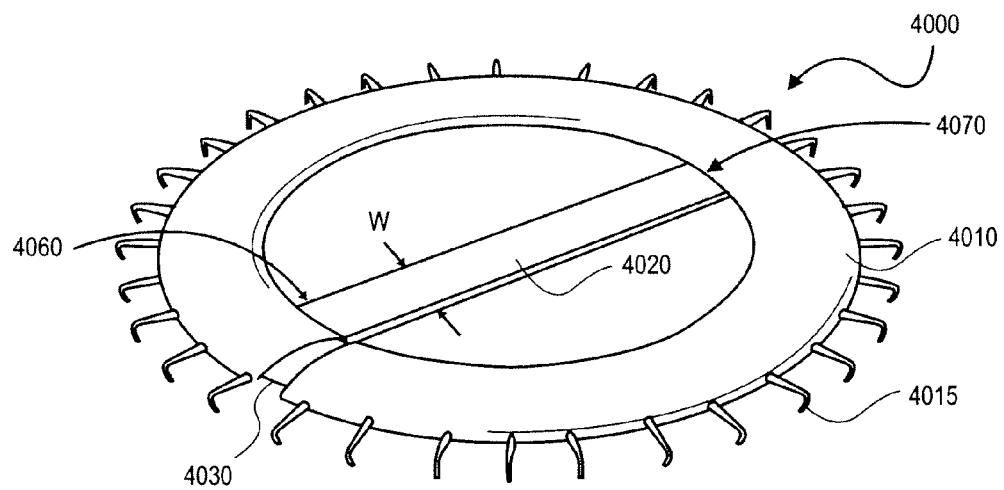
FIG. 40 shows a perspective top schematic view of apparatus suitable for modifying an atrioventricular valve.

FIG. 40 shows another embodiment of an apparatus suitable to modify an atrioventricular valve, including improving the aptation of cusps or leaflets of the valve. FIG. 40 shows apparatus 4000 comprised of support annulus 4010 and aptation device or body 4020. In one embodiment, support annulus 4010 is similar in many respects to support annulus 3410 of apparatus 3400, including a tubular body with an inner body 4030 that may provide an adjustment mechanism for modifying or optimizing the annular dimension of support annulus 4010. Suitable hooks, such as ENDOHOOKS™ 4015 may be connected to an exterior circumference of support annulus 4010 to be used to anchor apparatus 4000 to atrium tissue or tissue of an atrioventricular valve annulus.

Apparatus 4000 includes body 4020 extending as a bridge across the inner diameter of support annulus 4010. Body 4020 is connected to support annulus 4010 at points 4060 and 4070 and is made of material that is flexible enough to expand to allow support annulus 4010 to be configured linearly in a catheter body.

In one embodiment, body 4020 is intended to modify the aptation of an atrioventricular valve, specifically addressing problems of prolapse, billowing, and flail. Specifically, body 4020 has a dimension, width, W, that, when apparatus 4000 is seated in an atrioventricular valve annulus, is suitable to inhibit cusps or leaflets of an atrioventricular valve from extending above the valve annulus. In this manner, the cusps or leaflets are maintained together when the cusps or leaflets are under pressure.

Figure 41:
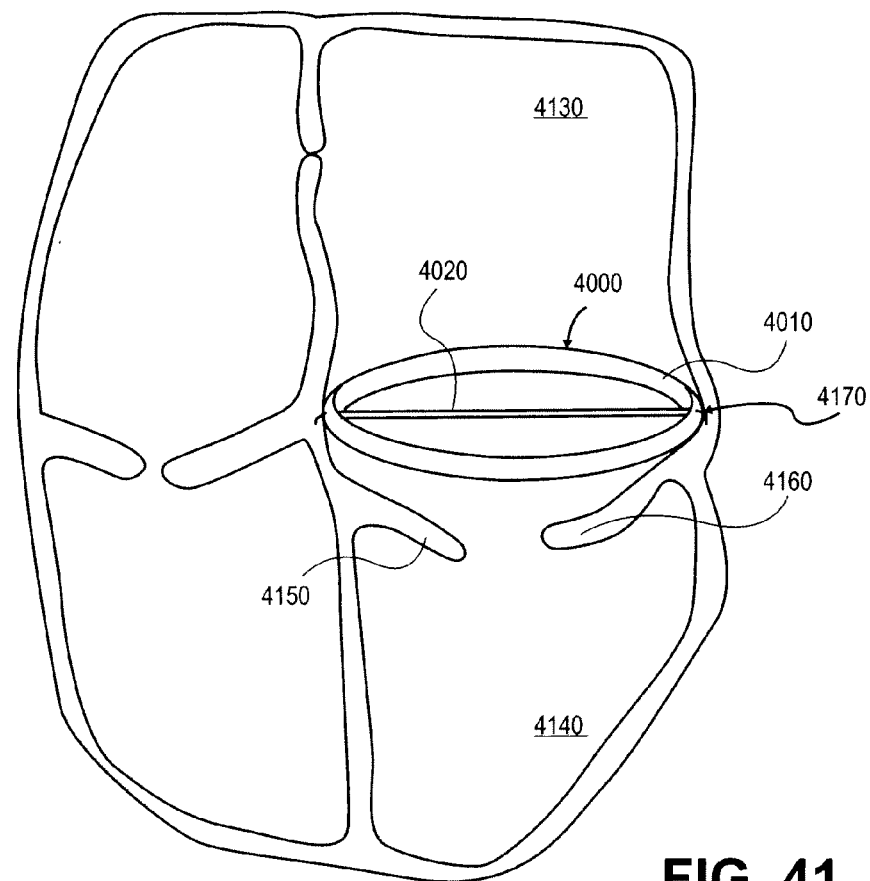
FIG. 41 shows a perspective, cross-sectional schematic front view of a heart and the deployment of the apparatus of FIG. 40 about the mitral valve annulus with the cusps or leaflets of the valve in an open position.
Figure 42:
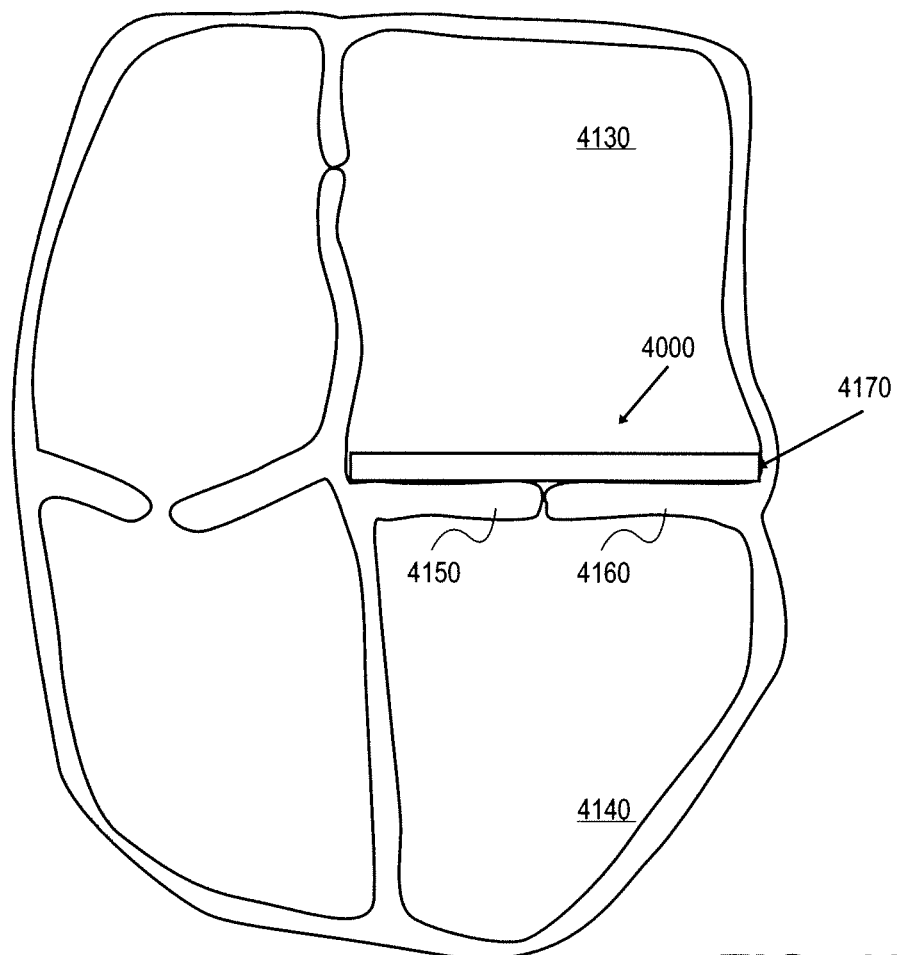
FIG. 42 shows a schematic, cross-sectional front side view of the heart of FIG. 41 with the cusps or leaflets of the mitral valve in a closed position.

FIG. 41 shows apparatus 4000 suited in mitral valve annulus 4170. Apparatus 4000 appears tilted forward in this otherwise cross-sectional front view of a heart to illustrate one representative orientation of apparatus 4000. Apparatus 4000 may be introduced into mitral valve annulus 4170 percutaneously similar to the introduction of apparatus 3400 described above with reference to FIGS. 37-39 and the accompanying text. FIG. 41 shows body 4020 of apparatus 4000 disposed above cusps or leaflets 4150 and 4160 of the mitral valve, in a generally planar relationship with support annulus 4010. Cusps or leaflets 4150 and 4160 are in an open position. FIG. 42 shows cusps or leaflets 4150 and 4160 in a closed or aptated position. The presence of apparatus 4000, specifically body 4020 of apparatus 4000, inhibits cusps or leaflets 4150 and 4160 from extending into left atrium 4130.

It is appreciated that width, W, of body 4020 may be minimized to minimize the obstruction of blood flow through an atrioventricular valve. It is appreciated that by orienting body 4020 properly across cusps or leaflets 4150 and 4160, a width, W, may be minimized. It is appreciated that, when positioning apparatus 4000 within mitral valve annulus 4170, visualization markers may be utilized to assist in establishing a desired orientation for apparatus 4000.

Figure 43:
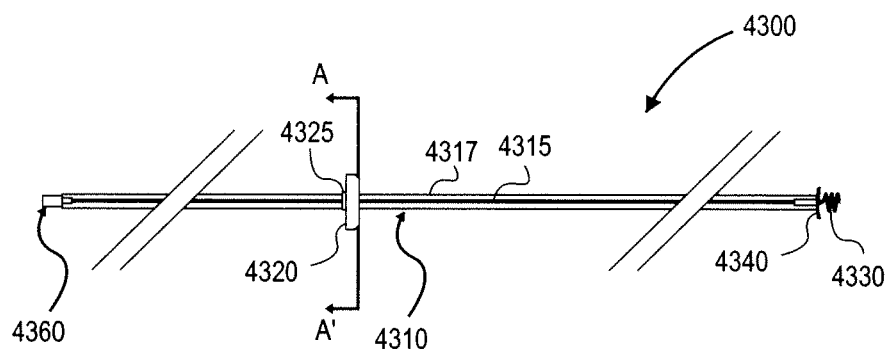
FIG. 43 shows a schematic side view of another embodiment of an apparatus suitable for modifying an atrioventricular valve.

FIG. 43 shows a side schematic view of another embodiment of an apparatus suitable for use in modifying an atrioventricular valve. Apparatus 4300 includes tether 4310 and aptation device or body 4320, each of a size suitable for percutaneous delivery to an atrium and/or a ventricle of a heart. In one embodiment, tether 4310 of apparatus 4300 is similar to tether 110 discussed in reference to FIGS. 1A-1F and the accompanying text. Representatively, tether 4310 includes, in one embodiment, duplex spring 4315 to provide torsional stiffness and sheath 4317. Connected at a distal end of tether 4310 is anchor 4330 to anchor tether 4310 to a wall of a ventricle. It is appreciated that anchor 4330 can be a helical anchor (FIG. 43) and be attached in various manners, including those described with reference to FIGS. 1A-1C and the accompanying text. Alternatively, other anchors are suitable, including the hook and/or barb configuration described with reference to FIG. 1D and FIG. 1E and the accompanying text. In one embodiment, patch 4340 is located between tether 4310 and anchor 4330. A proximal end of tether 4310 includes stud 4360 to receive, for example, a female mate attached to a proximal end of a catheter to transmit a rotation of a catheter or an instrument within the catheter to apparatus 4300. A proximal end tether 4310 may also be connected to a power source to function as a pacing lead.

Connected to tether 4310 in the embodiment shown in FIG. 43 is aptation device or body 4320. Aptation device 4320, in this embodiment, is a cylindrical disk. Aptation device 4320 is connected to tether 4310 about a center axis. Aptation device 4320 is connected, in one embodiment, at a position on tether 4310 corresponding to a location to contact cusps or leaflets of an atrioventricular valve during at least one of systole and dystole when tether 4310 is connected to the ventricle. In one embodiment, suitable for mitral valve modification, a distal end of aptation device 4320 is delivered to the vicinity of the plane of the mitral valve annulus (at slightly above or slightly below) during systole. Since the mitral valve annulus is saddle-shaped, it is appreciated that there are a range of planes that fit into this shape and are roughly parallel to the major and minor axes of the mitral valve. Representatively, a location is seven to eight centimeters from a distal end of tether 4310, but a wider range of dimensions can be made to function depending, at least in part, upon where anchor 4330 is positioned in the ventricle. Aptation device 4320 is connected to tether 4310 at connection 4325 by, for example, adhesive. Alternatively, aptation device 4320 may be adjustably connected to tether 4310 such as through a ratchet-type connection, representatively illustrated in FIG. 1F and described in the accompanying text. A representative thickness of aptation device 4320 as a disk is on the order of under five millimeters.

Figure 45:
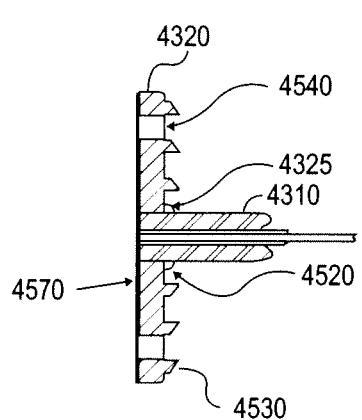
FIG. 45 shows a portion of the apparatus of FIG. 43 through line B-B' of FIG. 44.
Figure 44:
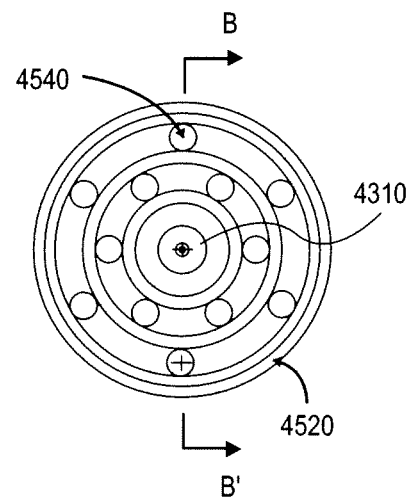
FIG. 44 shows a portion of the apparatus of FIG. 43 through line A-A' of FIG. 43.

FIG. 44 shows a sectional distal view of apparatus 4300 at line A-A' in FIG. 43. FIG. 45 shows a cross-sectional side view through line B-B' of FIG. 44. FIG. 44 and FIG. 45 illustrate features of aptation device 4320.

In one embodiment, aptation device 4320 is a circular disk having a thickness sufficient to inhibit cusps or leaflets of an atrioventricular valve from prolapse, billowing, or flail when suited in an atrioventricular valve annulus. Representatively, aptation device 4320 is a polymer material having a thickness on the order of 0.001 to 4 millimeters. Aptation device 4320 also has a diameter selected to be of a size sufficient to inhibit cusps or leaflets of a mitral valve from extending to an atrium as part of prolapse, billowing, or flail. A representative diameter is on the order of 5 to 25 millimeters. Openings 4540 may facilitate diastole flow into the ventricle and/or a holding force on the leaflets during systole (due, representatively, to the pressure difference between the ventricle and the atrium).

Aptation device 4320 has proximal side 4510 and distal side 4520. Referring to distal side 4520 of aptation device 4320, aptation device 4320 may include a plurality of cylindrical ridges 4530 and may include a plurality of openings 4540 through aptation device 4320. Ridges 4530 may facilitate a holding force on the leaflets during systole. Ridges 4530 are shown with end portions angled toward tether 4310 at, for example, angle, a, of 45-90°. The ridges may get deeper (deeper into aptation device 4320) toward the outer edge of aptation device 4320.

In one embodiment, it is contemplated that aptation device 4320 will be seated approximately in an atrioventricular valve annulus and the cusps or leaflets of an atrioventricular valve may contact aptation device 4320 when a pressure builds in a ventricle and causes the cusps or leaflets to aptate. Thus, the cusps or leaflets will be raised to contact aptation device 4320. When the cusps or leaflets contact aptation device 4320, openings 4540 through aptation device 4320 create a pressure difference during systole. Cusps or leaflet material will tend to be forced into openings 4540 providing friction to aptation device to inhibit a cusp or leaflet from moving from distal side 4520 and pushing around aptation device 4320 and escaping, resulting in prolapse, billowing, or flail. Ridges 4530 may serve similarly to inhibit cusps or leaflets from moving or sliding off distal side 4520.

In one embodiment, apparatus 4300 is suitable for percutaneous delivery. Thus, aptation device 4320 may be made of a material that can be reduced to the diameter of a delivery catheter lumen. Representatively, aptation device 4320 may include a shape memory material (e.g., NiTi alloy) or superelastic metal and/or elastic metal and/or polymer reinforcement material to define or support a desired implanted shape, possibly coated or embedded in a material that inhibits thrombosis.

Figure 46:
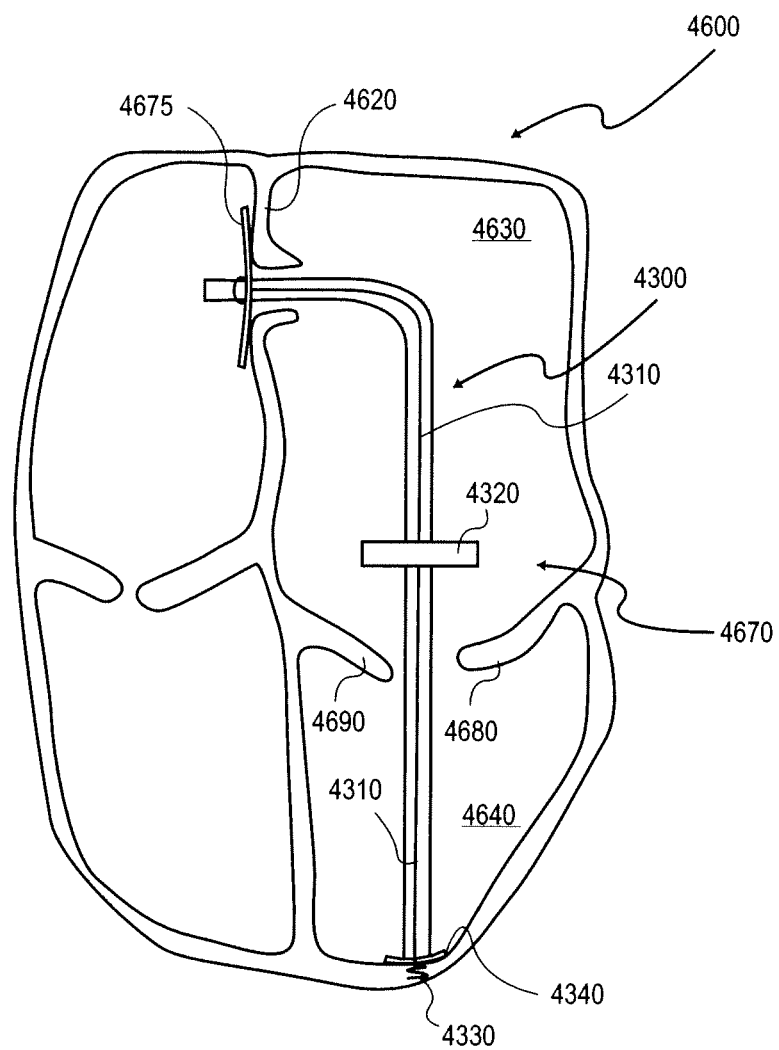
FIG. 46 shows a schematic, cross-sectional front side view of a heart with the apparatus of FIG. 43 deployed on a left side and the cusps or leaflets of the mitral valve in an open position.

To deliver apparatus 4300 to modify a mitral valve, the apparatus may be delivered transeptally or through the aortic arch into the left ventricle and across the mitral valve. For a transeptal approach including coupling of tether 4310 to a left ventricle and interatrial septum, reference is made to FIGS. 3-4 and the accompanying text. FIG. 46 shows apparatus 4300 positioned in a left atrium and left ventricle. Referring to FIG. 46, a distal end of tether 4310 of apparatus 4300 is connected to a base of left ventricle 4640 through helical anchor 4330. Helical anchor 4330 may include projecting barbs to improve the anchoring. Helical anchor 4330 may also include a conductive material such as platinum iridium as a lead for pacing operations. A proximal portion of tether 4310 of apparatus 4300 is connected to an interatrial septum 4620. Patch 4675 is disposed on a right atrium side of interatrial septum 4620.

Aptation device 4320 of apparatus 4300 is connected to tether 4310 and, in this embodiment, disposed in mitral valve annulus 4670. As viewed, aptation device 4320 is above or superior to mitral valve cusps or leaflets 4680 and 4690. The mitral valve is shown in FIG. 46 in an open position.

Figure 47:
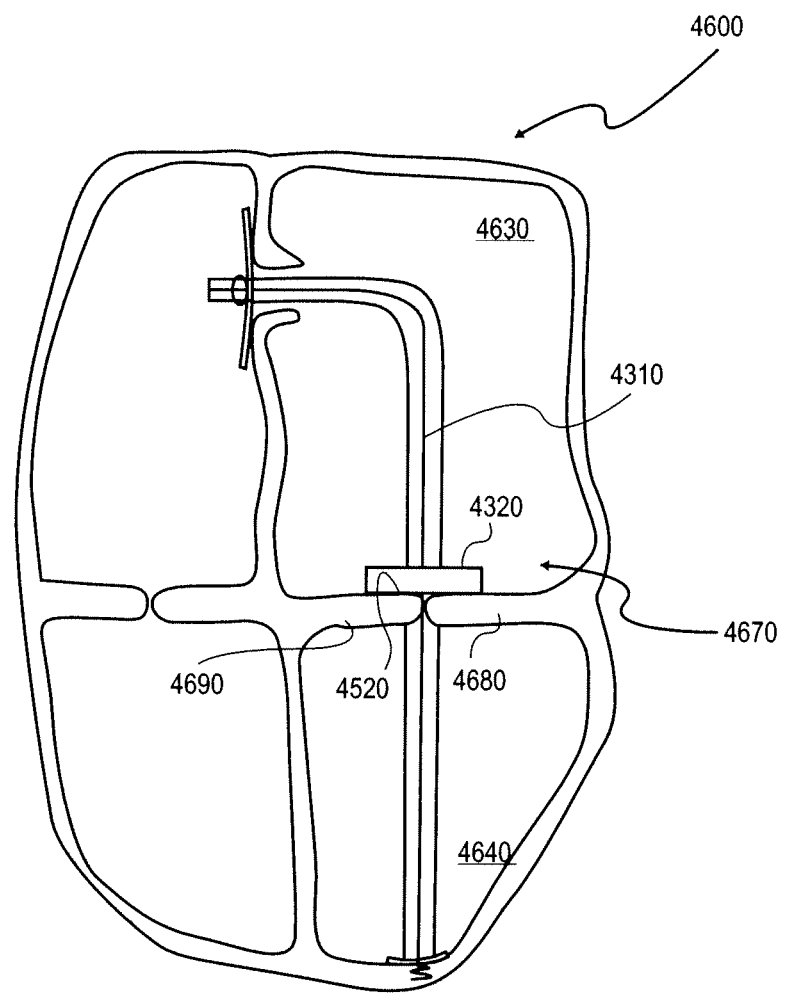
FIG. 47 shows the heart of FIG. 46 with the cusps or leaflets of the mitral valve in a closed position.

FIG. 47 shows heart 4600 with the mitral valve between left atrium 4630 and left ventricle 4640 in a closed position, such as during systole. In this embodiment, cusps or leaflets 4680 and 4690 are shown contacting distal side 4520 of aptation device 4320. With the mitral valve closed, aptation device 4320 resides in left atrium 4630. As illustrated, aptation device 4320 inhibits conditions such as prolapse, billowing, and flail, by restricting the movement of cusps or leaflets 4680 and 4690 beyond the mitral valve annulus.

Figure 48:
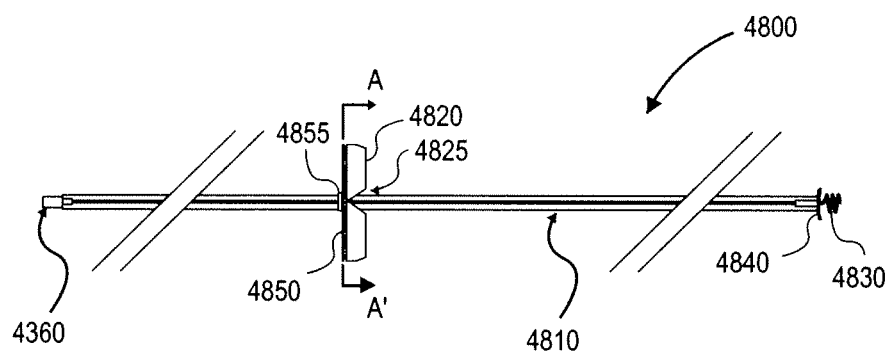
FIG. 48 shows a schematic, side view of another embodiment of an apparatus suitable for modifying an atrioventricular valve.

FIG. 48 illustrates another embodiment of an apparatus suitable to modify an atrioventricular valve. Apparatus 4800 includes tether 4810 and aptation device 4820. Apparatus 4800 may be similar to apparatus 4300 described above in that tether 4810 is selected, in one embodiment, to be connected at a distal end, through anchor 4830 to a wall of a ventricle, such as the base of the left ventricle in a mitral valve modification procedure. Patch 4840 is disposed between tether 4810 and anchor 4830. A proximal end of tether 4810 is selected, in one embodiment, to be connected to an interatrial septum.

Aptation device 4820 is connected to tether 4810, in one embodiment, at a position coinciding with an atrioventricular valve annulus or atrium such that, aptation device 4820 contacts cusps or leaflets of an atrioventricular valve upon closure of the valve, such as during systole. Aptation device 4820 includes plication portion 4825 including, in one embodiment, a groove (e.g., a "V" shaped groove) on a distal side. Plication portion 4825 allows aptation device 4820 to fold distally toward tether 4810 in response, for example, to blood flow from the atrium to the ventricle.

Apparatus 4800, in this embodiment, also includes support stop 4850 disposed on a proximal side of aptation device 4820. Support stop 4850 is connected to tether 4810 by, for example, an adhesive 4855. In one embodiment, support stop 4850 has a butterfly-like shape of a wire construction that is collapsible for delivery and minimizes obstruction to diastolic flow.

Figure 49:
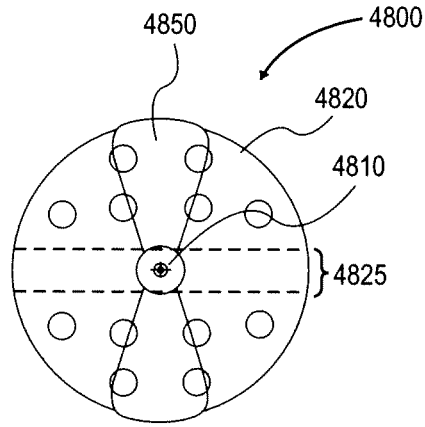
FIG. 49 shows the apparatus of FIG. 48 through line A-A'.

FIG. 49 shows a sectional distal view of apparatus 4800 at line A-A' in FIG. 48. Aptation device 4820, in this embodiment, is a circular body connected to tether 4810 at a midpoint or a center axis. Aptation device 4820 may be made of a material suitable to act as a stop to restrict movement of cusps or leaflets of an atrioventricular valve. A polymer having a thickness on the order of two to five millimeters is suitable. Aptation device 4820, in another embodiment, is a material that is foldable to fit within a catheter sheath for percutaneous delivery. Across a diameter of aptation device 4820 is plication portion 4825. Plication portion 4825 represents, for example, a weak portion in the structure of aptation device 4820 allowing aptation device 4820 to plicate or fold at plication portion 4825.

Referring to FIG. 48 and FIG. 49, proximal to aptation device 4820 on tether 4810 is support stop 4850. Support stop 4850 is disposed, in this embodiment, perpendicular to plication portion 4825. Support stop 4850 has a size and structural characteristic to inhibit the plication of aptation device 4820 for a proximal direction of apparatus 4800 (as viewed). It is appreciated that support stop 4850 may have a variety of shapes. In one aspect, a shape of support stop 4850 is selected to minimize obstruction of blood flow from an atrium through a ventricle. A wire "butterfly" shape frame, as mentioned above, is one suitable configuration.

Figure 50:
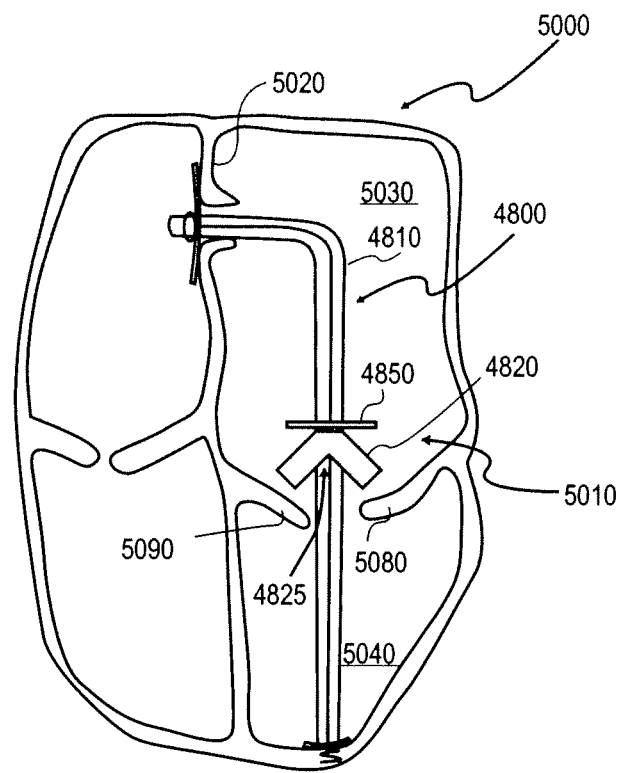
FIG. 50 shows a schematic, cross-sectional front side view of a heart with the apparatus of FIG. 48 deployed on a left side and the cusps or leaflets of the mitral valve in an open position.

FIG. 50 shows apparatus 4800 positioned in the left side of heart 5000. As shown, tether 4810 is connected at a distal end to a wall of left ventricle 5040 and at a proximal end to interatrial septum 5020. Aptation device 4820 is positioned, in this example, in mitral valve annulus 5010.

Figure 51:
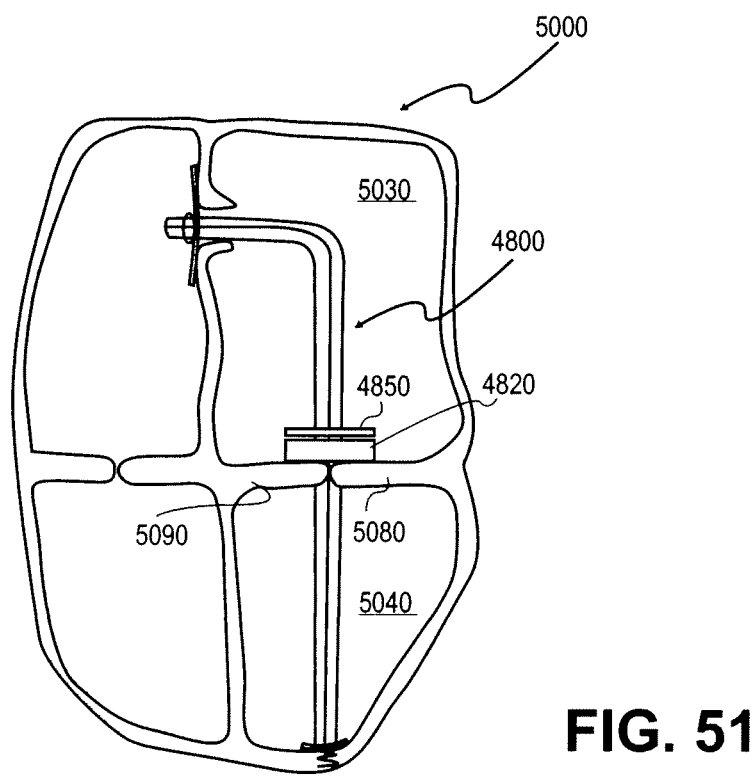
FIG. 51 shows the heart of FIG. 50 with the cusps or leaflets of the mitral valve in a closed position.

In the embodiment shown in FIG. 50, the mitral valve between left atrium 5030 and left ventricle 5040 is shown in an open position. Blood flows from left atrium 5030 into left ventricle 5040. To minimize the inhibition of blood flow from left atrium 5030 to left ventricle 5040, aptation device 4820 plicates at plication portion 4825. FIG. 51 shows heart 5000 during, for example, systole, with cusps or leaflets 5080 and 5090 of the mitral valve closed. The closure of cusps or leaflets 5080 and 5090 and blood flow/pressure return aptation device 4820 to a cylindrical planar shape. Support stop 4850 inhibits aptation device 4820 from plicating, through plication portion 4825, into left atrium 5030. As viewed, aptation device resides entirely in left atrium 5030.

Figure 52:
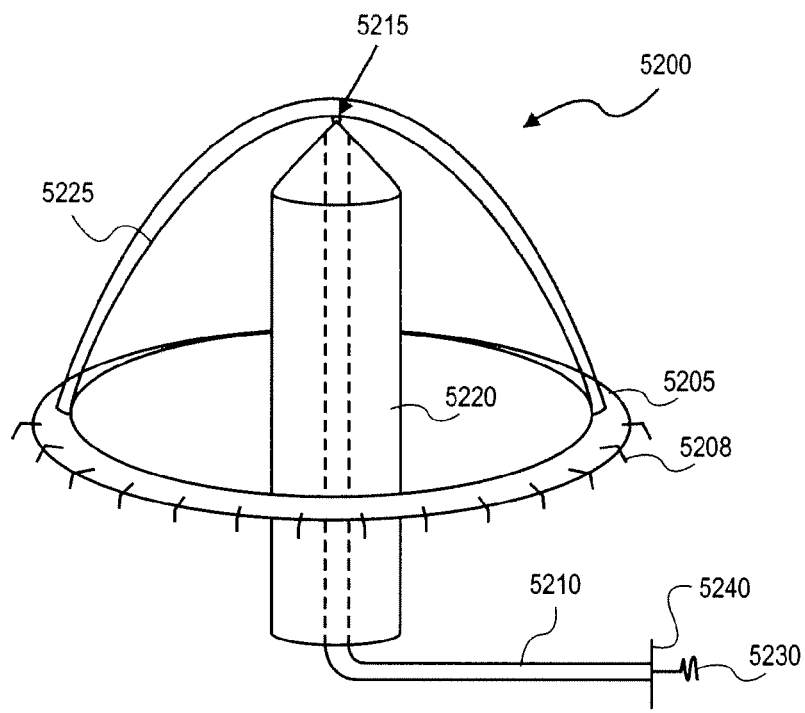
FIG. 52 shows a schematic, top perspective, side view of another embodiment of an apparatus suitable for modifying an atrioventricular valve.

FIG. 52 shows another embodiment of an apparatus suitable for use in modifying the aptation of an atrioventricular valve. Apparatus 5200 includes support annulus 5205, tether 5210 and aptation device 5220. In this embodiment, convex arch 5225 bridges support annulus 5205. Tether 5210 and, optionally, aptation device 5220, are connected at apex 5215 of arch 5225. One alternative is connecting tether 5210 to arch 5225 and aptation device 5220 to tether 5210 at a point between apex 5215 and support annulus 5205.

Support annulus 5205 has an exterior diameter, in one embodiment, suitable for location in an atrioventricular valve annulus (or atrium). The exterior surface of support annulus 5205 may include crenulations or barbs 5208 that extend from support annulus 5205 to anchor support annulus 5205 to, for example, an atrioventricular valve annulus. Tether 5210 may be similar to the tether described above in reference to FIG. 1 and the accompanying text. In one embodiment, tether 5210 may include a duplex spring to be connected to helical coil 5230 at a distal end of tether 5210. Patch 5240 may be disposed between tether 5210 and helical coil 5230. It may be necessary to anchor a distal end of tether 5210 to a wall of a ventricle (through helical coil 5230) prior to connecting a proximal end of tether 5210 to arch 5225. Thus, if done percutaneously, attaching tools may need to be advanced through a catheter to allow connection of a proximal end of tether 5210 to arch 5225.

Figure 53:
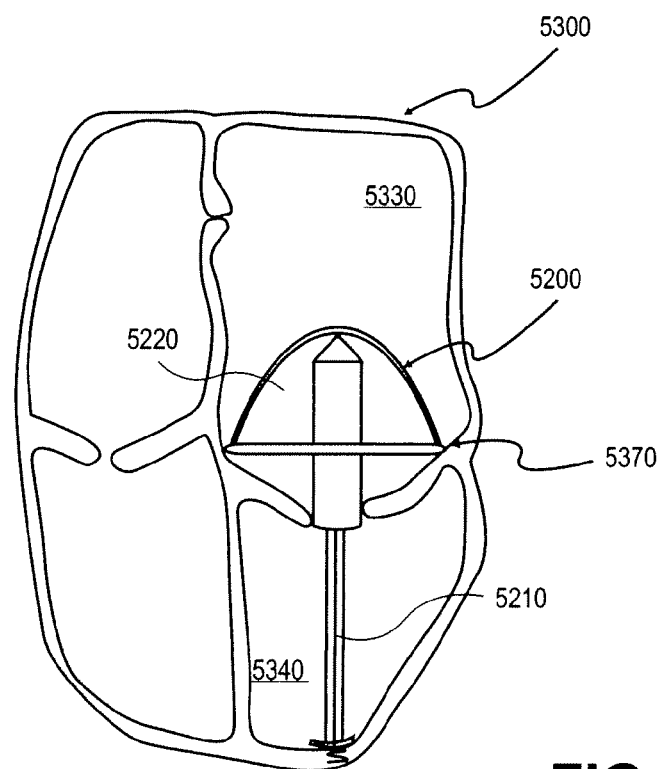
FIG. 53 shows a schematic, perspective, cross-sectional front view of a heart with the apparatus of FIG. 52 deployed on a left side.

FIG. 53 shows apparatus 5200 located in a left side of heart 5300. In one embodiment, support annulus 5205 is disposed within atrioventricular valve annulus 5370, and arch 5225 extends into left atrium 5330. Tether 5210 is connected at a distal end to a wall of left ventricle 5340. In this embodiment, aptation device 5220 extends from apex 5215 of arch 5225 (or from a portion between arch 5225 and support annulus 5205) through cusps or leaflets of the mitral valve, into left ventricle 5340. Aptation device 5220, in this embodiment, is a flexible material that is capable of collapsing in response to the contact from atrioventricular valve cusps or leaflets. Suitable materials, geometries, and configurations for aptation device 5220 are described above with reference to FIGS. 1-12 and the accompanying text.

Figure 54:
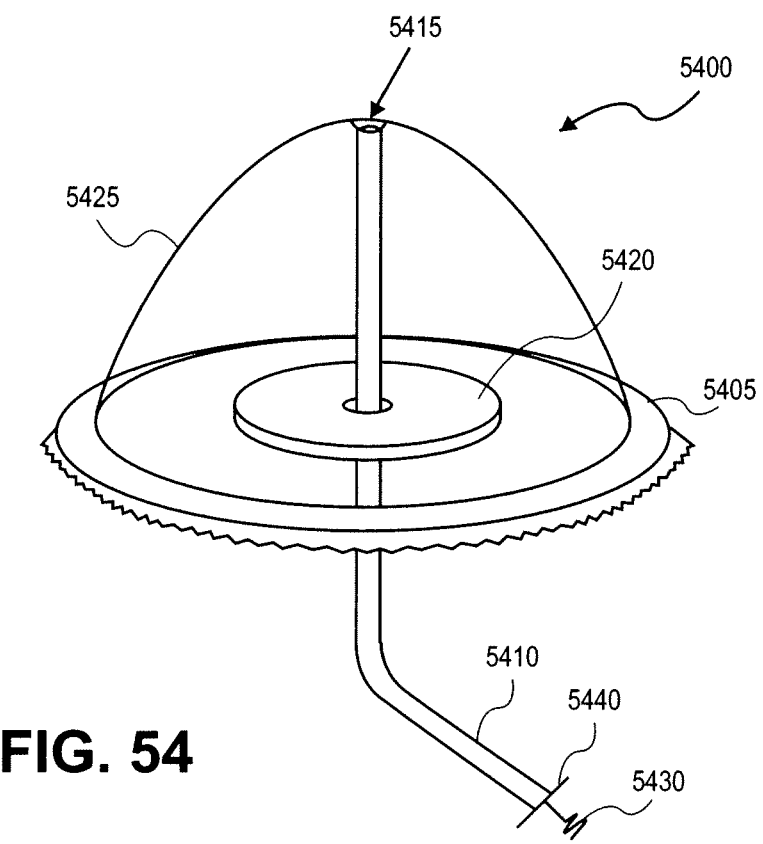
FIG. 54 shows a schematic, top perspective side view of another embodiment of an apparatus suitable for modifying an atrioventricular valve.

FIG. 54 shows another embodiment of an apparatus suitable for use in modifying the aptation of an atrioventricular valve. Apparatus 5400 includes support annulus 5405, tether 5410 and aptation device 5420. In this embodiment, convex arch 5425 bridges support annulus 5405. A proximal end of tether 5410 is connected to apex 5415 of arch 5425. Aptation device 5420 is connected to tether 5410 at a position such that, when apparatus 5400 is positioned in an atrioventricular valve, one or more cusps or leaflets of the atrioventricular valve contact aptation device 5420 when the valve is in a closed position (e.g., mitral valve cusps or leaflets contact aptation device 5420 during systole).

Support annulus 5405 has an exterior diameter, in one embodiment, suitable for location in an atrioventricular valve annulus (or atrium). An exterior surface of support annulus 5405 may include barbs or crenulations (shown as crenulations) to anchor support annulus 5405 to, for example, an atrioventricular valve annulus. Tether 5410 may be similar to the tether described above in referenced to FIG. 1 and the accompanying text. In one embodiment, tether 5410 may include a duplex spring to be connected to helical coil 5430 at a distal end of tether 5410. Patch 5440 may be disposed between tether 5410 and helical coil 5430. As noted above with respect to the embodiment of an apparatus as shown in FIG. 52, it may be necessary to anchor distal end of tether 5410 to a wall of a ventricle (through helical coil 5430) prior to connecting a proximal end of tether 5410 to arch 5425. Thus, if done percutaneously, attaching tools may need to be advanced through a catheter to allow connection of a proximal end of tether 5410 to arch 5425.

In one embodiment, aptation device 5420 is a circular disk shaped device positioned on tether 5410 to contact cusps or leaflets of an atrioventricular valve (e.g., mitral valve) when the cusps or leaflets are desired to be in a closed (aptated) position, such as during systole. Thus, when an atrioventricular valve is closed, aptation device 5420 resides completely in an atrium (e.g., the left atrium). For a further discussion on the function of aptation device 5420, reference is made to FIGS. 43-47 and the accompanying text.

In the above embodiments, apparatuses suitable to contact cusps or leaflets of an atrioventricular valve (e.g., mitral valve) are anchored in place in an atrium or atrioventricular valve annulus, or ventricle or one or more combinations. In some cases, aptation device is anchored to an interatrial septum and a ventricle.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. An apparatus comprising:
a support annulus comprising a tubular first body having a length corresponding to a circumference of one of an interior portion of an atrium and an atrioventricular valve annulus and defining an inner lumen, and a second body extending through the inner lumen, the second body comprising a first end and a second end, the first end and second end capable of being coupled to one another;
an aptation device coupled to the support annulus corresponding to a location to contact cusps of an atrioventricular valve when the support annulus is seated in one of an atrium and an atrioventricular valve annulus,
wherein the support annulus and aptation device are suitable for percutaneous delivery to a patient.

2. The apparatus of claim 1, wherein the first end and the second end of the second body comprise mating ends of a zip tie fastener.

3. The apparatus of claim 1, further comprising a tensioning arm coupled to one of the first end and the second end to advance the one of the first end and the second end relative to the other.

4. The apparatus of claim 1, further comprising a plurality of protruding barbs coupled to an exterior of one side of the support annulus and having a protruding dimension suitable for embedding into a tissue around one of an interior portion of an atrium and an atrioventricular valve annulus.

5. An apparatus comprising:
a support annulus comprising a first end and a second end and a length corresponding to a circumference of one of an interior portion of an atrium and an atrioventricular valve annulus when the first end and the second end are connected; and
an aptation device coupled at a first point and a second point to the support annulus, the first point and the second point selected such that when the support annulus adopts a shape corresponding to a shape of one of an atrium and an atrioventricular valve annulus, the aptation device forms a bridge across the support annulus, and when the support annulus is seated in one of an atrium and an atrioventricular valve annulus, the aptation device is positioned to contact cusps of an atrioventricular valve,
wherein the support annulus and aptation device are suitable for percutaneous delivery to a patient.

6. The apparatus of claim 5, wherein the aptation device comprises a length dimension suitable to extend between cusps of an atrioventricular valve.

7. The apparatus of claim 6, wherein the aptation device comprises a bladder.

8. The apparatus of claim 7, wherein the aptation device comprises a valve coupled to the bladder that controls access to a lumen into the bladder.

9. The apparatus of claim 6, wherein the aptation device comprises a first profile at a portion of the length dimension adjacent the bridge and a larger second profile at a portion of the length dimension that is suitable to extend between cusps of an atrioventricular valve.

10. The apparatus of claim 9, wherein the portion of the length dimension that is suitable to extend between cusps of an atrioventricular valve is divided into at least two segments.

11. The apparatus of claim 9, wherein the first profile and the second profile comprise a side section and collectively the first profile and the second profile resemble a tear drop.

12. The apparatus of claim 6, wherein the aptation device comprises a conical body having a first diameter adjacent the support annulus and a second smaller diameter at a portion of the length dimension that is suitable to extend between cusps of an atrioventricular valve.

13. The apparatus of claim 12, wherein a cross section of the conical body is circular.

14. The apparatus of claim 12, wherein the cross-section of the conical body is elliptical.

15. An apparatus comprising:
a support annulus comprising a first end and a second end and a length corresponding to a circumference of one of an interior portion of an atrium and an atrioventricular valve annulus when the first end and the second end are connected;
an aptation device coupled to the support annulus corresponding to a location to contact cusps of an atrioventricular valve when the support annulus is seated in one of an atrium and an atrioventricular valve annulus; and
at least one tether having a length suitable for extending through a ventricle from, at a proximal end, the support annulus to, at a distal end, a wall of a ventricle,
wherein the support annulus and aptation device are suitable for percutaneous delivery to a patient.

16. The apparatus of claim 15, wherein the aptation device is coupled to the tether.

17. The apparatus of claim 16, wherein a coupling point of the aptation device to the tether is adjustable.

18. The apparatus of claim 5, wherein the aptation device comprises a material that resists thrombosis.

19. The apparatus of claim 5, further comprising:
a catheter comprising a body suitable for introduction and advancement through a patient and comprising a lumen therethrough, wherein in a deployment mode, the support annulus and the aptation device are confined within the lumen.

* * * * *